(12) United States Patent
Tabas et al.

(10) Patent No.: US 6,613,322 B2
(45) Date of Patent: Sep. 2, 2003

(54) METHOD FOR TREATING A SUBJECT SUFFERING FROM CONDITIONS ASSOCIATED WITH AN EXTRACELLULAR ZINC SPHINGOMYELINASE

(75) Inventors: Ira Tabas, New York, NY (US); Scott L. Schissel, Westwood, MA (US); Kevin Jon Williams, Wynnewood, PA (US)

(73) Assignees: The Trustees of Columbia University in the City of New York, New York, NY (US); Thomas Jefferson University, Philadelphia, PA (US)

(*) Notice: Subject to any disclaimer, the term of this patent is extended or adjusted under 35 U.S.C. 154(b) by 0 days.

(21) Appl. No.: 09/518,805

(22) Filed: Mar. 3, 2000

(65) Prior Publication Data

US 2003/0026796 A1 Feb. 6, 2003

Related U.S. Application Data

(63) Continuation of application No. PCT/US98/18362, filed on Sep. 4, 1998, which is a continuation-in-part of application No. 08/937,234, filed on Sep. 5, 1997, now Pat. No. 5,989,803.

(51) Int. Cl.[7] .................. A61K 38/46; A61K 38/43; A61K 38/54
(52) U.S. Cl. .............. 424/94.6; 424/94.1; 424/94.3
(58) Field of Search .................... 424/94.1, 94.6, 424/94.3

(56) References Cited

U.S. PATENT DOCUMENTS

| 4,766,111 A | | 8/1988 | Catsimpoolas |
| 5,916,911 A | * | 6/1999 | Shayman et al. ........... 514/428 |
| 5,919,687 A | * | 7/1999 | Chatterjee .................. 435/199 |

FOREIGN PATENT DOCUMENTS

| JP | 1152632 | 7/1986 |
| JP | 6211668 | 8/1994 |
| JP | 7258132 | 10/1995 |
| JP | 7285957 | 10/1995 |
| JP | 8053387 | 2/1996 |
| JP | 8113535 | 5/1996 |
| JP | 8134002 | 5/1996 |

OTHER PUBLICATIONS

Schissel et al. Circulation, vol. 94, No. 8, Abstract # 0883, 1996.*
Schissel et al. Dissertation Abstracts, vol. 58, No. 9B, 167 pages, DISSABSabstract enclosed, 1997.*
Schissel et al. J. Biol. Chem. vol. 273, No. 5, pp. 2738–2746, Caplus abstract enclosed, 1998.*
Faust, P.L., Wall, D.A., Perara, E., Lingappa, V.R., and Kornfeld, S. (1987) *J. Biol. Chem.* 269, 22477–22480.
Hannun, Y. A. and R. M. Bell. 1989. Functions of sphingolipids and sphingolipid breakdown products in cellular regulation. *Science* 243:500–507.
Kolesnick, R. N. 1991. Sphingomyelin and derivatives as cellular signals. *Prog. Lipid Res.* 30:1–38.
Levade, T., Salvayre, R., and Blazy–Douste, L. (1986) *J. Clin. Chem. Biochem.* 24, 205–220.
Okwu, A. K., X. Xu, Y. Shiratori, and I. Tabas. 1994. Regulation of the threshold for lipoprotein–induced acyl–CoA:cholesterol O–acyltransferase stimulation in macrophages by cellular sphingomyelin content. *J. Lipid Res.* 35:644–655.
Schissel, S. L., E. H. Schuchman, K. J. Williams, and I. Tabas. 1996. $Zn^{2+}$–stimulated sphingomyelinase is secreted by many cell types and is a product of the acid sphingomyelinase gene. *J. Biol. Chem.*
Schissel, S. L., Schuchman, E. H., Williams, K. J., and Tabas, I. (1996) *J. Biol. Chem.* 271, 18431–18436.
Schissel, S. L., J. Tweedie–Hardman, J. H. Rapp, G. Graham, K. J. Williams, and I. Tabas. 1996. Rabbit aorta and human atherosclerotic lesions hydolyze the sphingomyelin of retained low–density lipoprotein. Proposed role for arterial–wall sphingomyelinase in subendothelial retention and aggregation of atherogenic lipoproteins. *J. Clin. Invest.* 98:1455–1464.
Schuchman, E. H., M. Suchi, T. Takahashi, K. Sandhoff, and R. J. Desnick. 1991. Human acid sphingomyelinase. Isolation, nucleotide sequence, and expression of the full–length and alternatively spliced cDNAs. *J. Biol. Chem.* 266:8531–8539.

(List continued on next page.)

*Primary Examiner*—Christopher R. Tate
(74) *Attorney, Agent, or Firm*—John P. White; Cooper & Dunham LLP

(57) ABSTRACT

The present invention provides for a method for treating a subject suffering from a condition associated with an extracellular zinc sphingomyelinase activity which comprises administering to the subject an amount of a zinc sphingomyelinase inhibitor effective to decrease extracellular zinc sphingomyelinase activity in the subject and thereby treat the subject. The present invention also provides for a method for determining whether a compound inhibits an activity of an extracellular zinc sphingomyelinase involving ceramide formation which comprises: (a) contacting a sample containing zinc sphingomyelinase under acidic pH conditions known to be associated with the activity of such zinc sphingomyelinase, with: (i) a substrate of the zinc sphingomyelinase enzyme, and (ii) the compound being evaluated; (b) measuring the ceramide in the sample from (a); (c) determining the amount of zinc sphingomyelinase activity in the sample based on the concentration of ceramide measured in step (b); and (d) comparing the amount of sphingomyelinase activity determined in step (c) with the amount of sphingomyelinase activity determined in the absence of the compound, so as to determine whether the compound inhibits the activity of zinc sphingomyelinase.

5 Claims, 30 Drawing Sheets

OTHER PUBLICATIONS

Skiba, P. J., X. Zha, S. L. Schissel, F. R. Maxfield, and I. Tabas. 1996. The distal pathway of lipoprotein–induced cholesterol esterification, but not sphingomyelinase–induced cholesterol esterification, is energy–dependent. *J. Biol. Chem.* 271:13392–13400.

Spence, M. W., D. M. Byers, F. B. St.C.Palmer, and H. W. Cook. 1989. A new $Zn^{2+}$–stimulated sphingomyelinase in fetal bovine serum. *J. Biol. Chem.* 264:5358–5363.

Tabas, I., Y. Li, R. W. Brocia, S. W. Wu, T. L. Swenson, and K. J. Williams. 1993. Lipoprotein lipase and sphingomyelinase synergistically enhance the association of atherogenic lipoproteins with smooth muscle cells and extracellular matrix. A possible mechanism for low density lipoprotein and lipoprotein(a) retention and macrophage foam cell formation. *J. Biol. Chem.* 268:20419–20432.

Williams, K. J., G. M. Fless, K. A. Petrie, M. L. Snyder, R. W. Brocia, and T. L. Swenson. 1992. Mechanisms by which lipoprotein lipase alters cellular metabolism of lipoprotein(a), low density lipoprotein, and nascent lipoproteins. Roles for low density lipoprotein receptors and heparan sulfate proteoglycans. *J. Biol. Chem.* 267:13284–13292.

Williams, K. J. and I. Tabas. 1995. The response–to–retention hypothesis of early atherogenesis. *Arterioscler. Thromb. Vasc. Biol.* 15:551–561.

Xu, X. and I. Tabas. 1991. Sphingomyelinase enhances low density lipoprotein uptake and ability to induce cholesteryl ester accumulation in macrophages. *J. Biol. Chem.* 266:24849–24858.

Yamamoto, K. (1994) *J. Biochem.* 116, 229–235.

\* cited by examiner

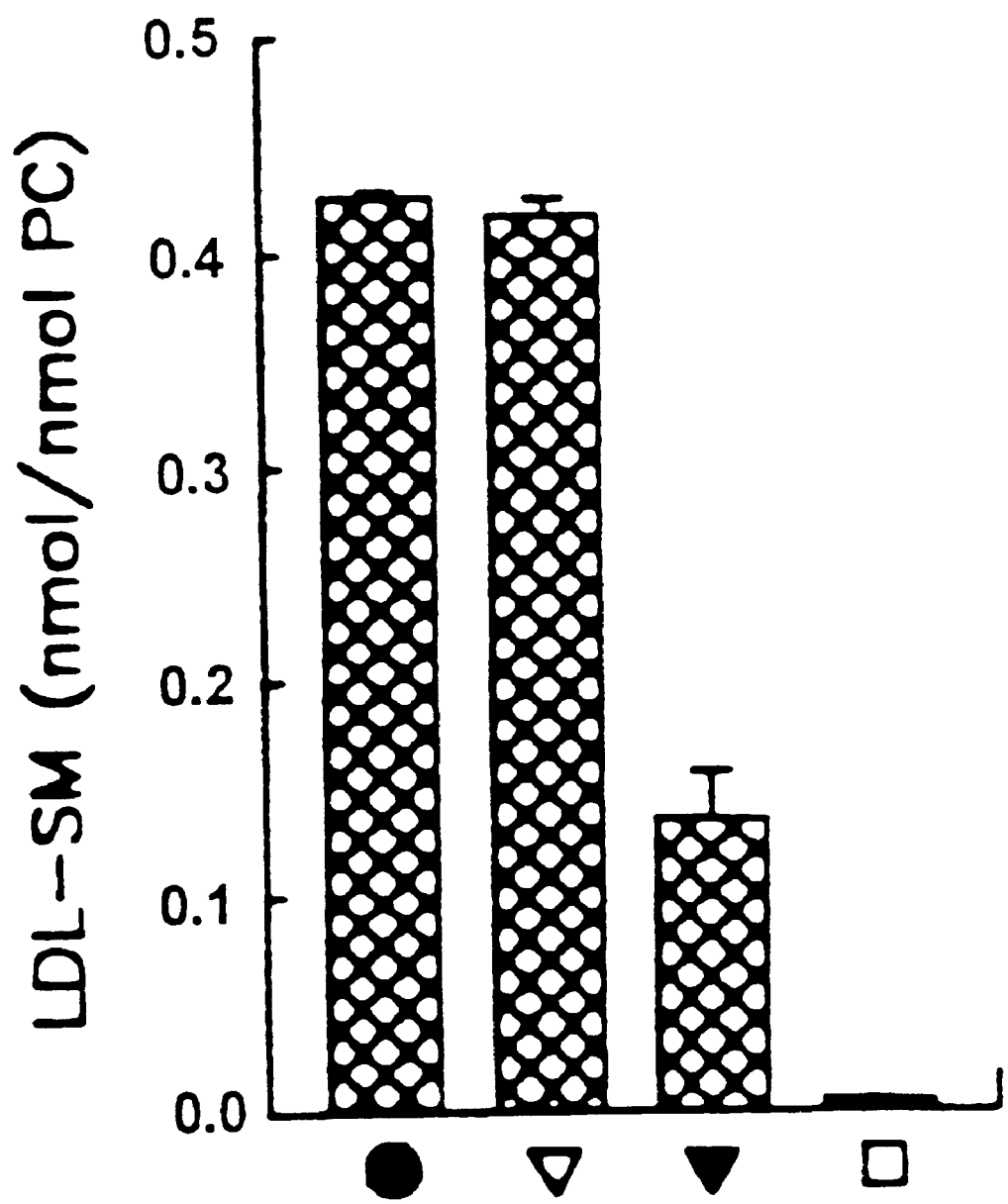

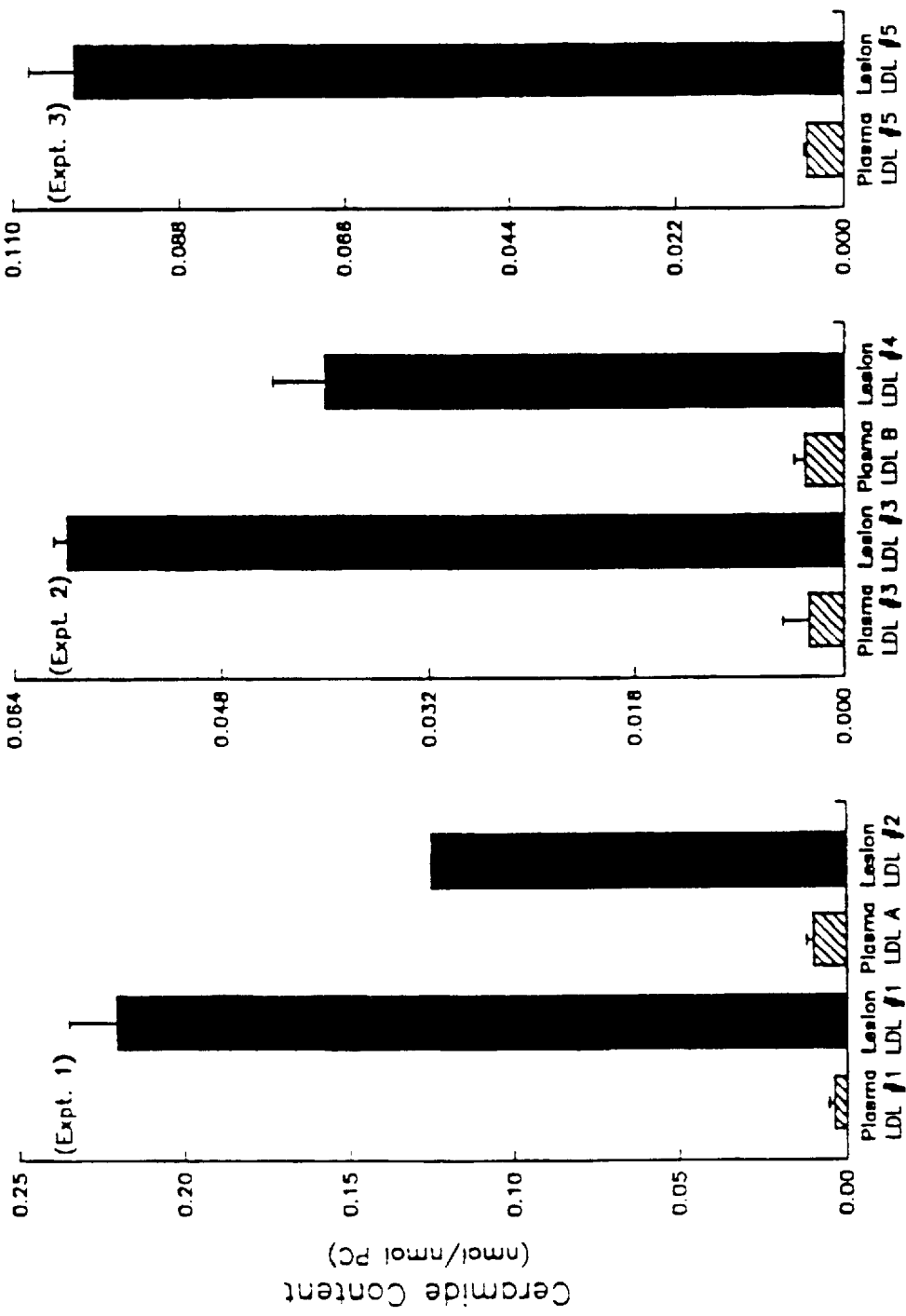

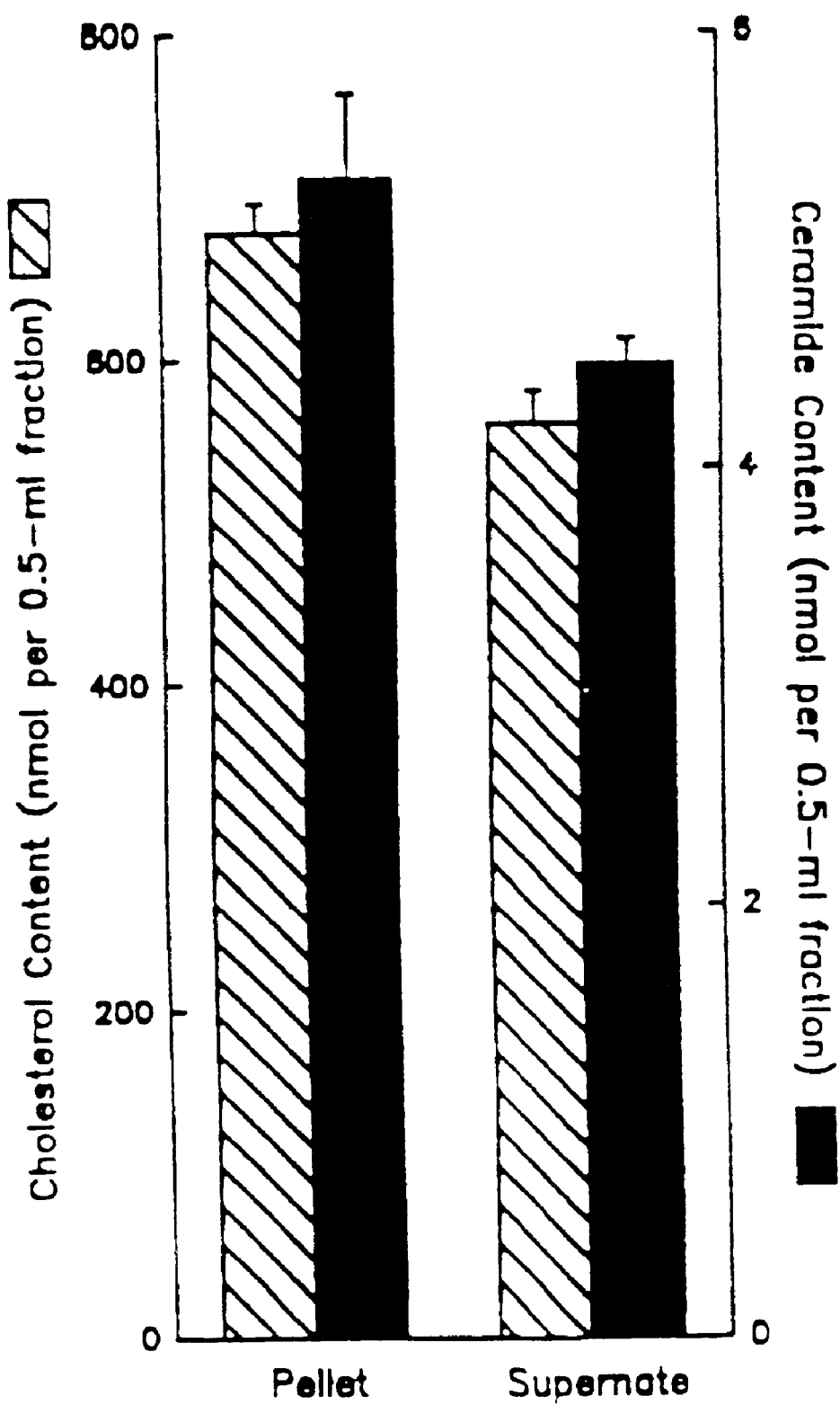

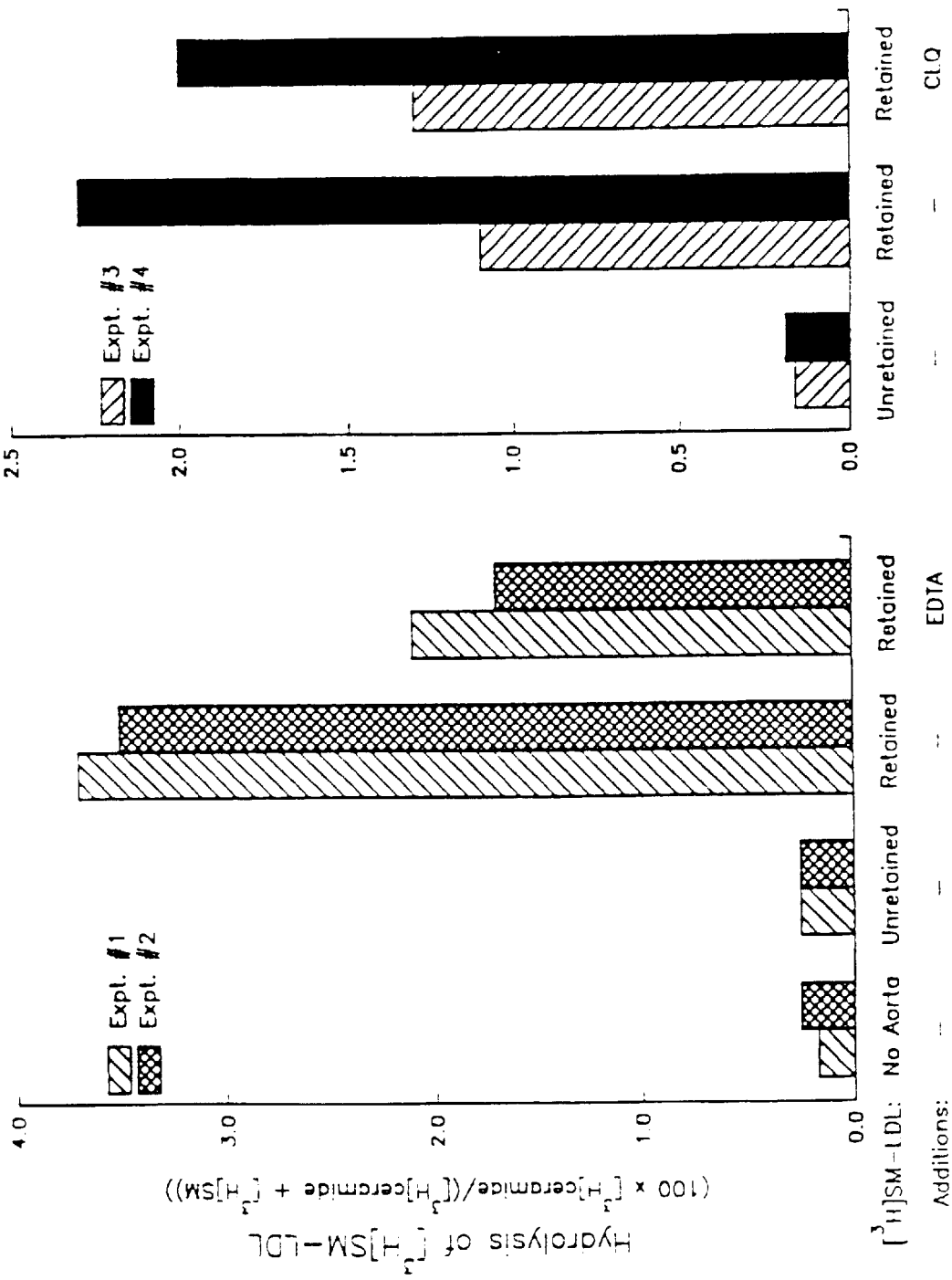

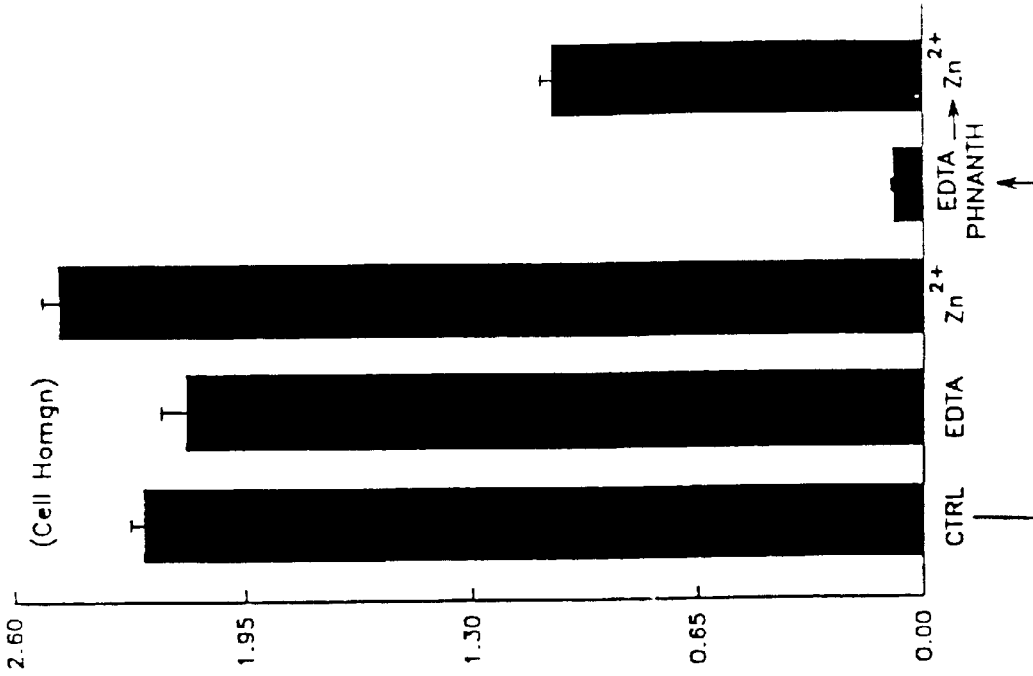

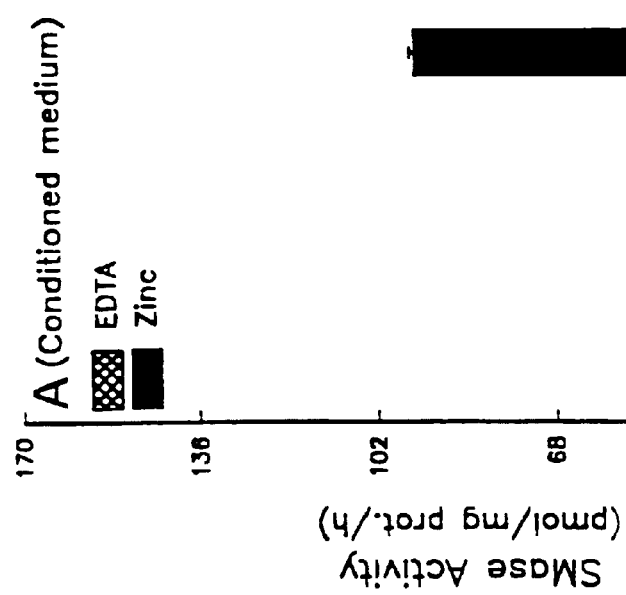
FIG. 20A
FIG. 20B

A (SMase Knockout)

B (Wild type)

METHOD FOR TREATING A SUBJECT SUFFERING FROM CONDITIONS ASSOCIATED WITH AN EXTRACELLULAR ZINC SPHINGOMYELINASE

This application is a continuation of PCT International Application No. PCT/US98/18362, filed Sep. 4, 1998, designating the United States of America, which is a continuation-in-part of and claims the priority of U.S. Ser. No. 08/937,234, filed Sep. 5, 1997, now U.S. Pat. No. 5,989,803 the contents of which are hereby incorporated by reference into the present application.

The invention disclosed herein was made with support under Grants No. HL39703, HL 21006 and HL38956 from National Institutes of Health, U.S. Department of Health and Human Services. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art.

A key early event in atherogenesis is the subendothelial retention of atherogenic lipoproteins, including LDL[1] (Schwenke et al., 1989; Nievelstein et al., 1991), lipoprotein (a) [Lp(a)] (Kreuzer et al., 1994), and triglyceride-rich lipoproteins (Rapp et al., 1994). Atherosclerosis-susceptible regions of the arterial tree are distinguished by their increased retention of lipoproteins compared with resistant regions (Schwenke et al., 1989). The retained lipoproteins are likely to trigger a set of biological responses, such as lipoprotein oxidation and endothelial changes (Steinberg et al., 1989; Ross, 1995), that are central to the atherogenic process (Williams et al., 1995).

Lipoproteins retained in the subendothelium are often extensively aggregated (Nievelstein et al., 1991; Hoff et al., 1985; Guyton et al., 1996). For example, Hoff and colleagues and others (see Hoff et al., 1985; Guyton et al., 1996) have shown that LDL extracted from atherosclerotic lesions is aggregated or has an increased tendency to aggregate, whereas plasma LDL exposed to the same extraction procedure as a control does not aggregate. Furthermore, Frank and colleagues (Nievelstein et al., 1991) used freeze-etch electron microscopy to demonstrate aggregated LDL in the subendothelium of the rabbit aorta as early as two hours after a large bolus injection of human LDL. Subendothelial lipoprotein aggregation is likely to be important in atherogenesis for at least two reasons. First, processes that promote lipoprotein aggregation before or during retention would be expected to increase the amount of material retained (Tabas et al., 1993). Second, aggregated LDL, but not unaggregated LDL, is a potent inducer of macrophage foam cell formation (Hoff et al., 1990; Khoo et al., 1988; Suits et al., 1989; Xu et al., 1991).

SUMMARY OF THE INVENTION

The present invention provides for a method for treating a subject suffering from a condition associated with an extracellular zinc sphingomyelinase activity which comprises administering to the subject an amount of a zinc sphingmyelinase inhibitor effective to decrease extracellular zinc sphingomyelinase activity in the subject and thereby treat the subject. The present invention also provides for a method for determining whether a compound inhibits an activity of an extracellular zinc sphingomyelinase involving ceramide formation which comprises: (a) contacting a sample containing the zinc sphingomyelinase under acidic pH conditions known to be associated with the activity of such zinc sphingomyelinase, with: (i) a substrate of the zinc sphingomyelinase enzyme, and (ii) the compound being evaluated; (b) measuring the concentration of ceramide in the sample from (a); (c) determining the amount of zinc sphingomyelinase activity in the sample based upon the concentration of ceramide measured in step (b); and (d) comparing the amount of sphingomyelinase activity determined in step (c) with the amount of sphingomyelinase activity determined in the absence of the compound, so as to determine whether the compound inhibits the activity of zinc sphingomyelinase.

BRIEF DESCRIPTION OF THE FIGURES

FIGS. 1A–1C. Kinetics of SM hydrolysis and LDL aggregation induced by SMase and the effects of enzymatic inhibition. FIG. 1A: LDL (2 mg/ml) was incubated with 50 mU B. cereus SMase/ml at 37° C. in PES containing 5 nM $MgCl_2$. At the indicated time points, aliquots of the LDL were harvested then assayed for extent of SM hydrolysis (closed triangles) and for aggregation (open squares) FIG. 1B. LDL was incubated in PBS containing 5 mM $MgCl_2$ in the absence of SMase (filled circles), or in the presence of SMase without EDTA (open squares), with 25 mM EDTA present from the start of the incubation (open triangles), or with 25 mM EDTA added after 20 min of incubation (closed triangles) Samples were assayed for turbidity at the indicated timepoints. FIG. 1C, Aliquots from the 180-min timepoint in FIG. 1B were assayed for SM content.

FIGS. 4A–D. Ceramide content and gel-filtration chromatography of LDL extracted from human atherectomy specimens. FIGS. 4A–C represent three separate experiments, analyzing the ceramide contents of a total of five LDL preparations (Lesion LDL #1–#5) extracted from atherectomy material (solid bar). The ceramide contents of five samples of plasma LDL are also shown (diagonal-hatched bars); Plasma LDL #1, #3, and #5 are from the same patients as the same-numbered lesional LDL specimens. Plasma LDL A and B were isolated from the New York Blood Center and used for comparison of Lesion LDL #2 and #4, for which same-donor LDL was not available. Lipids were extracted from 40 μg (by protein mass) of these samples and assayed for ceramide and PC content (data are expressed as nmol ceramide per nmol PC). When expressed as nmol ceramide per mg protein, the values for Plasma LDL #1, A, #3, B, and #5 were 5.1, 4.5, 3.7, 1.6, and 4.1, and the values for Lesion LDL #1–#5 were 58, 51, 22, 32, and 35 respectively. FIG. 4C, 225 μg (500 μl) of Lesion LDL #1 was dialyzed against 6 M guanidine-HCl, 10 mM Tris-HCl, 5 mM EDTA, pH 7.4 (buffer C) and loaded onto a Superose-6-HR 10/30 gel filtration column. The column was run in buffer C at a flow rate of 0.2 ml/min for 175 min, yielding thirty-five 1-ml fractions. The void volume ($V_o$) was 6–7 ml. Aliquots from each fraction were assayed for content of cholesterol (closed circles) and ceramide (open circles) and for the presence of immunoreactive apolipoprotein B-100 using a slot-immunoblot procedure (inset). The cholesterol and ceramide data are expressed as percent maximum value (fraction #11), which was 28.2 nmol cholesterol and 1.2 nmol ceramide per ml (FIG. 4D).

FIGS. 5A–5D. Ceramide is present only in aggregated forms of lesional LDL. FIG. 5A, Lesion LDL #5 from FIGS. 4A–C (900 μg protein in 500 μl of Buffer D [150 mM NaCl, 10 mM, Tris-HCl, 2 mM EDTA, pH 7.4]) was centrifuged for 10 min at 23° C. in an Eppendorf 5415C table-top microcentrifuge at 10,000×g. The pellet was washed twice by resuspension and recentrifugation in buffer D. The final pellet (resuspended in 500 μl of Buffer D) and the original supernate were assayed for total cholesterol (diagonal-hatched bars) and ceramide (solid bars) contents. When the same procedure was conducted with plasma LDL, all of the cholesterol was found in the supernate. FIGS. 5B–D: The procedure described in FIG. 5A was repeated with 750 μl of lesional LDL; 500 μl of the supernatant fraction from was loaded onto a Superose-6-HR 10/30 gel filtration column. The column was run in buffer D, which contains no guanidine-HCl (cf. FIGS. 4A–C) at a flow rate of 0.2 ml/min; the void volume ($V_o$) was 6–7 ml. Aliquots from each fraction were assayed for contents of total cholesterol (FIG. 5B), immunoreactive apo B-100 using a slot-immunoblot procedure (FIG. 5C), and ceramide (FIG. 5D). The cholesterol and ceramide data are expressed as percent maximum value (fraction #10), which was 148.4 nmol cholesterol and 3.5 nmol ceramide per ml; the apo B-100 slot immunoblot data are expressed as relative densitometric units. When plasma LDL was subjected to Superose-6 chromatography as above, all of the cholesterol and apo B-100 eluted in a sharp peak centered around fraction #14 (L in FIG. 5B).

FIGS. 6A–6B. Hydrolysis of [$^3$H]SM-LDL by strips of rabbit aorta. Aortae were isolated from rabbits fed a high-cholesterol diet for 18 d and incubated ex vivo for 3.5 h at 37° C. with 2 mg [$^3$H]palmitate-SM-labeled LDL per ml DMEM/0.2% BSA (usually $^{18}$ 12 mg total). Material extracted from these strips (Retained) was assayed for [$^3$H]SM and [$^3$H]ceramide; approximately 0.1% of the [$^3$H] SM-LDL (10–20 μg LDL protein) was retained during the 3.5-h incubation period. These [$^3$H]lipids were also assayed in $^3$[H]SM-LDL not exposed to aorta but incubated in extraction buffer (No Aorta) as well as in [$^3$H]SM-LDL that was not retained by the aortic strips (i.e., still present in the medium after the 3.5-h incubation) and also incubated in extraction buffer (Unretained). For experiments #1 and #2 (FIG. 6A), portions of the aortic strips were preincubated with DMEM/0.2% BSA containing 15 mM EDTA for 30 min, and the 3.5-h incubation was also carried out in the presence of 15 mM EDNA. For experiments #3 and #4 (FIG. 6B), portions of the aortic strips were preincubated with DMEM/0.2% BSA containing 200 μM chloroquine for 30 min, and the 3.5-h incubation was also carried out in the presence of 200 μM chloroquine.

FIG. 7A: LDL-SM hydrolysis was assayed by measuring ceramide mass. FIG. 7B: LDL aggregation was assayed by measuring turbidity at $A_{430}$.

(FIG. 8A) LDL particles (250 μg protein/mL) were then incubated in the absence (open bars) or presence (solid bars) of S-SMase-containing conditioned media (125 μL/mL) at pH 7.4 for 14 h at 37° C. LDL-[H]SM hydrolysis was assayed by measuring [$^3$H]ceramide. LDL oxidation was assayed by measuring the content of thiobarbituric acid-reactive substances (TBARS) (FIG. 85) and lipid peroxides (LPO) (FIG. 8C) in LDL.

(FIG. 11A) LDL-like [$^3$H]SM-emulsions alone (Control), emulsions mixed with 1 mol apo CIII:8 mol emulsion-SM (+CIII, emulsion-bound+free CIII), and emulsions mixed with apo CIII followed by separation from free apo CIII (+CIII, emulsion-bound only) were prepared as described under "Experimental Procedures". [$^3$H]SM-emulsions were incubated at a concentration of 325 μg CE/mL in the absence (hatched bars) or presence (solid bars) of S-SMase-containing conditioned media (125 μL/mL) at pH 7.4 for 6 h at 37° C. and [$^3$H]SM hydrolysis was assayed by measuring [$^3$H]ceramide. (FIG. 11B) plasma LDL (100 μg protein/mL) from LDL receptor-deficient mice (LDLr0) and LDL receptor-deficient mice expressing a human apo CIII transgene (LDLr0/) CIII) were incubated in the absence (hatched bars) or presence (solid bars) of S-SMase-containing conditioned media (125 μL/mL) at pH 7.4 for 14 h at 37° C. Lipids were then extracted and assayed for ceramide mass.

(FIG. 12A) plasma LDL (100 μg protein/mL) from mice deficient in the LDL receptor (LDLr0) and mice deficient in apolipoprotein E (E0) were incubated in the absence (hatched bars) or presence (solid bars) of S-SMase-containing conditioned media (125 μL/mL) at pH 7.4 for 14 h at 37° C. Lipids were then extracted and assayed for ceramide mass. (FIG. 12B) [$^3$H]SM-emulsions containing lipids in the same proportion as human native plasma LDL (SM:PC molar ratio of 0.5) (Control) or similar emulsions except with a SM:PC molar ratio of 1.5 (SM-rich) were incubated at a concentration of 450 μg CE/mL (50 μL) in the absence or presence of S-SMase-containing conditioned media (125 μL/mL) at pH 7.4 for 12 h at 37° C. [$^3$H]SM hydrolysis was assayed by measuring [$^3$H]ceramide.

FIGS. 14A–B. Sequential chelation and addition of $Zn^{2+}$ to secreted and intracellular SMase. Serum-free conditioned medium and a cell homogenate from J774 macrophages were prepared as described in "Experimental Procedures". FIG. 14A, conditioned medium (CM) was assayed for SMase activity using 250 nM [$^3$H]sphingomyelin in Triton X-100 micelles in the presence of either 5 mM EDTA (first bar) or 0.1 mM $ZnCl_2$ (second bar) for 1 h at 37° C. at pH 5.0. An aliquot of the Zn-activated conditioned medium was then incubated for 18 h in the presence of 10 mM EDTA, 10 mM 1,10-phenanthroline, and 0.6% Triton X-100 at 4° C. (EDTA PHNANTH) and then assayed for SMase activity (third bar). After chelation, a portion of this partially inactivated conditioned medium was then dialyzed against zinc-containing buffer C (150 mM NaCl, 10 mM Tris-HCl, 1 mM $ZnCl_2$, 0.6% Triton X-100, pH 7.4) for 18 h and then assayed for SMase activity (fourth bar). FIG. 14B, an aliquot of cell homogenate (Cell Homgn) was assayed for SMase activity in the presence of assay buffer alone (first bar), 5 mM EDTA (second bar), or 0.1 mM $ZnCl_2$ (third bar). Another aliquot of cell homogenate was incubated for 8 h in the presence of 10 mM EDTA, 10 mm 1,10-phenanthroline, and 0.6% Triton X-100 (EDTA PHNANTH) at 4° C. and then assayed for SMase activity (fourth bar). An aliquot of this chelator-treated cell homogenate was then dialyzed against zinc-containing buffer C for 18 h and then assayed for SMase activity (fifth bar).

FIGS. 20A–B. Cultured human endothelial cells secrete abundant amounts of S-SMase. Serum-free conditioned media collected over 24 h and cell homogenates from human monocyte-derived macrophages (HMDM( ), J774 macrophages (J774M( ), human coronary artery endothelial cells (HCAEC), and HUVEC were prepared as described in "Experimental Procedures" and assayed for SMase activity in the presence of either 5 mM EDTA (cross-hatched bars) or 0.1 mM $ZnCl_2$ (solid bars). 95% of S-SMase activity from HUVECs was immunoprecipitated by an affinity-purified anti-S-SMase antibody, and 97% of HUVEC S-SMase activity was inactivated by chelation of $Zn^{2+}$ with 10 mM EDTA plus 10 mM 1,10-phenanthroline. These data indicate that a single enzyme accounts for SMase activity in the conditioned medium ok HUVECs.

FIG. 21B. As a control for leakiness of the cell monolayer or for transcytosis, FLAG-tagged S-SMase was added to the upper chamber of parallel dishes of those in Expts. #1 & #2 and incubated with the cells as described above. At the end of the 1-h incubation, FLAG-tagged S-SMase in media above the cells (ap [apical]) and in media under the insert (bl [basolateral]) was detected by immunoblotting with anti-FLAG antibody.

DETAILED DESCRIPTION OF THE INVENTION

Figure 1B:
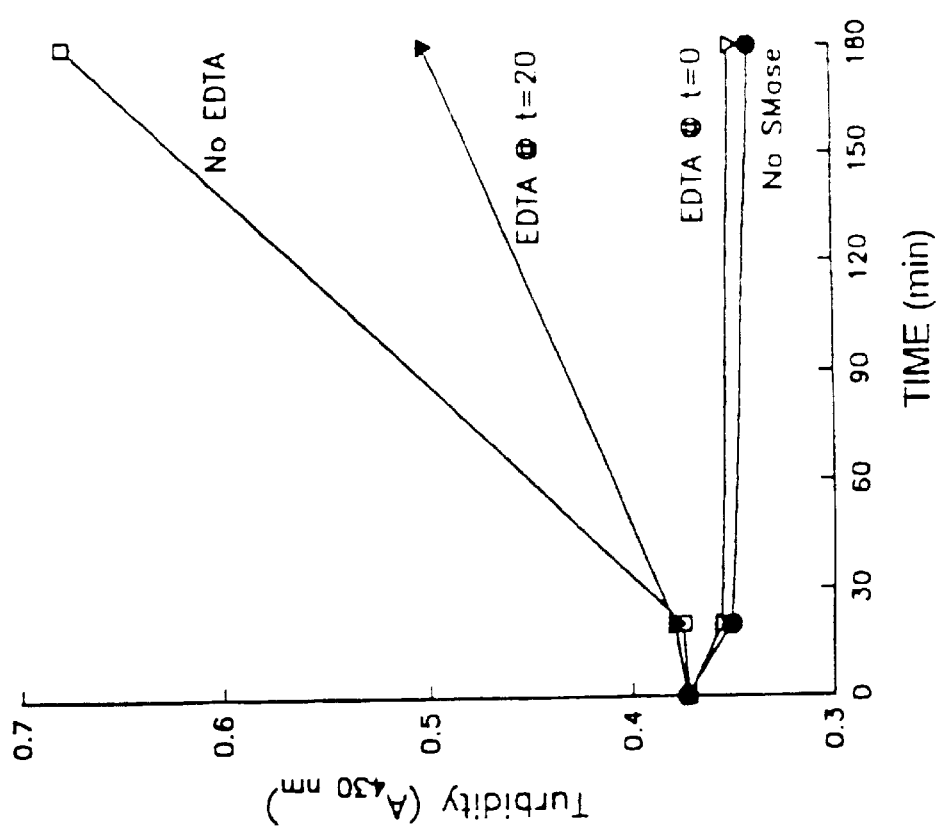

The present invention provides for a method for treating a subject suffering from a condition associated with an extracellular zinc sphingomyelinase activity which comprises administering to the subject an amount of a zinc sphingmyelinase inhibitor effective to decrease extracellular zinc sphingomyelinase activity in the subject and thereby treat the subject.

In one embodiment of the present invention, the extracellular zinc sphingomyelinase is present in the subject at a concentration which is higher than that present in the subject prior to the onset of the condition. In another embodiment of the present invention, the method of claim 1, wherein extracellular zinc sphingomyelinase is present in the subject at a concentration which is lower than that present in the subject prior to the onset of the condition.

As used herein "extracellular zinc sphingomyelinase" is encompassed by lysosomal zinc sphingomyelinase or L-SMase; secreted or secretory zinc sphingomyelinase or S-SMase; or zinc sphingomyelinase which was originally an intracellular zinc sphingomyelinase enzyme and is released into the extracellular environment. Extracellular zinc sphingomyelinase is referred to herein as the zinc sphingomyelinase. Extracellular zinc sphingomyelinase is a metalloenzyme which is capable of binding zinc and capable of being activated by zinc. As used herein, extracellular zinc sphingomyelinase is encompassed by sphingomyelinase already bound to zinc or sphingomyelinase not yet bound to zinc but capable of binding zinc. Extracellular zinc sphingomyelinase may be produced from a Golgi secretory pathway of a cell or a lysosomal pathway of a cell, or by other processes leading to release into an extracellular environment or by a combination of these pathways.

In another embodiment of the present invention, the condition may be an atherosclerotic vascular disease, an inflammatory disease, an infectious disease, an autoimmune disease, or a demyelinating disease. The atherosclerotic vascular disease may be coronary artery disease, cerebral vascular disease, peripheral vascular disease transplantation atherosclerosis, vein graft atherosclerosis, or vaculitis-induced atherosclerosis. The demyelinating disease may be multiple sclerosis. The demyelinating disease may also be progressive multifocal leucoencephalopathy, Guillain-Barre syndrome, Retrobulbar neuritis, acute rubella encephalitis, chronic relapsing polyneuropathy, intravascular lymphomatosis, Krabbe disease, globoid cell leukodystrophy, subacute combined degeneration of the spinal cord and brain, allergic encephalitis, murine caronavirus, hepatitis virus infection, or Theiler's murine encephalomyelitis. The subject may be a mouse which is a Twitcher mouse or a rat which is a HAM rat. The subject may be an animal which has experimental allergic encephalitis.

In one embodiment of the present invention, the zinc sphingomyelinase inhibitor may comprises a peptide or polypeptide, a peptidomimetic compound, an organic compound, a nucleic acid, an inorganic compound, or an antibody or fragment thereof. In another embodiment, the inhibitor is an antibody capable of binding to and inactivating zinc sphingomyelinase. The inhibitor may be an antibody which comprises a monoclonal or a polyclonal antibody.

In another embodiment of the present invention, the inhibitor comprises a compound capable of competing with sphingomyelin for binding to the active site of naturally occuring sphingomyelinase. In a further embodiment of the present invention, the inhibitor may be a pseudoenzyme.

In one embodiment of the present invention, the administration comprises intralesional, intraperizoneal, intramuscular or intravenous injection; infusion; liposome-mediated delivery; topical, nasal, oral, anal, subcutaneous, vaginal, sublingual, intrathecal, urethetal, transdermal ocular or otic delivery.

The present invention provides that the zinc sphingomyelinase inhibitor may comprise a portion of a naturally occuring zinc sphingomyelinase. The portion may consist essentially of a sphingomyelin binding site of the sphingomyelinase. In another embodiment, the zinc sphingomyelinase inhibitor is a compound having a structure which mimics the structure of a substrate of sphingomyelinase or of a product of sphingomyelinase. In another embodiment, the substrate of sphingomyelinase is sphingomyelin. In another embodiment, the product of sphingomyelinase is ceramide or choline phosphate.

The present invention provides for a method for determining whether a compound inhibits an activity of an extracellular zinc sphingomyelinase involving ceramide formation which comprises: (a) contacting a sample containing the zinc sphingomyelinase under acidic pH conditions known to be associated with the activity of such zinc sphingomyelinase, with: (i) a substrate of the zinc sphingomyelinase enzyme, and (ii) the compound being evaluated; (b) measuring the concentration of ceramide in the sample from (a); (c) determining the amount of zinc sphingomyelinase activity in the sample based upon the concentration of ceramide measured in step (b); and (d) comparing the amount of sphingomyelinase activity determined in step (c) with the amount of sphingomyelinase activity determined in the absence of the compound, so as to determine whether the compound inhibits the activity of zinc sphingomyelinase.

The present invention provides for a method for determining whether a compound inhibits an activity of an extracellular zinc sphingomyelinase involving ceramide formation which comprises: (a) contacting a sample containing the zinc sphingomyelinase under neutral pH conditions, with: (i) a substrate of the zinc sphingomyelinase enzyme, and (ii) the compound being evaluated; (b) measuring the concentration of ceramide in the sample from (a); (c) determining the amount of zinc sphingomyelinase activity in the sample based upon the concentration of ceramide measured in step (b); and (d) comparing the amount of sphingomyelinase activity determined in step (c) with the amount of sphingomyelinase activity determined in the absence of the compound, so as to determine whether the compound inhibits the activity of zinc sphingomyelinase.

As used herein, acidic DH encompasses a pH range from about pH 2.5 to about pH 6.9 and neutral pH encompasses a pH range from about pH 7 to about pH 7.5. The present invention provides for methods which may be carried out within a pH range from about 2.5 to about 7.5.

In one embodiment, the substrate may comprise sphingomyelin or a derivative thereof or a lipoprotein. The substrate may be detectably labeled. The lipoprotein may be a modified lipoprotein. The detectable label may comprise a radioisotope or a fluorophor. The lipoprotein may comprise an oxidized lipoprotein, a phospholipase-A-II treated lipoprotein, an apolipoprotein-C-III-enriched population of lipoproteins, a lipoprotein obtained from an apolipoprotein-E knock-out mouse, or a sphingomyelin-enriched population of lipoproteins or emulsions thereof at neutral pH.

In one embodiment, steps (a) through (d) of the above-described method are repeated for multiple compounds.

The present invention also provides for a method for screening a library of compounds to identify a compound capable of inhibiting an activity of zinc sphingomyelinase involving ceramide formation which comprises: (a) contacting a zinc sphingomyelinase under acidic pH conditions known to be associated with the activity of such zinc sphingomyelinase, with: (i) a substrate of sphingomyelinase, and (ii) a sample from a library of compounds being evaluated; (b) measuring the concentration of ceramide in the sample from (a); and (c) determining the amount of zinc sphingomyelinase activity in the sample based upon the concentration of ceramide measured in step (b); and (d) comparing the amount of sphingomyelinase activity determined in step (c) with the amount of sphingomyelinase activity determined in the absence of the sample, so as to determine whether the sample inhibits the activity of zinc sphingomyelinase enzyme, and (d) repeating steps (a) through (d) with limiting dilutions of the sample so as to identify the compound in the sample capable of inhibiting zinc sphingomyelinase. The screen may also be carried out at neutral pH.

The present invention also provides for a method for determing whether a subject is at increased risk for becoming afflicted with an increase in the concentration of extracellular zinc sphingomyelinase activity in the subject which comprises: (a) obtaining a sample of a body fluid from the subject; (b) determining the amount of extracellular zinc sphyingomyelinase activity in the body fluid sample, and (c) comparing the amount of extracellular zinc sphyingomyelinase activity determined in step (a) with the amounts of extracellular zinc sphyingomyelinase activity determined for the subject at earlier points in time, an increase in the amount of such activity indicating that the subject is at increased risk for such condition.

The present invention also provides for a method for determing whether a subject is at increased risk for becoming afflicted with an increase in the concentration of extracellular zinc sphingomyelinase activity in the subject which comprises: (a) obtaining a sample of a body fluid from the subject; (b) determining the amount of extracellular zinc sphyingomyelinase activity in the body fluid sample, and (c) comparing the amount of extracellular zinc sphyingomyelinase activity determined in step (a) with the a predetermined standard extracellular zinc sphyingomyelinase activity so as to determine whether the subject is at increased risk for such condition.

The predetermined standard extracellular zinc sphingomyelinase activity may be determined by identifying the activity present in samples taken from a large number of individuals. The activity levels determined could then be compared so as to determine a statistical norm for the population of individuals. The population may be controlled for age of the individuals, sex of the individuals, relative health, relative fitness, etc. From such samplings, a standard extracellular sphingomyelinase activity may be determined.

In one embodiment of the present invention, the condition may be an atherosclerotic vascular disease, an inflammatory disease, an infectious disease, an autoimmune disease, or a demyelinating disease. The atherosclerotic vascular disease may be coronary artery disease, cerebral vascular disease, peripheral vascular disease, transplantation atherosclerosis, vein graft atherosclerosis, or vaculitis-induced atherosclerosis. The demyelinating disease may be multiple sclerosis, progressive multifocal leucoencephalopathy, Guillain-Barre syndrome, retrobulbar neuritis, acute rubella encephalitis, chronic relapsing polyneuropathy, intravascular lymphomatosis, Krabbe disease, globoid cell leukodystrophy, subacute combined degeneration of the spinal cord and brain, allergic encephalitis, murine caronavirus, hepatitis virus infection, or Theiler's murine encephalomyelitis. The body fluid may comprise plasma, blood, serum, interstitial fluid, cerebrospinal fluid, joint fluid, tears, semen, urine, saliva, bile, or amniotic fluid.

The present invention provides for a method for determining whether a subject has lipoproteins susceptible to extracellular zinc sphingomyelinase activity and thus is at increased risk for becoming afflicted with a condition associated with extracellular zinc sphingomyelinase activity which comprises: (a) obtaining a sample of a body fluid from the subject;(b) isolating the lipoproteins present in the sample;(c) contacting the isolated lipoproteins with zinc sphingomyelinase enzyme under acidic pH conditions known to be associated with the activity of such zinc sphingomyelinase;(d) measuring the concentration of ceramide in step (c); and(e) comparing the amount of ceramide detected in step (d) with an amount of ceramide produced from lipoproteins isolated from a normal subject, thereby detecting whether the subject has lipoproteins susceptible to extracellular zinc sphingomyelinase so as to determine whether the subject is at increased risk for becoming afflicted with a condition associated with extracellular zinc sphingomyelinase activity. The contacting of step (c) may also be performed under neutral pH conditions.

The present invention provides for a pharmaceutical composition comprising an amount of an inhibitor of an extracellular zinc sphingomyelinase enzyme effective to inhibit the activity of such zinc sphingomyelinase enzyme in a subject and a pharmaceutically acceptable carrier. The carrier may comprise a diluent. The carrier may further comprise an adjuvant, a liposome, a microencapsule, a polymer encapsulated cell, a biodegradable plastic or a retroviral vector. The composition may be in a form suitable for aerosol, intravenous, oral or topical administration.

In one embodiment of the invention, the subject may be an animal, an animal model or a human.

In addition to the inhibitor being derived from a naturally-occurring form of zinc sphingomyelinase, the present invention also embraces other agents such as polypeptide analogs of zinc sphingomyelinase enzyme. Such analogs include fragments of zinc sphingomyelinase enzyme Following the procedures of the published application by Alton et al. (WO 83/04053), one can readily design and manufacture genes coding for microbial expression of polypeptides having primary conformations which differ from the natural zinc sphingomyelinase enzyme which would be specified for in terms of the identity or location of one or more residues (e.g., substitutions, terminal and intermediate additions and deletions). Alternately, modifications of cDNA and genomic genes can be readily accomplished by well-known site-directed mutagenesis techniques and employed to generate analogs and derivatives or zinc sphingomyelinase enzyme. Such agents share at least one of the biological properties of zinc sphingomyelinase enzyme but may differ in others. As examples, inhibitors of zinc sphingomyelinase of the invention include those agents which are foreshortened by e.g., deletions; or those which are more stable to hydrolysis (and, therefore, may have more pronounced or longerlasting effects than naturally-occurring); or which have been altered to delete or to add one or more potential sites for O-glycosylation and/or N-glycosylation or which have one or more cysteine residues deleted or replaced by e.g., alanine or serine residues and are potentially more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within zinc sphingomyelinase, which fragments may possess one property of zinc sphingomyelinase (i.e. substrate binding) and not others (e.g., enzymatic activity). It is noteworthy that activity is not desired for any one or more of the products of the invention to have therapeutic utility or utility in other contexts, such as in assays of zinc sphingomyelinase activity. Competitive antagonists may be quite useful in, for example, cases of overproduction of zinc sphingomyelinase or cases of atherosclerosis where the endothelial cells associated with lesions overexpress the enzyme.

One embodiment of the present invention is wherein the agent or the inhibitor is a peptidomimetic compound. The peptidomimetic compound may be at least partially unnatural The peptidomimetic compound may be a small molecule mimic of the binding site of zinc sphingomyelinase or a mimic of the active site of zinc sphingomyelinase. The compound may have increased stability, efficacy, potency and bioavailability by virtue of the mimic. Further, the compound may have decreased toxicity. The peptidomimetic compound may have enhanced mucosal intestinal permeability. The compound may be synthetically prepared. The compound of the present invention may include LDL or unnatural amino acids, alpha, alpha-disubstituted amino acids, N-alkyl amino acids, lactic acid (an isoelectronic analog of alanine). The peptide backbone of the compound may have at least one bond replaced with PSI-[CH=CH] (Kempf et al. 1991). The compound may further include trifluorotyrosine, p-Cl-phenylalanine, p-Br-phenylalanine, poly-L-propargylglycine, poly-D,L-allyl glycine, or poly-L-allyl glycine.

One embodiment of the present invention is a peptidomimetic compound having the biological activity of zinc sphingomyelinase wherein the compound has a bond, a peptide backbone or an amino acid component replaced with a suitable mimic. Examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, cysteine (acetamindomethyl). N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995)

In one embodiment of the invention, the substrate comprises sphingomyelin or a derivative thereof in a detergent micelle at acidic pH; or a modified lipoprotein. In another embodiment of the invention, the substrate is detectably labeled. In another embodiment of the invention, the detectable label comprises radioisotope or fluorescence.

The invention also provides for a method for screening a library of compounds to identify a compound capable of inhibiting zinc sphingomyelinase enzyme activity which comprises: (a) incubating a zinc sphingomyelinase enzyme, under acid pH conditions suitable for zinc sphingomyelinase enzyme activity, with: (i) a substrate of sphingomyelinase enzyme, and (ii) a sample from a library of compounds; (b) detecting the amount of sphingomyelinase enzyme activity produced by determining whether there exists an increase in ceramide concentration in the incubate; and (c) comparing the amount of enzyme activity detected in step (b) with an amount of enzyme activity detected in the absence of the compound, thereby evaluating the ability of the sample to inhibit activity of zinc sphingomyelinase enzyme, and (d) repeating step (a) with limiting dilutions of the sample so as to identify the compound in the sample capable of inhibiting zinc sphingomyelinase enzyme activity. The incubating in step (a) may be carried out at neutral pH.

In one embodiment of the invention, the carrier comprises a diluent. In another embodiment of the invention, the carrier comprises an appropriate adjuvant, a liposome, a microencapsule, a polymer encapsulated cell, a biodegradable plastic substance or a retroviral vector. In another embodiment of the invention, the pharmaceutically acceptable carrier is an aerosol, intravenous, oral or topical carrier, In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The active ingredient can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The active ingredient can also be administered orally either in liquid or solid composition form. Compositions suitable for oral administration include solid forms, such as pills. capsules, granules, tablets, and powders, and liquid forms, such as solutions, syrups, elixirs, and suspensions. Forms useful for parenteral administration include sterile solutions, emulsions, and suspensions.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

EXAMPLE 1

Rabbit Aorta and Human Atherosclerotic Lesions Hydrolyze the Sphingomyelin of Retained Low-density Lipoprotein Role for Arterial-wall Sphingomyelinase in Subendothelial Retention and Aggregation of Atherogenic Lipoproteins Aggregation and retention of low-density lipoprotein (LDL) in the arterial wall are key events in atherogenesis, but the mechanisms in vivo are not yet fully understood. Exposure of LDL to bacterial sphingomyelinase (SMase) in vitro leads to the formation of LDL aggregates that can be retained by extracellular matrix and that are able to stimulate macrophage foam cell formation. Evidence is provided herein that shows retained LDL is hydrolyzed by an arterial-wall SMase activity. First, SMase-induced aggregation was demonstrated to be caused by an increase in particle ceramide content, even in the presence of excess SM. This finding is compatible with data showing that lesional LDL is enriched in SM, though its ceramide content has not previously been reported. To address this critical compositional issue, the ceramide content of lesional LDL was assayed and, remarkably, found to be 10–50-fold enriched compared with plasma LDL ceramide. Furthermore, the ceramide was found exclusively in lesional LDL that was aggregated; unaggregated lesional LDL, which accounted for 20–25% of the lesional material, remained ceramide-poor. When [$^3$H] SM-LDL was incubated with strips of rabbit aorta ex vivo, a portion of the LDL was retained, and the [$^3$H]SM of this portion, but not that of unretained LDL, was hydrolyzed to [$^3$H3ceramide by a nonlysosomal arterial hydrolase. In summary, LDL retained in atherosclerotic lesions is acted upon by an arterial-wall SMase, which may participate in LDL aggregation and possibly other SMase-mediated processes during atherogenesis.

The mechanism of lipoprotein aggregation in lesions is not known. Lipoprotein aggregation can be induced in vitro by vortexing (Khoo et al., 1988), extensive phospholipase C hydrolysis (Suits et al., 1989), extensive oxidation (Hoff et al., 1989), and limited hydrolysis with bacterial sphingomyelinase (SMase) (Xu et al., 1991). Vortexing and extensive hydrolysis by phospholipase C are unlikely to be physiologically important. LDL oxidation does occur in arteries (Steinberg et al., 1989), but, as mentioned above, subendothelial LDL aggregates have been shown to be present in normal rabbit aorta as early as two hours after an intravenous bolus injection of LDL (Nievelstein et al., 1991), which may be too soon for substantial LDL oxidation to occur in these normal vessels. One goal of the current study was to test the possible physiological relevance of SMase-induced lipoprotein aggregation. In particular, it was demonstrated that the mechanism of SMase-induced aggregation of LDL in vitro is entirely consistent with a role for SM hydrolysis in LDL aggregation in vivo, that extracellular, retained LDL extracted from human atherosclerotic lesions shows evidence of having been acted upon by an arterial SMase, and that strips of rabbit aorta ex vivo can hydrolyze the SM of retained LDL. The results support a role for arterial SMase in LDL aggregation and possibly other SMase-mediated processes during atherogenesis.

Methods

Materials. sn-1,2-diacylglycerol kinase (from *Escherichia coli*) was purchased from Calbiochem (San Diego, Calif.). Cardiolipin and 1,2-dioleoyl glycerol were purchased from Avanti Polar Lipids Alabaster, Ala.). The Superose 6 HR 10/30 gel filtration column was obtained from PHARMACIA® (Piscataway, N.J.). [9,10-$^3$H] palmitic acid, [$\gamma$-$^{32}$P] ATP, and Na$^{125}$I were obtained from DuPont-New England Nuclear (Boston, Mass.). Tissue culture media, tissue culture reagents, and human recombinant epidermal growth factor were purchased from Life Technologies (Baltimore, Md.), fetal bovine serum was from GEMINI® Bioproducts (Calabasas, Calif.). and glass tissue culture plates were from CORNING® (Corning, N.Y.). SMase (from *Bacillus cereus*) and all other reagents were from SIGMA® (St. Louis, Mo.). Peroxidase-conjugated goat anti-rabbit IgG was purchased from PIERCE® Chemical Co. (Rockford, Ill.).

Synthesis of [$^3$]SM. [N-palmitoyl-9,10-$^3$H]SM was synthesized as previously described (Sripada et al., 1987; Ahmad et al. 1985) Briefly, [9,10-$^{-3}$H]palmitic acid (25 mCi, 450 nmol) was stirred for 12 h at room temperature with an equimolar equivalent of (N)-hydroxysuccinimide and with 3-molar equivalents of 1,3-dicyclohexylcarbodiimide in (N,N)-dimethylformamide. The reaction was run under dry argon in the dark. Sphingosylphosphorylcholine (300 nmol) and (N,N)-diisopropylethylamine (10 $\mu$l) were then added and the reaction was stirred another 12 h at room temperature. The reaction was stopped by evaporating the (N,N)-dimethylformamide under a stream of N$_2$. [N-palmitoyl-9, 10-$^3$H]SM was purified by preparative thin-layer chromatography of the reaction products three consecutive times in chloroform:methanol (95:5) and then twice in chloroform:methanol:acetic acid:water (50:25:8:4). Greater than 95% of the [N-palmitoyl-9,10-$^3$H]SM was converted to [N-palmitoyl-9,10-$^{-3}$H]ceramide after treatment with 10 mU SMase/ml (*Bacillus cereus*) for 1 h at 37° C., as assayed by TLC, indicating a pure, functional substrate.

Lipoproteins. LDL (density, 1.020–1.063 g/ml) was isolated from fresh human plasma by preparative ultracentrifugation as previously described (Havel et al., 1955). Plasma LDL was labeled with [N-palmitoyl-9,10-$^3$H]SM as follows: ~3.5 mCi (63 nmol) [N-palmitoyl-9,10-$^3$H]SM and 13 nmol phosphatidylcholine (PC) were mixed in chloroform, and the solvent was removed first under a stream of nitrogen and then by lyophilization. The dried lipids were resuspended in 1 ml of 150 mM NaCl, 1 mM EDTA, 10 mM Tris-HCl. pH 7.5 and, to prepare [$^3$H]SM/PC liposomes, sonicated for three 50-sec pulses at 4° C. using a tapered microtip on a Branson 450 sonicator (setting #3). The liposomes were then incubated with 30 mg (by protein mass) of LDL, 50 g of partially purified phospholipid transfer protein, 100 U penicillin, and 100 g streptomycin for 18 h at 37° C. under argon. LDL was then separated from the liposomes after phospholipid transfer by centrifuging the mixture at density=1.006 g/ml for 8 h at 35,000 rpm in a BECKMAN® 50.3 rotor; the supernate containing the liposomes was removed, and the LDL band at the bottom of the tube was harvested. The LDL solution was mixed with PBS and centrifuged as before. This wash procedure was performed a total of four times, resulting in the removal of 95% of the unreacted [$^3$H]SM/PC liposomes. All lipoproteins were stored under argon at 4° C. and were used within 2 weeks of preparation.

Control and SM-enriched LDL-lipid emulsions. Two aliquots of LDL (each 12 mg by protein mass) were extracted by the method of Bligh and Dyer (Bligh et al., 1959); 6 mg of SM was added to the lipid extract of one of the aliquots. The solvent was then completely evaporated from these samples by exposure to a stream of nitrogen, followed by lyophilization. The dried lipids were resuspended in 6 ml of PBS and sonicated under a stream of argon at 40° C. until translucent (90 min for the control emulsions and 130 min for the SM-enriched emulsions). The sonicated material was then centrifuged twice at 15,000×g, and the supernate was harvested.

Ceramide and diacyl glycerol assays. Ceramide and diacylglycerol were measured from aliquots of lipid extracts of LDL and emulsions using the method described by Schneider and Kennedy (Schneider et al., 1976) and adapted by Preiss et al. (Preiss et al., 1986). In this method, diacylglycerol (DAG) kinase phosphorylates ceramide and DAG using [$\gamma$-$^{32}$P]ATP; the contents of ceramide and DAG in the experimental samples are calculated from amount of incorporated $^{32}$P label in comparison with standard curves using known quantities of the two lipids. For ceramide measurements, the lipids were first incubated with 0.1 N KOH in methanol for 1 h at 37° C., which hydrolyzes DAG, but not ceramide. The extracted lipids were dried under nitrogen and then solubilized in 5 mM cardiolipin, 7.5% octyl-β-glucopyranoside, and 1 mM diethylenetriaminepentaacetic acid by bath sonication. This solution was then added to reaction buffer (50 mM imidazole-HCl, pH 6.6, 50 mM NaCl, 12.5 mM $MgCl_2$, 1 mM PGTA) containing sn-1,2-DAG kinase (0.7 units/ml). The reaction was initiated by the addition of [$\gamma$-$^{32}$P]ATP (final concentration=10 mM). After incubation at room temperature for 60 min, the reaction was stopped by lipid extraction with chloroform:methanol:HCl (100:100:1, v/v/v) and 10 mM EDTA. Ceramide-1-phosphate and phosphatidic acid in the organic phase were separated by TLC using chloroform:methanol:acetic acid (65:15:5, v/v/v); the Alipids were visualized with autoradiography and identified by comparing with standards. The spots corresponding to these two lipids were scraped and counted, and the masses of the lipids were calculated by comparison with standard curves, as described above.

Sphingomyelin (SM), phosphatidylcholine (PC), and cholesterol assays. Lipid extracts (20) of LDL and emulsions were chromatographed by TLC using chloroform:methanol:acetic acid:$H_2O$ (50:25:8:4, v/v/v/v). Individual phospholipid subclasses were visualized by iodine vapor staining, and the SM and PC spots were identified by comparison with standards. The spots were scraped, extracted twice with chloroform:methanol (2:1), and assayed for phosphate content by the method of Bartlett (Bartlett, 1959). Total cholesterol contents were assayed using an enzymatic colorimetric method (Cholesterol C kit, Wako Chemicals USA, Inc., Richmond, Va.) it was verified that the values obtained by this method are similar to those obtained using gas-liquid chromatography.

Isolation of LDL from human lesions. LDL was extracted from abdominal aortic aneurysm plaque material as previously described (Rapp et al., 1994). Briefly, aortic plaque was removed from individuals as part of the standard reconstructive surgery for abdominal aortic aneurysms at the San Francisco Veterans Affairs Medical Center. Plaque material, which ranged in weight from 2–12 grams, was obtained in the operating room and immediately placed into ice-cold 7-mM citrate buffer, pH 7.4, containing 15 mM NaCl, 3 mM EDTA, 0.5 mM butylhydroxytoluene, 1 mM phenylmethylsulfonylfluoride, 1.5 mg aprotinin/ml, 2 mM benzamidine, and 0.08 mg gentamycin sulfate/ml. Blood and adherent thrombus were removed by blotting with absorbent gauze, scrubbing with a small brush, and sharp dissection as necessary. Loosely retained lipoproteins were extracted by mincing the plaque into 0.5–1.0 mm$^2$ pieces and incubating them overnight on a LADQUAKE® shaker at 4° C. in a non-denaturing buffer (0.1 M citrate, pH 7.4, with 1 mg EDTA/ml, 0.3 mg benzamidine/ml, 0.08 mg gentamicin sulfate/ml, 10 µg aprotinin/ml, 10 µg Trolox [an anti-oxidant]/ml, and 20 µg phenylmethylsulfonyl fluoride/ml). The extracted material was cleared of particulate matter by centrifuging at 800×g for 10 min, and 1.019<d<1.063-g/ml lipoproteins were isolated by sequential sodium bromide density ultracentrifugation (Rapp et al., 1994; Havel et al., 1955). To extract LDL from early human lesions, the same procedure was used, except the intima and inner media were peeled away from the outer media and adventitia before being minced and processed as above.

Apolipoprotein B-100 slot immunoblot analysis. The samples to be tested were applied to a nitrocellulose membrane using a slot blot apparatus. Next, the membrane was incubated with 5% Carnation nonfat dry milk in buffer A (24 mM Tris, pH 7.4, containing 0.5 M NaCl) for 3 h at room temperature. The membrane was then incubated with rabbit anti-human apolipoprotein B-100 antiserum (1:1000) in buffer B (buffer A containing 0.1% Tween-20, 3% nonfat dry milk, and 0.1% bovine serum albumin) for 4 h at room temperature. After washing four times with buffer A containing 0.1% Tween-20, the blots were incubated with horseradish peroxidase-conjugated goat anti-rabbit IgG (1:2000) for 1 h in buffer B at room temperature. The membrane was subsequently washed twice with 0.3% Tween-20 in buffer A and twice with 0.1% Tween-20 in buffer A. Finally, the blot was soaked in the enhanced chemiluminescence reagent for 2 min and exposed to X-ray film for 1 min. For FIGS. 5A–D, the relative intensities of the slot blot signals were determined by densitometric scanning of the X-ray film using a Molecular Dynamics Computing Densitometer (model 300A) with IMAGE-QUANT® software.

Assay for LDL-SM hydrolysis by strips of rabbit aorta ex vivo. New Zealand white male rabbits (2–3 kg) were fed a chow diet containing 0.2% cholesterol and 10% soybean oil (w/w) for 18 days. The animals were sacrificed, and the thoracic aortae were removed rapidly and placed in a dissection dish with physiological Hank's Trizma maleate buffer (133 mM NaCl, 3.6 mM KCl, 1.0 mM $CaCl_2$, 5.0 mM Trizma maleate, 16 mM dextrose, pH 7.3). The aortae were then further dissected to remove excess fat and any clotted blood and then cut longitudinally and pinned, lumen side up, in a tissue culture dish. The aortic strips were washed several times with DMEM/0.2% BSA and incubated at 37° C. for 3.5 h in DMEM/0.2% BSA containing 2 mg [$^3$H]SM-labeled LDL per ml. For certain experiments, the strips were pre-incubated at 37° C. for 30 min medium alone, or supplemented with 15 mM EDTA or 200 µM chloroquine. When present, these reagents were also added to the corresponding incubation media containing labeled LDL (see legend to FIG. 5). After the 3.5-h incubation of labeled LDL with aortic strips, media were removed (see below), the aortic strips were quickly washed twice in ice-cold PBS, and the center of the strip was cut away from the original cut ends. These center pieces were then minced and extracted in PBS, pH 7.4, containing 6 M guanidine-HCl, 5 mM EDTA, 0.02% sodium azide, 35 µM leupeptin, 1.5 mg aprotinin/ml, and 5 µM pepstatin A for 36 h at 4° C. The extract was centrifuged at 35,000×g for 30 min, and lipids were extracted from the supernate by the method of Bligh and Dyer (Bligh et al., 1959). [$^3$H]palmitate-SM, $^3$[H]palmitate-ceramide, and free [$^3$H]palmitate in the lipid extracts were separated by TLC using chloroform:methanol (95:5, v/v) or n-propanol:12.5% ammonium hydroxide (80:20, v/v). For controls, [$^3$H]SM-LDL that was incubated for 3.5 h in media without aortic strips, and [$^3$H]SM-LDL that was incubated with the strips but not retained (i.e., in the media that was harvested after the incubation) were subjected to the same extraction Procedures, including the 36-h incubation in guanidine buffer.

Iodination of EGF and assay for $^{125}$I-EGF degradation. Epidermal growth factor (50 µg) was radioiodinated to a specific activity of 5400 counts/min/ng (IODOBEADS®, Pierce Chemical Co., Rockford, Ill.) and was used within 48 h of labeling. After a 3.5-h incubation with aortic strips, in the absence or presence of 200 µM chloroquine, degradation of $^{125}$I-EGF was assayed by the release of $^{125}$I-tyrosine (Golstein et al., 1983).

Statistics. Unless otherwise indicated, results are given as means±S.D. (n=3); absent error bars in the figures signify S.D. values smaller than the graphic symbols.

Results

SMase-induced aggregation of LDL in vitro requires active SMase enzyme and is mediated via high particle ceramide content. Determination of whether active SMase enzyme is required for LDL aggregation or whether the effect is purely structural was first sought; for example, lipoprotein lipase-mediated bridging of LDL to cell-surface proteoglycans is a purely structural effect of the lipase molecule. In vitro studies utilized bacterial SMases, which are a reasonable model for mammalian SMases in regard to enzymatic activity but not necessarily in regard to structural actions. Careful analysis of the time course of *B. cereus* SMase-induced LDL aggregation and LDL-SM hydrolysis was done. Whereas LDL-SM hydrolysis was 70% complete within the first 30 min of exposure to SMase (FIG. 1A, closed triangles), substantial LDL aggregation began to occur only after 30 min of incubation (FIG. 1B, open squares). These kinetics are consistent with two possible mechanisms: a slow structural action of SMase, or a rapid enzymatic action that alters the particles so that they then slowly aggregate. To distinguish between these possibilities, EDTA was used to inhibit the enzymatic activity of the bacterial B. cereus SMase, which is a $Mg^{2+}$-dependent enzyme (Ikezawa et al., 1986). As in FIG. 1A, substantial aggregation of LDL occurred in the absence of EDTA after an initial lag period (FIG. 1B, open squares). When EDTA was added at the beginning of the reaction, however, there was complete inhibition of LDL-SM hydrolysis (inset) and of LDL aggregation (open triangles). To show that EDTA is not a direct inhibitor of the aggregation process itself, EDTA was added 20 min after the SMase reaction had begun. 68% of LDL-SM was hydrolyzed under these conditions (FIG. 1C). Despite the presence of EDTA during the period of the aggregation process (i.e., following the 20-min incubation with SMase), substantial LDL aggregation still occurred (FIG. 1B, closed triangles). The degree of aggregation in this setting was consistent with the degree of LDL-SM hydrolysis under these conditions. Thus, EDTA can inhibit SMase-induced aggregation of LDL, but solely through its inhibition of SMase enzymatic activity, with no direct effects on the aggregation process itself. SMase that has been enzymatically inactivated by EDTA can no longer provoke LDL aggregation, indicating that enzymatic activity is an absolute requirement.

Next it was determined which of the three consequences of SMase enzymatic activity, namely, generation of choline-phosphate, generation of ceramide, and depletion of SM, is responsible for LDL aggregation. One of these possibilities, SM depletion, cannot be relevant to the pathogenesis of atherosclerosis: lesional LDL, which aggregates, is known to be enriched in SM compared to plasma LDL. Incubating LDL with a 10-fold molar excess of choline-phosphate was performed. This treatment failed to increase the turbidity of LDL, indicating that choline-phosphate does not mediate SMase-induced aggregation of LDL.

Work was then done to distinguish whether aggregation results from an increase in LDL-ceramide or from a low LDL-SM content. Attempts to significantly alter SM and ceramide contents of intact LDL, for example by using phospholipid transfer protein or cholesteryl ester transfer protein, proved unsuccessful (see below) Therefore, LDL lipids were used to prepare protein-free synthetic emulsions, which aggregate like native LDL after SMase treatment. Emulsions were prepared with either LDL lipids (control emulsions) or LDL lipids to which extra SM was added. Partial digestion of these emulsions with SMase was accomplished by adding EDTA to stop the reaction after only 15 min at 37° C. (see above). The control emulsion showed substantial particle aggregation (compare solid bars in first and third triplets of bars in FIG. 2). Partial enzymatic digestion of the SM-enriched emulsions generated ceramide-rich particles that still had a very high SM content (two-fold greater than in undigested control emulsions). These ceramide-rich, SM-rich particles aggregated to an even greater degree than SMase-treated control emulsions (compare sold bars in third and fourth triplets of bars in FIG. 2), presumably because they had more ceramide than the control emulsions (see below) Thus, SMase-induced aggregation readily occurs even when the residual SM content of the particles is still very high, as it is in lesional LDL (Hoff, 1983; Ylä-Herttuala et al., 1989). SM depletion cannot explain SMase-induced aggregation. These results indicate that the increase in particle ceramide is the key factor in this process. To test this relationship directly using intact LDL, plasma LDL was treated with SMase for varying times to generate particles with varying amounts of ceramide, allowed to aggregate, and then assayed for both aggregation and ceramide content. After an initial "threshold" level of ~0.08 nmol ceramide/nmol phosphatidylcholine, there was a direct relationship between LDL-ceramide content and LDL aggregation (FIG. 3).

In summary, SMase-induced aggregation of LDL is mediated by enzymatic, not structural, actions of the SMase, and the key factor in causing aggregation is an increase in particle ceramide content, not a low absolute SM content. Both of these findings are consistent with the hypothesis that an arterial-wall SMase may contribute to the aggregation of lesional LDL. Note also that particle aggregation does not depend on apoB.

Human atheroma-derived LDL is enriched in ceramide. The finding that LDL-ceramide content is the key factor in SMase-induced aggregation led to an examination of the ceramide content of human lesional LDL. For these experiments, material was obtained from two types of human lesions: atherectomy material (advanced atherosclerosis and human aorta with only fatty streak involvement (early atherosclerosis). Tissue specimens were extracted overnight at 4° C. in a non-denaturing aqueous buffer, and 1.019<d<1.063-g/ml lipoproteins were isolated from the extraction buffer by sequential ultracentrifugation as previously reported (Rapp et al., 1994).

Figure 4D:
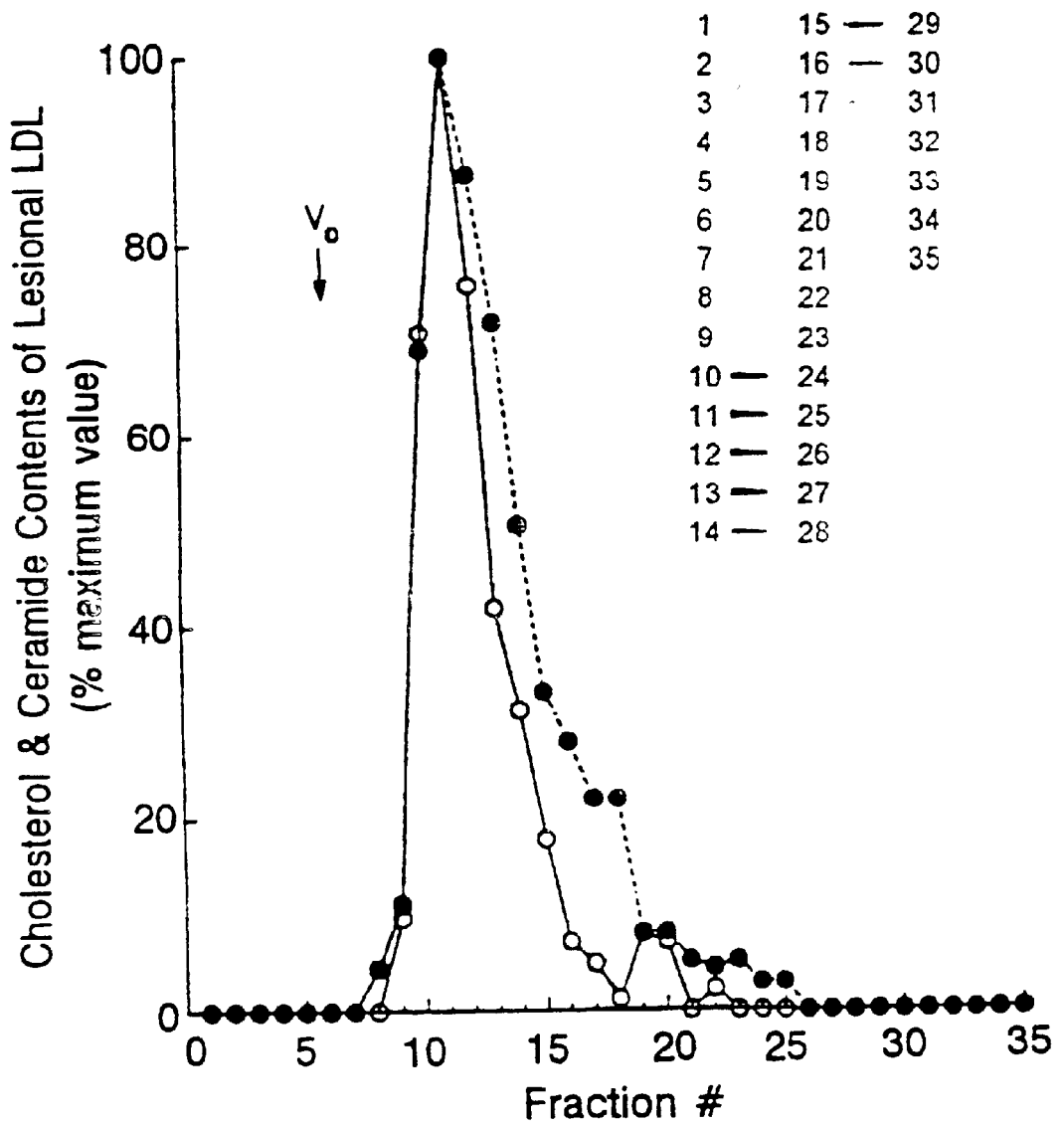

Three separate experiments, analyzing the ceramide contents of lesional material from five different atherectomy samples altogether, are shown in FIGS. 4A–C. Same-donor plasma LDL was available for comparison with Lesion LDL #1, #3, and #5; Lesion LDL #2 and #4 were compared with two different samples of plasma LDL prepared from plasma (labeled Plasma LDL A and Plasma LDL B in FIG. 4). Remarkably, the samples of lesional LDL had a ceramide content that was 10–50-fold higher than that of plasma LDL, which was always ceramide-poor. Further characterization of the lipids in lesional LDL by HPLC confirmed the presence of ceramide, with only trace amounts of the biosynthetic intermediate, dihydroceramide (see Merrill et al., 1990). To verify that the extraction procedure did not cause artifactual hydrolysis of LDL-SM, it was shown that [$^3$H] SM-labeled LDL added to extraction buffer with an unlabeled arterial sample was not hydrolyzed during extraction or sequential ultracentrifugation (0.006+/−0.002 percent of the radioactivity in the original preparation of [$^3$H]SM-LDL co-migrated with ceramide on TLC, and this fraction remained exactly the same in [$^3$H]SM-LDL subjected to the extraction procedure). To show that the ceramide was in LDL, Lesion LDL #1 was fractionated using a Superose-6 gel-filtration column (molecular weight exclusion=$4\times10^6$), a commonly used chromatographic technique for separating lipoprotein classes. Note that the column was run in buffer containing 6 M guanidine-HCl to partially dissociate large LDL aggregates (Hoff et al., 1985; and below), which otherwise might not enter the column or elute in the void volume, and thus not be separated from lesional debris. As shown in FIG. 4D, cholesterol, ceramide, and apolipoprotein B-100 (inset) co-eluted within the included volume of the column. Finally, to determine if there had been generalized break-down of phospholipids in LDL from advanced lesions, we assayed Lesion and Plasma LDL #3 for DAG, which is a product of phosphatidylcholine hydrolysis by phospholipase C. Whereas the ceramide content of the lesional LDL was 54 pmol/nmol PC (FIG. 4B), the DAG content of this material, as well as of the sample of plasma LDL, was below the detection limit of the assay (<2 pmol/nmol PC). These data indicate specific hydrolysis of SM in lesional LDL and no evidence of a significant role for phospholipase C in vivo (cf. Suits et al., 1989).

To examine LDL from early human lesions, the same extraction procedure was used to obtain LDL from a segment of aorta from a 43-y/o male donor heart. Gross examination of this aortic segment revealed only fatty streaks, without any raised lesions. The ceramide content of the lesional LDL was 0.031±0.002 nmol/nmol PC, whereas same-donor plasma LDL had only 0.013±0.005 nmol ceramide/nmol PC. Thus, even in relatively early atherosclerosis, lesional LDL is 2–3-fold enriched in ceramide compared with plasma LDL.

Figure 5B:
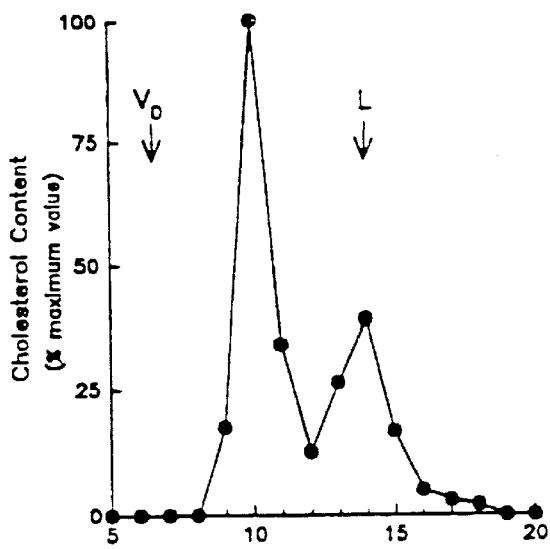
Figure 5C:
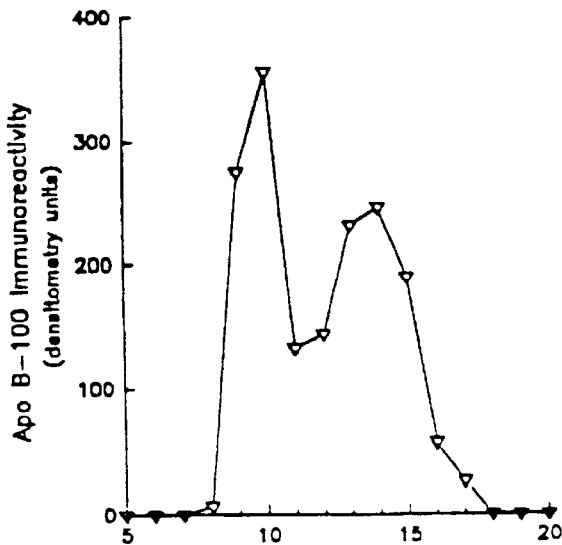
Figure 5D:
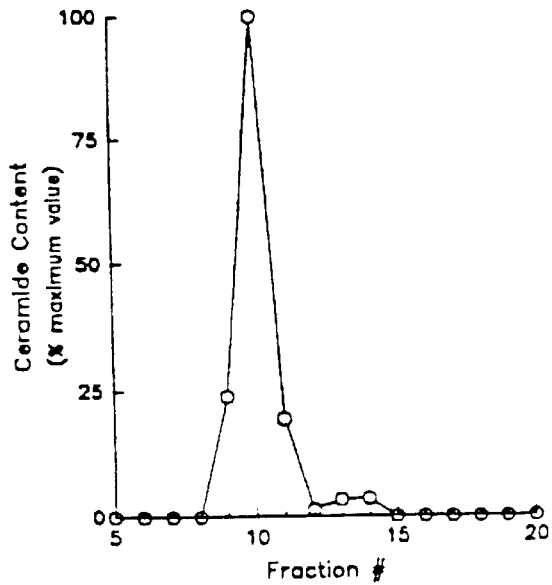

Only aggregated lesional LDL is enriched in ceramide. Lesion LDL #5 from FIG. 4 was characterized for aggregation using centrifugation and gel-filtration chromatography, as described previously (Lougheed et al., 1996). As shown in FIG. 5A, approximately 60% of the lesional LDL-cholesterol pelleted during a brief centrifugation (10 min at 10,000×g), indicating the presence of apparently very large aggregates. This pelleted material contained ceramide (FIG. 5A), consistent with a role for ceramide in LDL aggregation. To determine whether the ceramide in the 10,000×g supernate (FIG. 5A) was also associated with aggregates of LDL, this material was fractionated by gel-filtration chromatography using SUPEROSE® 6 as in FIG. 4, but in the absence of guanidine-HCl (FIG. 5B–D). The column was calibrated with plasma LDL, which eluted in a sharp peak centered around fraction #14 based on cholesterol and apo B-100 immunoreactivity (L in FIG. 5B). The data that the cholesterol (FIG. 5B) and apo B-100 (FIG. 5C) of the 10,000×g supernate eluted in two peaks. The second peak, which contained approximately 40% of the cholesterol and 50% of the apo B-100, eluted in the position of plasma LDL, indicating unaggregated material. The first peak eluted four fractions earlier, indicating aggregation. Essentially all of the ceramide was associated with the first peak of lesional LDL (FIG. 5D). Thus, lesional LDL exists in three forms: apparently very large aggregates, smaller aggregates, and particles that behave like unaggregated LDL. Importantly, ceramide is present only in the aggregated forms of lesional LDL.

LDL-SM hydrolysis by the arterial wall. Enrichment of lesional LDL with ceramide could occur through two processes: hydrolysis of LDL-SM or transfer of pre-existing ceramide from cells or cellular debris onto the LDL particles. To examine ceramide transfer, enrichment of LDL was attempted in vitro by incubation with suspensions of ceramide or with sonicated emulsions containing ceramide. Even in the presence of phospholipid transfer protein or cholesteryl ester transfer protein, however, unable to incorporate pre-existing ceramide into LDL. The only method found to enrich LDL with ceramide in vitro was by digestion of the lipoprotein with SMase (see FIGS. 1–3). These data indicate that ceramide transfers poorly, if at all, and that this mechanism is unlikely to explain the lipid composition of lesional LDL.

To directly examine LDL-SM hydrolysis in arteries, strips of rabbit aorta were incubated with [$^3$H]palmitate-SM-labeled LDL for 3.5 h at 37° C. and then extracted the retained LDL in guanidine buffer to look for evidence of [$^3$H]ceramide generation (cf. Nievelstein-Post et al., 1994). Histologic analysis of thin sections of the vessel strips after the 3.5-h incubation showed no cellular damage when compared to freshly fixed vessels. The data from two separate experiments are shown in FIG. 6A. In both experiments, material extracted from the aortic strips had markedly increased [$^3$H]ceramide compared with unretained [$^3$H]SM-LDL or with [$^3$H]SM-LDL incubated for 3.5 h in media without aortic strips (compare third pair of bars in FIG. 6A with the first two pairs of bars). To determine whether the extraction procedure itself caused artifactual hydrolysis of LDL-SM, this procedure was performed using [$^3$H]SM-LDL added to extraction buffer in the presence of minced pieces of aortic strips that had not been incubated previously with [$^3$H]SM-LDL. Under these conditions, there was no hydrolysis of [$^3$H]SM-LDL. Thus, the data in FIG. 6A indicate hydrolysis of LDL-SM within the arterial wall.

At least four different SMases have been shown to be present in mammalian cells. Two of these are encoded by the acid SMase gene and arise by differential post-translational processing (Schissel et al., 1996). One of these acid SMase gene products is located in lysosomes (lysosomal SMase), does not require added cations, and is not inhibited by EDTA (Spence, 1993). The other SMase derived from the acid SMase gene is secreted by a wide variety of cell types (Schissel et al., 1996) and requires exogenous $Zn^{2+}$ for activity (Schissel et al., 1996; Spence et al., 1989). In addition, cells have a membrane-bound neutral SMase that requires $Mg^{2+}$ for activity (Chatterjee, 1993) as well as a cytoplasmic neutral SMase that is cation-independent (Okazaki et al., 1994). Thus, two of the four known mammalian SMases require a divalent cation. To determine if aortic hydrolysis of LDL-SM requires divalent cations, portions of the aortic strips from the two experiments in FIG. 6A were preincubated with 15 mM EDTA and then incubated with the [$^3$H]SM-LDL plus EDTA. As shown in the last doublet of bars in FIG. 6A, EDTA treatment decreased the generation of ceramide in the extracted material by approximately 50%. These data indicate that at least a portion of the arterial-wall SMase activity that hydrolyzes retained [$^3$H]SM-LDL requires divalent cations.

The overall hypothesis assumes that LDL-SM is hydrolyzed extracellularly, not intracellularly in lysosomes. The fact that a substantial portion of the arterial-wall SMase acting on retained LDL is inhibited by EDTA (FIG. 6A) indicates that much of the LDL-SM is not being hydrolyzed by lysosomal SMase, which is EDTA-resistant (see above). Furthermore, the [$^3$H]palmitate-SM-labeled LDL that was retained in the aortic strips showed no enrichment in free [$^3$H]palmitate, thereby suggesting no contact of the particle with lysosomal ceramidase (Bernardo et al., 1995). To further assess the contribution of lysosomes, a set of experiments was conducted in which 200 μM chloroquine, an inhibitor of lysosomal hydrolases (Goldstein et al., 1977), was included in the aortic strip assay. Two preliminary studies were done to validate this strategy. First, cultured human fibroblasts were incubated in the presence of 50 μM chloroquine and found that cellular hydrolysis of [$^3$H]SM-LDL was inhibited by 73% compared with that seen with untreated fibroblasts (data no, shown); this finding indicates that chloroquine does indeed block the hydrolysis of LDL-SM by lysosomal SMase. Second, the ability of chloroquine to work in the aortic strip assay was tested. For this study, $^{125}$I-labeled epidermal growth factor ($^{125}$I-EGF) was used, which is known to be internalized by receptor-mediated endocytosis and degraded in lysosomes in many cell types (Goldstein et al., 1985). Aortic strips were pre-incubated at 37° C. for 30 min in medium without (control) or with 200 μM chloroquine. $^{125}$I-EGF was added, then incubated with these strips for 3.5 h. It was found that chloroquine blocked the degradation of $^{125}$I-EGF by 50%, indicating substantial inhibition of lysosomal hydrolases in the aortic strips. Next, an examination of the effects of 200 μM chloroquine on LDL-SM hydrolysis by aortic strips was done. As before, retained material, but not unretained [$^3$H]SM-LDL, was enriched in [$^3$H]ceramide (FIG. 6B: compare the first with the second pair of bars). When chloroquine was added in the same manner as in the $^{125}$I-EGF experiment, no substantial inhibition of [$^3$H]ceramide enrichment of the retained material was seen (third pair of bars in panel B) In summary, these data indicate that SM delivered into the arterial wall on LDL is hydrolyzed by a non-lysosomal arterial SMase that is at least partially dependent on divalent cations.

Discussion

In light of the in-vitro observation that SMase treatment of LDL leads to lipoprotein aggregation (Xu et al., 1991), an important atherogenic event (Nievelstein et al., 1991; Hoff et al., 1985; Guyton et al., 1996; and Tabas et al., 1993), the overall goal of the present study was to seek evidence for an arterial-wall SMase acting on LDL retained in vivo. In this regard, it has been shown that the mechanism of bacterial SMase-induced aggregation of LDL in vitro is consistent with a similar process occurring with mammalian SMases in the subendothelium (FIGS. 1–3), and direct evidence has been provided that an arterial-wall SMase activity hydrolyzes the SM of retained LDL (FIGS. 4–6) Most remarkably, all the samples of lesional LDL that were examined were 10–50-fold enriched in ceramide compared with plasma LDL (FIG. 4). Although it has not been proven that the ceramide in these samples is enough to cause aggregation (compare with FIG. 3), only the aggregated forms of lesional LDL are enriched in ceramide (FIG. 5). Moreover, one could easily imagine that other factors in lesions, such as proteoglycans, collagen, or lipoprotein lipase (Williams et al., 1995; Camejo et al., '993; and Goldberg, 1996), could lower the "threshold" for ceramide-induced LDL aggregation in vivo. In a similar manner, ceramide enrichment of LDL could lower the aggregation threshold for other possible inducers of aggregation, such as oxidation (Hoff et al. 1989) or other lipases (Suits et al., 1989). It is also possible that the most ceramide-rich and aggregated lipoproteins would have already been rapidly ingested and degraded by lesional macrophages and thus would not have been present at the time of the extractions.

The mechanism and regulation of ceramide-induced aggregation represents an important area requiring further investigation. The mechanism of aggregation may be related to the membrane-disruptive and possibly "fusogenic" properties of ceramide (van Meer, 1993; Skiba et al., 1996) or to hydrogen bonding between ceramide and surface phospholipids of neighboring particles (Xu et al., 1991). Clearly, the mechanism does not require apolipoproteins, since SMase induces aggregation of protein-free emulsions (FIG. 2), though the initial retention to arterial proteoglycans (Camejo et al., 1993) or collagen (Bowness et al., 1989) or the interaction with lipoprotein lipase (Goldberg, 1996) in vivo presumably does require apolipoprotein B. Moreover, other apolipoproteins, such as apolipoprotein AI, may prevent lipoprotein aggregation (Khoo et al., 1990); in fact, it was found that SMase-induced aggregation of LDL is completely blocked by free apo AI or apo AI-containing HDL$_3$ when added to LDL at a apo AI:apo B-100 molar ratio of 0.5$^3$. In this regard, the potent anti-atherogenic effect of apo AI and HDL$_3$ in humans (Tall, 1990) and in apo AI-transgenic mice (Rubin et al., 1991) may be partially mediated by inhibition of subendothelial lipoprotein aggregation.

The data indicate that at least a portion of the arterial-wall SMase activity is divalent cation-dependent (FIG. 6A). As described in the Results section, two known mammalian SMases have this property: a membrane-bound, neutral, Mg$^{2+}$-dependent SMase and a secreted Zn$^{2+}$-dependent enzyme. In one report examining neuronal cells, the Mg$^{2+}$-dependent SMase was shown to be externally oriented (Mohan Das et al., 1984); a similar orientation on arterial-wall cells could result in the hydrolysis of extracellularly retained lipoproteins. Homogenates of non-lesional rabbit aortic intima have a neutral, Mg$^{2+}$-dependent SMase activity (see Spence et al., 1979) that can act on LDL-SM in vitro, but no direct evidence exists thus far that this enzyme is in the proper orientation to hydrolyze LDL retained in the subendothelium in vivo. The Zn$^{2+}$-dependent secreted SMase has been found to be secreted by several arterial-wall cell types, including macrophages (Schissel et al., 1996) and endothelial cells[2]. Although Zn-SMase has an acidic pH optimum using an SM-micelle substrate (Schissel et al., 1996; Spence et al., 1989), this enzyme activity in macrophage-conditioned medium can hydrolyze LDL-SM at neutral pH in the presence of lipoprotein lipase[3], an arterial-wall enzyme known to be present in atherosclerotic lesions (Ylä-Herttuala et al., 1991; Jonasson et al., 1987). The secreted Zn-dependent SMase, acting in co-operation with lipoprotein lipase, and perhaps externally oriented Mg$^{2+}$-dependent SMase, may be important in subendothelial lipoprotein aggregation. The most direct test of these hypotheses will first require further molecular characterization of these and possibly other arterial-wall SMases, followed by inhibition of these activities in animal models by genetic or pharmacologic means.

Finally, the data herein may have implications beyond the realm of subendothelial lipoprotein aggregation. Exposure of cells to SMase has been shown to induce inflammatory or apoptotic changes, both of which are known to occur in atherosclerosis (Libby et al, 1991; Geng et al., 1995; Han et al. 1995), via ceramide-induced signaling pathways (Kolesnick, 1991; Hannun et al., 1989). Furthermore, treatment of macrophages with SMase increases the potency of atherogenic lipoproteins to stimulate the cholesterol esterification pathway (Okwu et al., 1994). Thus, the same SMase activity that was shown to hydrolyze extracellular, retained LDL-SM might also hydrolyze cellular SM, which is known to be concentrated in the external leaflet of the plasma membrane (Merrill et al., 1990). Furthermore, it is possible that when cells, particularly macrophages, ingest large amounts of ceramide-rich lesional LDL, some of the ceramide escapes lysosomal hydrolysis and enters the signalling pathway. As with the aggregation hypothesis, these ideas will be best tested by using experimental systems with altered arterial-wall SMase activity.

Footnotes

1. Abbreviations used: apc, apolipoprotein; DMEM, Dulbecco's modified Eagle's medium; BSA, bovine serum albumin; EGF, epidermal growth factor; LDL, low-density lipoprotein; PBS, phosphate-buffered saline; PC, phosphatidylcholine; SM, sphingomyelin; SMase, sphingomyelinase; TLC, thin-layer chromatography.

2. The term "aggregation" is used to designate self-associated LDL due to either adherence of individual particles or fusion.

EXAMPLE 2

The Sphingomyelin of Atherogenic Lipoproteins is Hydrolyzed by Mammalian Secreted Sphingomyelinase A Potential Role for Secreted Sphingomyelinase in the Subendothelial Retention and Aggregation of Atherogenic Lipoproteins The subendothelial aggregation and retention of low-density lipoprotein (LDL) are key events in atherogenesis, but the mechanisms in vivo are not known. Treatment of LDL with bacterial sphingomyelinase (SMase) in vitro leads to the formation of lesion-like LDL aggregates that become retained on extracellular matrix and stimulate macrophage foam cell formation. In addition, LDL retained in human atherosclerotic lesions shows evidence of hydrolysis by an arterial-wall SMase in vivo, and several arterial-wall cell types secrete a zinc-activated SMase (S-SMase) S-SMase however, has a sharp acid pH optimum using a standard in vitro SM-micelle assay and its ability to act on lipoprotein-SM, particularly at neutral pH, is unknown It is shown herein that S-SMase can hydrolyze and aggregate native plasma LDL at pH 5.5, but not at pH 7.4. LDL modified by oxidation, treatment with phospholipase $A_2$, or enrichment with apolipoprotein CIII is hydrolyzed readily by S-SMase at pH 7.4. In addition, lipoproteins from the plasma of apolipoprotein E knockout mice, which develop extensive atherosclerosis, are highly susceptible to hydrolysis and aggregation by S-SMase at pH 7.4; a high SM:PC ratio in these lipoproteins appears to be an important factor in their susceptibility to S-SMase. Most importantly, LDL extracted from human atherosclerotic lesions, which is enriched three-fold in sphingomyelin compared to plasma LDL, is hydrolyzed by S-SMase at pH 7.4 ten-fold more than same-donor plasma LDL, suggesting that LDL is modified in the arterial wall to increase its susceptibility to S-SMase. In summary, S-SMase can hydrolyze and aggregate LDL in vitro, making it a leading candidate for the arterial-wall SMase that hydrolyzes LDL-SM and causes subendothelial LDL aggregation.

A critical event in early atherogenesis is the subendothelial retention of atherogenic lipoproteins, including LDL[1] (Schwenke et al., 1989; Nievelstein et al., 1991), lipoprotein (a) [Lp(a)] (Kreuzer et al., 1994), and triglyceride-rich lipoproteins (Rapp et al., 1994). Retained lipoproteins likely trigger a series of biological responses, such as endothelial changes and recruitment of macrophages to the arterial wall, that are central to the initiation and progression of atherosclerosis (Williams et al., 1995).

Subendothelial lipoproteins are exposed to several modifying enzymes, including lipases (Ylä-Herttuala et al., 1991; Schissel et al., 1996; Hurt-Camejo et al. 1997), oxidizing enzymes (Leeuwenburgh et al., 1997), and proteases (Kaartinen et al., 1994). The actions of these and other unknown factors lead to the several prominent lipoprotein modifications observed in vivo including oxidation (Ylä-Hettuala et al., 1989), enrichment with the phospholipid sphingomyelin (SM) (Ylä-Hettuala et al., 1989; Daugherty et al., 1988; Hoff, 1983), and self-aggregation (Neivelstein et as., 1991; Hoff et al., 1985, Guyton et al., 1996). Lipoprotein aggregation is likely to be important in atherogenesis for at least two reasons. First, processes that promote lipoprotein aggregation before or during retention dramatically increase the amount of lipoprotein retained (Tabas et al., 1993). Second, aggregated LDL, but not unaggregated LDL, is a potent inducer of macrophage foam cell formation (Hoff et al, 1990; Khoo et al., 1988; Suits et al., 1989; and Xu et al., 1991).

While the mechanism of lipoprotein aggregation in lesions has not yet been elucidated, several studies as described herein suggest that the enzyme sphingomyelinase (SMase) may be an important mediator of lipoprotein aggregation in vivo. First, LDL treated with bacterial SMase forms lesion-like self-aggregates (Xu et al., 1991) due to enrichment in ceramide (Schissel et al., 1996), the major product of SM hydrolysis; furthermore, these aggregates potently induce macrophage foam cell formation in vitro (Tabas et al., 1993; Xu et al., 1991). Second, aggregated LDL from human atherosclerotic lesions shows evidence of hydrolysis by an extracellular SMase, and LDL retained in rabbit aortic strips ex vivo is hydrolyzed by an extracellular, cation-dependent SMase (Schissel et al., 1996). Third, and most important, several cell types present in atherosclerotic lesions, namely endothelial cells and macrophages (Schissel et al., 1996), secrete a $Zn^{2+}$-activated SMase (S-SMase).

The cellular origins, secretion, and cation dependency make S-SMase a leading candidate for the arterial-wall SMase that acts on retained lipoproteins. Nonetheless, two major issues regarding the relevance of S-SMase to atherogenesis needed to be addressed. First, mammalian SMases are much more selective than bacterial SMases in terms of the milieu n which the SM is presented to the enzyme (Spence, 1993). Second, studies on the molecular origin of S-SMase have revealed that it is a product of the same gene, the acid SMase (ASM) gene, that gives rise to lysosomal SMase (L-SMase) (Schissel et al., 1996). Therefore, S-SMase shares with L-SMase a sharp acid pH optimum when assayed under standard in-vitro conditions using detergent-solubilized SM micelles as a substrate (Schissel et al., 1996; Spence et al., 1989). While it is possible that acidic enzymes are active in advanced atherosclerotic lesions, where local pockets of acidity may occur (Menkin, 1934; Smith, 1979; Maroudas et al., 1988, Tapper et al., 1992; Silver et al., 1988), a role for such enzymes in pre-lesional or early lesional events would require activity at neutral pH with physiologic substrates.

In this context, the goal of the current study was to test whether S-SMase can hydrolyze LDL-SM, particularly at neutral pH. Herein, it is shown that S-SMase can hydrolyze and aggregate native LDL at acid but not neutral pH. LDL modified by several means that have been shown to occur or might occur during atherogenesis, however, is an excellent substrate for S-SMase at pH 7.4. Most importantly, LDL extracted from human atherosclerotic lesions is efficiently hydrolyzed by S-SMase at neutral pH, suggesting that LDL is modified in the arterial wall to increase its susceptibility to S-SMase. The results support a role for S-SMase in the subendothelial hydrolysis of LDL-SM, perhaps leading to lipoprotein aggregation and lesion initiation and progression.

Methods

Materials. sn-1,2-diacylglycerol kinase (from *Escherichia coli*) was purchased from CALBIOCHEM® (San Diego, Calif.). Cardiolipin and 1,2-dioleoyl glycerol were purchased from Avanti Polar Lipids Alabaster, Ala.). [9,10-$^3$H] palmitic acid and [γ-$^{32}$P]ATP, and were obtained from DUPONT-NEW ENGLAND NUCLEAR® (Boston, Mass.). Tissue culture media and reagents were purchased from LIFE TECHNOLOGIES® (Baltimore, Md.) and fetal bovine serum was from GEMINI BIOPRODUCTS® (Calabasas, Calif.). Human native apo CIII was prepared as described (Clavey et al., 1995). Human recombinant non-pancreatic soluble PLA2 (sPLA$_2$) was purified as previously described (Sartipy et al., 1996). Partially purified phospholipid transfer protein was prepared as previously described (Tollefson et al., 1988). Soybean lipoxygenase and all other reagents were from SIGMA® (St. Louis, Mo.).

Mice. LDL receptor deficient (LDLr0) (Ishibashi et al., 1993) and apolipoprotein E deficient (E0) mice (Plump et al., 1992; Zhang et al., 1992) were purchased from Jackson Laboratories and crossed into the C57BL/6J background. LDL receptor-deficient mice expressing a human apo CIII transgene (LDLr0/CIII) were derived as previously described (Masucci-Magoulas et al., 1997).

Lipoprotein Isolation and Modification. Human and murine LDL (density, 1.020–1.063 g/mL) were isolated from fresh plasma by preparative ultracentrifugation as previously described (Havel et al., 1955). LDL (5 mg/mL) was oxidized by dialysis against 150 mM NaCl, 6 μM FeSO4, 0.04% azide for 36 h at room temperature followed by addition of EDTA (1 mM) and BHT (150 μM) and then dialysis against 150 mM NaCl, 0.3 mM EDTA (Watson et al., 1995). Alternatively, LDL (1 mg) was incubated with 275 U soybean lipoxygenase/mL and 60 μg linoleic acid/mL in 50 mM Tris-HCl pH 7.4, 0.04% azide for 24 h at 37° C. (Dzeletovic et al., 1995); LDL was re-isolated using a G-200 gel filtration column and then concentrated using a Centricon 30 (molecular weight cut-off=30,000) ultrafiltration device. LDL was treated with sPLA$_2$ as previously described (Sartipy et al., 1996). Briefly, LDL (5 mg/mL) was incubated with 15 μg pure human recombinant sPLA$_2$/mL in 0.12 M Tris-HCl pH 8.0, 12 mM CaCl$_2$, 0.1 mM EDTA, 10 μM BHT for 14 h at 37° C.; LDL (50 μg protein) was then treated directly with S-SMase as described below. Acetyl-LDL was prepared by acetylation of LDL with acetic anhydride as described previously (Goldstein et al., 1979).

Isolation of LDL from human lesions. LDL was extracted from abdominal aortic aneurysm plaque material as previously described (Rapp et al., 1994). Briefly, aortic plaque was removed from individuals as part of the standard reconstructive surgery for abdominal aortic aneurysms at the San Francisco Veterans Affairs Medical Center. Plaque material, which ranged in weight from 2–12 grams, was obtained in the operating room and immediately placed into ice-cold 7-mM citrate buffer, pH 7.4, containing 15 mM NaCl, 3 mM EDTA, 0.5 mM butylhydroxytoluene, 1 mM phenylmethylsulfonylfluoride, 1.5 mg aprotinin/mL, 2 mM benzamidine, and 0.08 mg gentamycin sulfate/mL. Blood and adherent thrombus were removed by blotting with absorbent gauze, scrubbing with a small brush, and sharp dissection as necessary. Loosely retained lipoproteins were extracted by mincing the plaque into 0.5–1.0 mm$^2$ pieces and incubating them overnight on a Labquake shaker at 4° C. in a non-denaturing buffer (0.1 M citrate, pH 7.4, with 1 mg EDTA/mL, 0.3 mg benzamidine/mL, 0.08 mg gentamicin sulfate/mL, 10 μg aprotinin/mL, 10 μg Trolox [an anti-oxidant]/mL, and 20 μg phenylmethylsulfonyl fluoride/mL). The extracted material was cleared of particulate matter by centrifuging at 800×g for 10 min, and 1.019<d<1.063-g/mL lipoproteins were isolated by sequential sodium bromide density ultracentrifugation (Rapp et al., 1994; Havel et al., 1955).

Synthesis of [$^3$H]SM. (N-palmitoyl-9,10-$^3$H]SM was synthesized as previously described (Schissel et al., 1996; Sripada et al., 1987; Ahmad et al., 1986). [9,10-$^3$H]palmitic acid (25 mCi, 450 nmol) was stirred for 12 h at room temperature with an equimolar equivalent of (N)-hydroxysuccinimide and with 3-molar equivalents of 1,3-dicyclohexylcarbodiimide in (N,N)-dimethylformamide. The reaction was run under dry argon in the dark. Sphingosylphosphorylcholine (300 nmol) and (N,N)-diisopropylethylamine (10 μl) were then added and the reaction was stirred another 12 h at room temperature. The reaction was stopped by evaporating the (N,N)-dimethylformamide under a stream of N$_2$. [N-palmitoyl-9,10-$^3$H]SM was purified by preparative thin-layer chromatography of the reaction products three consecutive times in chloroform:methanol (95:5) and then twice in chloroform:methanol:acetic acid:water (50:25:8:4). Greater than 95% of the [N-palmitoyl-9,10-$^3$H]SM was converted to [N-palmitoyl-9,10-$^3$H]ceramide after treatment with 10 mU SMase/mL (*Bacillus cereus*) for 1 h at 37° C., as assayed by TLC, indicating a pure, functional substrate.

[$^3$H]SM-labeling of LDL. Plasma LDL was labeled with [N-palmitoyl-9,10-$^3$H]SM as previously described (Schissel et al., 1996). Briefly, ~3.5 mCi (63 nmol) [N-palmitoyl-9,10-$^3$H]SM and 13 nmol phosphatidylcholine (PC) were mixed in chloroform, and the solvent was removed first under a stream of nitrogen and then by lyophilization. The dried lipids were resuspended in 1 mL of 150 mM NaCl, 1 mM EDTA, 10 mM Tris-HCl, pH 7.5 and, to prepare [$^3$H]SM/PC liposomes, sonicated for three 50-sec pulses at 4° C. using a tapered microtip on a BRANSON® 450 sonicator (setting #3). The liposomes were then incubated with 30 mg (by protein mass) of LDL, 50 μg of partially purified phospholipid transfer protein, 100 U penicillin, and 100 μg streptomycin for 18 h at 37° C. under argon. LDL was then separated from the liposomes after phospholipid transfer by centrifuging the mixture at density=1.006 g/mL for 8 h at 35,000 rpm in a BECKMAN® 50.3 rotor; the supernate containing the liposomes was removed, and the LDL band at the bottom of the cube was harvested. The LDL solution was mixed with buffer containing 150 mM NaCl, 0.3 mM EDTA pH 7.4 and centrifuged as before. This wash procedure was performed a total of four times, resulting in the removal of 95% of the unreacted [$^3$H]SM/PC liposomes. All lipoproteins were stored under argon at 4° C. and were used within 2 weeks of preparation.

[$^3$H]SM-emulsions. [$^3$H]SM-emulsions with a lipid composition similar to human LDL were prepared as follows: 5.4 mg cholesteryl oleate, 0.48 mg triolein, 1.08 mg free cholesterol, 2.04 mg phosphatidylcholine, 0.96 mg sphingomyelin, and 50 μCi [N-palmitoyl-9,10$^{-3}$H] sphingomyelin were all added in chloroform to a sonication vial and the solvent completely evaporated by exposure to a stream of nitrogen, followed by the high vacuum of a lyophilizer. The dried lipids were resuspended in 3 mL of buffer containing 150 mM NaCl, 0.3 mM EDTA pH 7.4 and sonicated under a stream of argon at 40° C. until translucent (approximately 90 min) The sonicated material was then centrifuged twice at 15,000×g to pellet any titanium shed from the sonication probe. SM-rich emulsions were prepared exactly as above except that 1.2 mg of phosphatidylcholine and 1.8 mg of SM were used, and sonication time was increased to 120 min. [$^3$H]SM-emulsions were enriched with apo CIII based on the method of Ahmad et al. (Ahmad et al., 1986). Briefly, [$^3$H]SM-emulsions (0.4 mL; 182 nmol SM) were incubated with 200 μg apo CIII (22.5 nmol) for 2 h at 40° C. A portion of the emulsions were re-isolated from free ape CIII using ultrafiltration (Clavey et al., 1995) as follows: the crude emulsion-apo CIII mixture was diluted to 2 mL with buffer containing 150 mM NaCl, 0.3 mM EDTA pH 7.4 and ultra filtered and concentrated to 0.2 mL using a CENTRICON® 30 (molecular weight cut-off=30,000); the concentrated emulsions were then diluted to 2 mL and the process was repeated 5 times. [$^3$H]SM-emulsions run through the same enrichment and re-isolation protocols in the absence of apo CIII served as the control for the experiments in FIG. 11A.

Ceramide assay. Ceramide was measured from LDL lipid extracts using the method described by Schneider and Kennedy (Schneider et al., 1976) and adapted by Preiss et al. (Preiss et al., 1986). In this method, diacylglycerol (DAG) kinase phosphorylates ceramide and DAG using [γ-$^{32}$P]ATP. For ceramide measurement, the lipids were first incubated with 0.1 N KOH in methanol for 1 h at 37° C., which hydrolyzes DAG, but not ceramide. The extracted lipids were dried under nitrogen and then solubilized in 5 mM cardiolipin, 7.5% octyl-γ-glucopyranoside, and 1 mM diethylenetriaminepentaacetic acid by bath sonication. This solution was then added to reaction buffer (50 mM imidazole-HCl, pH 6.6, 50 mM NaCl, 12.5 mM $MgCl_2$, 1 mM EGTA) containing sn-1,2-DAG kinase (0.7 units/mL). The reaction was initiated by the addition of [γ-$^{32}$P]ATP (final concentration=10 mM). After incubation at room temperature for 60 min, the reaction was stopped by lipid extraction with chloroform:methanol:HCl (100:100:1, v/v/v) and 10 mM EDTA. Ceramide-1-$^{32}$P]phosphate in the organic phase was separated by TLC using chloroform:methanol:acetic acid (65:15:5, v/v/v) and visualized with autoradiography and identified by comparing with standards. The spots corresponding to ceramide-1-[$^{32}$P]phosphate were scraped and counted, and the mass calculated by comparison with a ceramide standard curve.

Sphingomyelin (SM) and phosphatidylcholine (PC) assays. Lipid extracts (Bligh et al., 1959) of lipoproteins were chromatographed by TLC using chloroform:methanol:acetic acid:$H_2O$ (50:25:8:4, v/v/v/v). Individual phospholipid subclasses were visualized by iodine vapor staining, and the SM and PC spots were identified by comparison with standards. The spots were scraped, extracted twice with chloroform:methanol (2:1), and assayed for phosphate content by the method of Bartlett (Bartlett, 1959).

LDL Oxidation Assays. LDL lipid peroxides were measured using the method of El-Saadani et al. (El-Saadani et al., 1989). LDL (50–150 μg protein), in a volume of no more than 100 μL, was added to 1 mL color reagent [0.2 M $KH_2PO_4$, 0.12 M KI, 0.15 mM $NaN_3$, 2 g Triton-X-100/L, 0.1 g benzalkonium chloride/L, 10 μM ammonium molybdate, 20 μM BHT, 25 μM EDTA pH 6.2] and incubated in the dark for 30 min at room temperature; light absorbance at 365 nm was then measured and lipid peroxides were quantified by comparison with a $H_2O_2$ standard curve. Thiobarbituric acid-reactive substances (TBARS) were measured using a standard method (Puhl et al., 1994). Briefly, LDL (100 μL, 100–200 μg protein), was mixed with 1 mL 20% trichloroacetic acid and incubated on ice for 30 min. Following precipitation, 1 mL 1% thiobarbituric acid was added and the samples heated at 95° C. for 45 min. After cooling, the samples were centrifuged at 1000×g for 20 min. and the light absorbance at 532 nm was measured. TBARS were quantified by comparison with a malonaldehyde standard curve prepared using tetramethoxypropane. LDL electrophoretic mobility was assayed by loading 30 μg of LDL protein onto a polyacrylamide 0.75%–27% gradient gel (Lipogel; Zaxis, Hudson Ohio) and electrophoresing in 0.1 M Tris-base, 0.1 M boric acid, 20 mM EDTA (upper chamber=pH 8.7; lower chamber=pH 8.3) for 12 h at 100 V. The gel was then stained with sudan black and the bands visualized by counter-staining with methanol:acetic acid::water (10:7:83 v/v/v).

S-SMase. The source of S-SMase was serum-free conditioned medium from DG44 CHO cells stably transfected with the human acid SMase cDNA (Schissel et al., 1996; Schuchman et al., 1991). It was demonstrated that S-SMase is the only detectable SMase secreted into the culture medium (Schissel et al., 1996). Cells were plated in 100-mm dishes and cultured for 48 h in DMEM/FBS/PSG. The cells were then changed to low protein serum-free media for 12 h. washed 3 times with PBS, and finally incubated for 18 h in fresh serum-free media (6 mL per 100-mm dish) The "18-h conditioned medium" was then collected, centrifuged at 1000×g to pellet any cells and, except where indicated, $ZnCl_2$ (final concentration=100 μM) was added to fully activate and stabilize S-SMase; this S-SMase-containing conditioned media was then used fresh to treat LDL and lipid emulsions.

S-SMase Treatment of LDL and Emulsions. The standard incubation mixture consisted of up to 50 μl of sample (LDL or emulsions). 25 μl of S-SMase-containing conditioned media (see above) and a volume of assay buffer (0.1 M Tris-HCl, pH 7.4, 0.04% azide; or, where indicated, 0.1 M sodium acetate, pH 5.5, 0.04% azide) to bring the final volume to 200 μl. The reactions were incubated at 37° C. for no longer than 16 h and then extracted by the method of Bligh and Dyer (Bligh et al., 1959). For the samples containing [N-palmitoyl-9–10-$^3$H]SM-LDL or [N-palmitoyl-9–10-$^3$H]SM-emulsions, the lower, organic phase was harvested, evaporated under $N_2$, and fractionated by TLC using chloroform:methanol (95:5). The ceramide spots were scraped and directly counted to quantify [$^3$H]ceramide. In all other samples ceramide was determined as described above.

Statistics. Unless otherwise indicated, results are given as means±S.D. (n=3); absent error bars in the figures signify S.D. values smaller than the graphic symbols.

Results

Figure 7A:
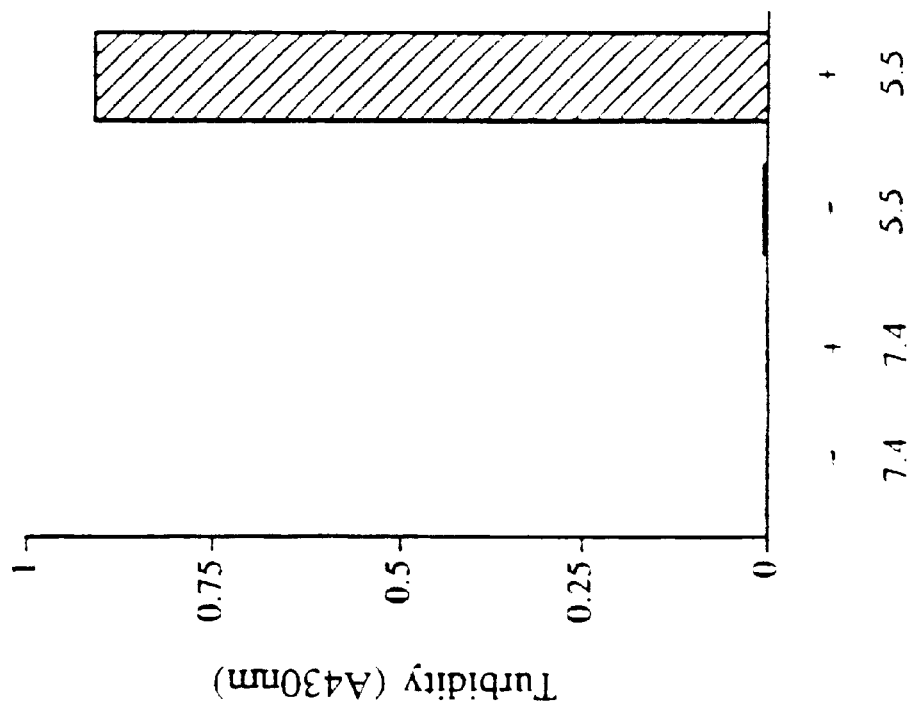
FIGS. 7A–7B. Native human plasma LDL is susceptible to hydrolysis and aggregation by S-SMase at acidic pH. LDL (250 μg protein/mL) was incubated in the absence (−) or presence (+) of S-SMase-containing conditioned media (125 μL/mL) at pH 7.4 (7.4) or pH 5.5 (5.5) for 14 h at 37° C.
Figure 7B:
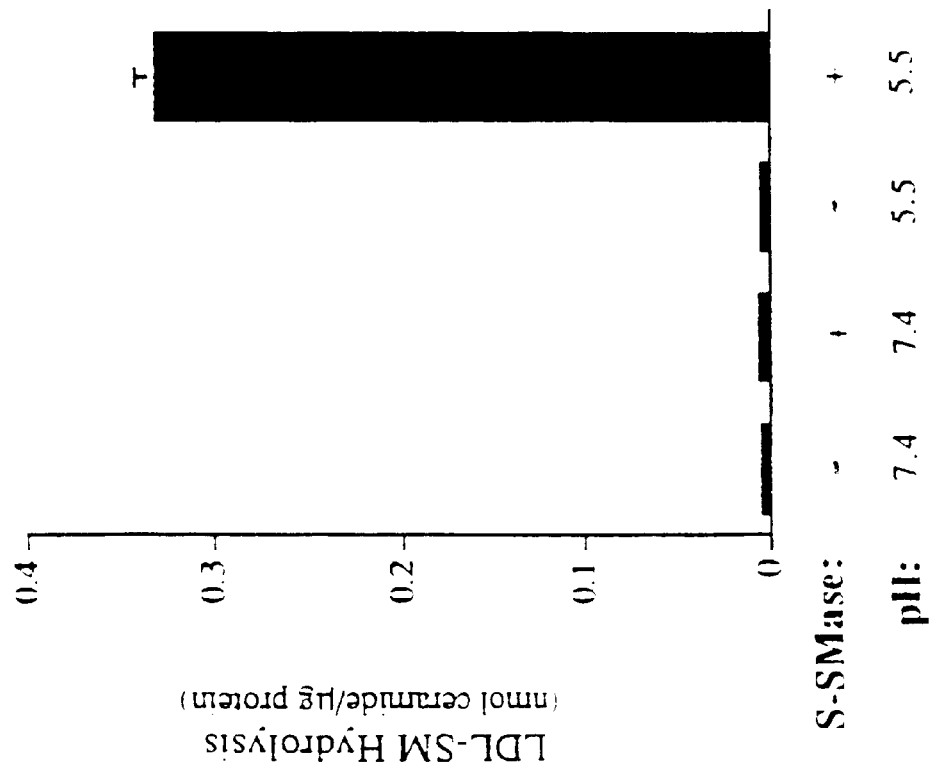

Native LDL can be hydrolyzed and aggregated by S-SMase. Previous LDL aggregation studies with SMase utilized bacterial enzymes (Tabas et al., 1993; Xu et al., 1991). S-SMase, like most mammalian SMases, displays significant substrate specificity in terms of the milieu in which SM is presented to the enzyme (Spence, 1993); the most commonly used in-vitro assays for mammalian SMases use detergent-solubilized SM micelles as the substrate (Spence, 1993). The first question was whether S-SMase can act on intact LDL and, if so, whether it causes LDL aggregation. Although treatment of native LDL with S-SMase at pH 7.4 caused very little SM hydrolysis, S-SMase hydrolyzed significant amounts (nearly 90%) of LDL-SM at pH 5.5 (FIG. 7A), leading to LDL aggregation (FIG. 7B). These data are important for two reasons. First, they demonstrate that S-SMase can hydrolyze the SM in intact LDL without the need for detergent Second, these data formally demonstrate that a mammalian SMase can cause LDL aggregation.

While S-SMase-induced LDL aggregation at acid pH may be important in more advanced atherosclerotic lesions, early subendothelial lipoprotein aggregation likely occurs at a more neutral, physiologic pH. If S-SMase mediates early aggregation, therefore, then lipoprotein-SM should be a substrate for S-SMase at neutral pH. Interestingly, studies by Callahan et al. (Callahan et al., 1983) demonstrate that only the affinity of L-SMase for SM-micelles (i.e. $K_m$) is highly sensitive to changes in pH, whereas the maximal velocity ($V_{max}$) for SM hydrolysis is pH-independent. Since the kinetic properties of S-SMase and L-SMase should be similar (Schissel et al., 1996), it was reasoned that LDL-SM would be hydrolyzed at neutral pH if it could access the active site of S-SMase. Moreover, several physiologically relevant modifications of LDL, including oxidation, hydrolysis with phospholipase $A_2$, and sphingomyelin enrichment, alter the structure of the lipoprotein surface, perhaps allowing S-SMase to bind LDL-SM at neutral pH. These ideas prompted us to test whether modified forms of LDL are better substrates than native LDL for S-SMase at neutral pH.

Figure 8A:
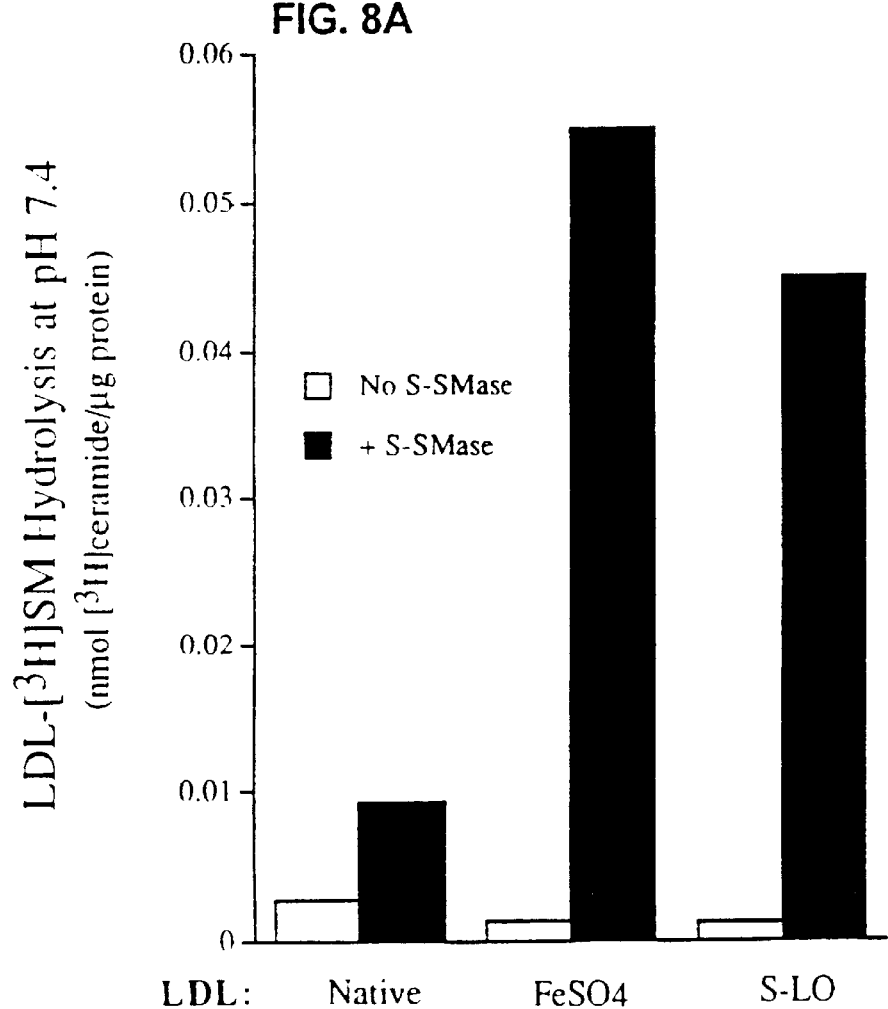
FIGS. 8A–8C. Oxidized LDL is susceptible to hydrolysis by S-SMase at neutral pH. [$^3$H]SM-LDL (Native) was oxidized with 6 μM ferrous sulfate ($FeSO_4$) or with soybean lipoxygenase (S-LO) as described under "Experimental Procedures".
Figure 8B:
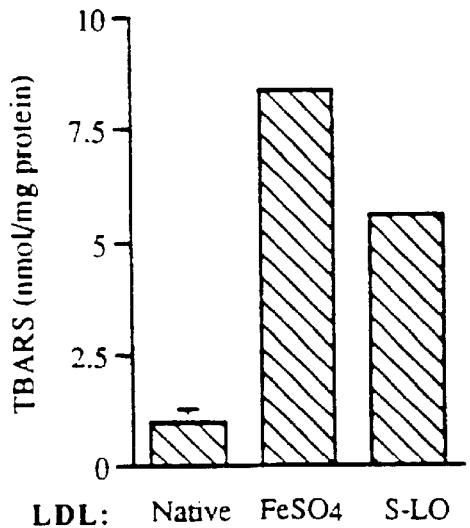
Figure 8C:
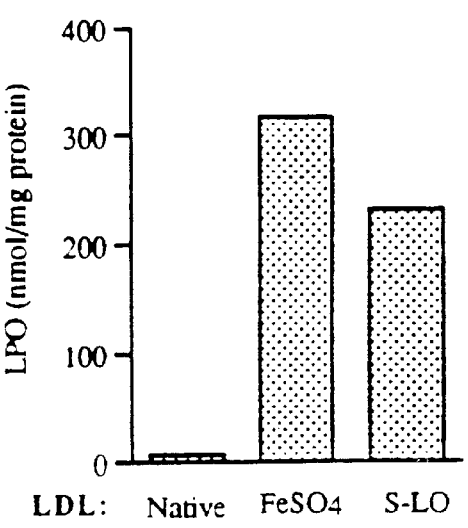
Figure 9:
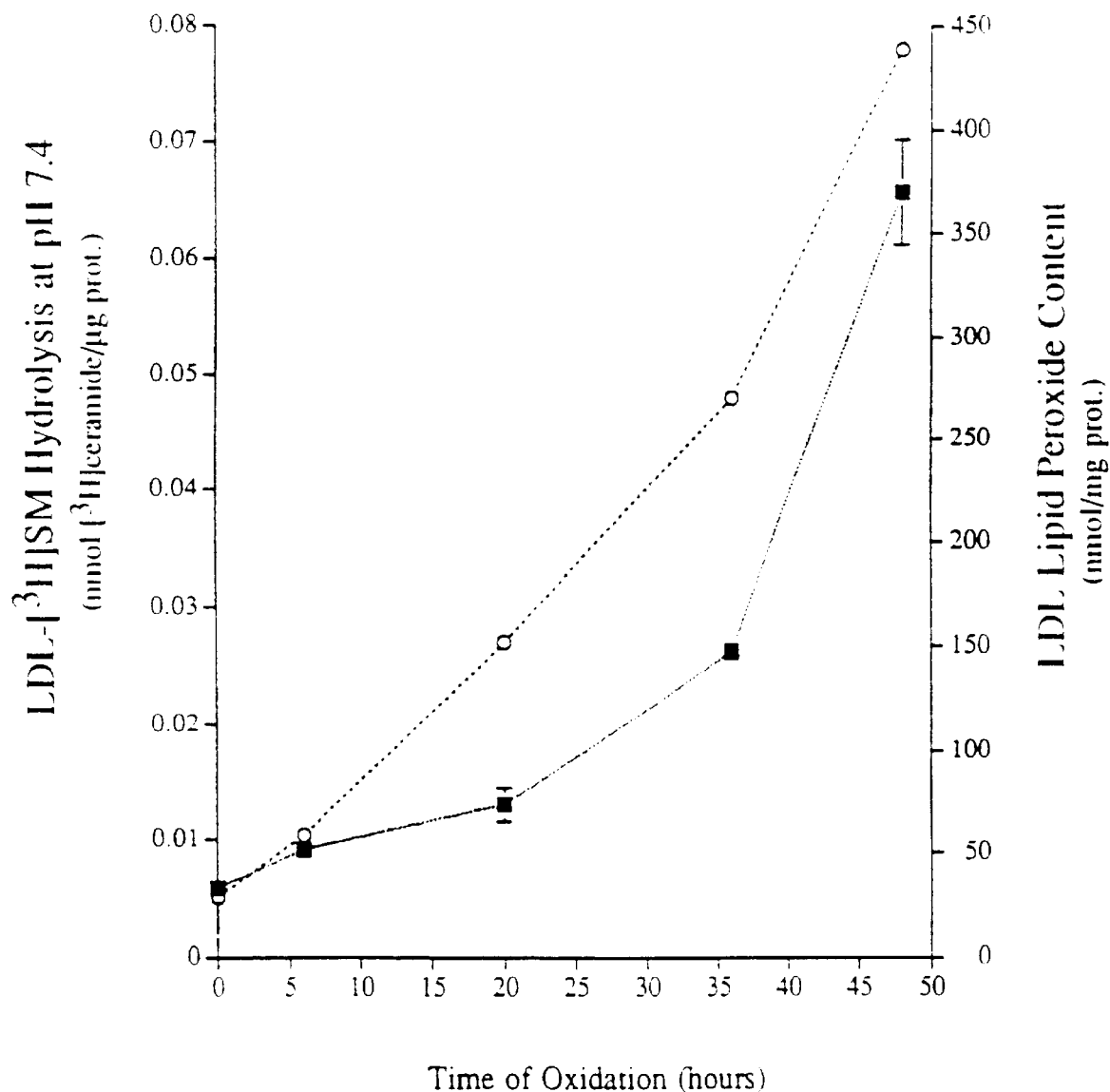
FIG. 9. Relationship between LDL oxidation and susceptibility to hydrolysis by S-SMase at neutral pH. [$^3$H]SM-LDL was oxidized with 6 μM $FeSO_4$ as described under "Experimental Procedures" and, at the indicated time points, oxidation was terminated by the addition of 150 μM BHT and 1 mM EDTA followed by dialysis against 150 mM NaCl, 0.3 mM EDTA for 36 h at 4° C. [H]SM-LDL samples (250 μg protein/mL) were then incubated with S-SMase-containing conditioned media (125 μL/mL) at pH 7.4 for 14 h at 37° C. LDL-[$^3$H]SM hydrolysis was assayed by measuring [$^3$H]ceramide (closed squares). [$^3$H]SM-LDL oxidation was assayed by measuring lipid peroxides (open circles).

Oxidized LDL and sPLA$_2$-treated LDL are hydrolyzed by S-SMase at neutral pH. S-SMase hydrolysis of [$^3$H]SM-labeled LDL oxidized by two independent methods, FeSO$_4$ and lipoxygenase was analyzed. Whereas oxidation alone caused no artifactual LDL-[$^3$H]SM hydrolysis (FIG. 8A, open bars), oxidized [$^3$H]SM-LDL was hydrolyzed 5–6 fold more than native [$^3$H]SM-LDL by S-SMase at pH 7.4 (FIG. 8A, solid bars). Similar results were obtained when LDL-SM hydrolysis was assayed by measuring generation of ceramide mass. Note that FeSO$_4$ ant lipoxygenase caused similar degrees of LDL oxidation as indicated by the levels of thiobarbituric acid-reactive substances [TBARS] (FIG. 8B) and lipid peroxides [LPO] (FIG. 8C) in the LDL. To more precisely define the relationship between LDL oxidation and its susceptibility to S-SMase hydrolysis, [$^3$H]SM-LDL was incubated with FeSO$_4$ for increasing amounts of time and compared its extent of oxidation to its hydrolysis by S-SMase at pH 7.4. [$^3$H]SM-LDL oxidation, assayed by measuring lipid peroxides (FIG. 9, open circles) increased almost linearly with increasing time of incubation with FeSO$_4$; electrophoretic mobility of LDL as assessed by native polyacrylamide gradient gel electrophoresis also increased with time of oxidation. Most importantly, the susceptibility of [$^3$H]SM-LDL to S-SMase hydrolysis at neutral pH was, after an initial threshold level of oxidation, closely correlated with the extent of [$^3$H]SM-LDL oxidation (FIG. 9, closed squares).

Oxidation likely increases S-SMase hydrolysis of LDL-SM through one of two general mechanisms: either oxidized SM itself is a better substrate for S-SMase than non-oxidized SM, or another consequence of LDL oxidation enhances the interaction between LDL-SM and S-SMase. To address the first possible mechanism, [$^3$H]SM-vesicles, which contained no other lipids, were incubated in the absence or presence of FeSO$_4$ under the exact conditions used to oxidize [$^3$H]SM-LDL for the experiment in FIG. 7, followed by incubation with S-SMase at pH 7.4. [$^3$H]SM-vesicles exposed to FeSO$_4$ were hydrolyzed less than two-fold greater than untreated control vesicles, suggesting that another consequence of LDL oxidation is important for stimulating S-SMase hydrolysis of LDL.

Figure 10:
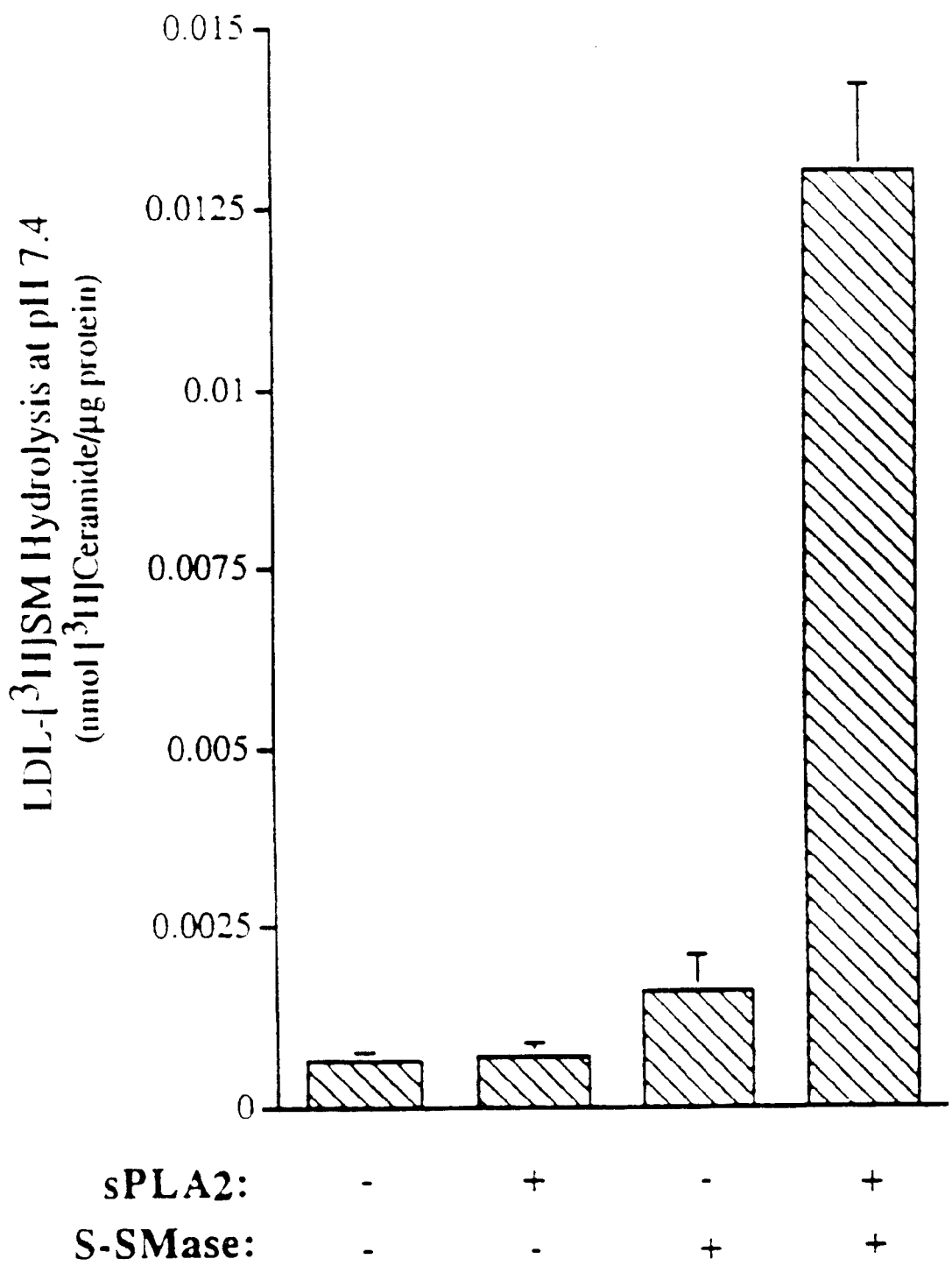
FIG. 10. LDL treated with $sPLA_2$ is susceptible to hydrolysis by S-SMase at neutral pH. [$^3$H]SM-LDL (5 mg/mL) was incubated in the absence (−) or presence (+) of $sPLA_2$ for 14 h at 37°C. Samples of control and treated [$^3$H]SM-LDL (250 μg/mL) were then incubated in the absence (−) or presence (+) of S-SMase-containing conditioned media (125 μL/mL) at pH 7.4 for 14 h at 37° C. LDL-[$^3$H]SM hydrolysis was assayed by measuring [$^3$H] ceramide.

The biological actions of oxidized LDL (e.g. scavenger receptor binding, cytotoxicity, and monocyte chemotaxis) are largely attributed to its overall negative charge and enrichment in lysophosphatidylcholine (Krieger et al., 1994: Quinn et al., 1988; Welzien, 1979; Niewoehner et al.; 1989). Thus, these modifications were studied individually to define the critical components) in oxidized LDL that stimulates S-SMase. To examine negative charge, the hydrolysis of acetylated-LDL, a highly negatively charged form of LDL (Goldstein et al., 1979), was compared to the hydrolysis of native LDL by S-SMase at pH 7.4 and no significant difference in LDL-sphingomyelin hydrolysis were found. Thus, adding negative charges to LDL, at least via acetylation, does not increase its hydrolysis by S-SMase. Lysophosphatidylcholine enrichment of LDL occurs during oxidation due to activation of an apparently latent phospholipase $A_2$ activity (Parthasarathy et al., 1985). Importantly, Camejo and colleagues (Hurt-Cameho et al., 1997; Sartipy et al., 1996) have shown that the nonpancreatic secretory phospholipase $A_2$ type II (sPLA$_2$) is abundant in both normal and lesional human arteries and can act on LDL in vitro, suggesting that LDL may be enriched with lysophosphatidylcholine by SPLA, in vivo. Moreover, Lusis and colleagues (Ivandic et al., 1996) have reported that transgenic mice overexpressing sPLA$_2$ have more extensive atherosclerotic lesions than wild-type mice. With this background, the next question was whether LDL treated with sPLA$_2$ was more susceptible than native LDL to S-SMase hydrolysis at neutral pH. Whereas sPLA, treatment alone caused no [$^3$H]SM-LDL hydrolysis, S-SMase hydrolysis of [$^3$H]SM-LDL at pH 7.4 was markedly enhanced by treating the LDL with sPLA$_2$ (FIG. 10). Furthermore, exogenously added lysophosphatidylcholine stimulated S-SMase hydrolysis of [$^3$H]SM-LDL 2–3 fold at pH 7.4. In summary, LDL oxidation markedly increases S-SMase hydrolysis of LDL-SM at neutral pH. While it is possible that several oxidation products are acting together, lysophosphatidylcholine appears to be particularly effective in stimulating S-SMase hydrolysis of LDL.

Figure 11A:
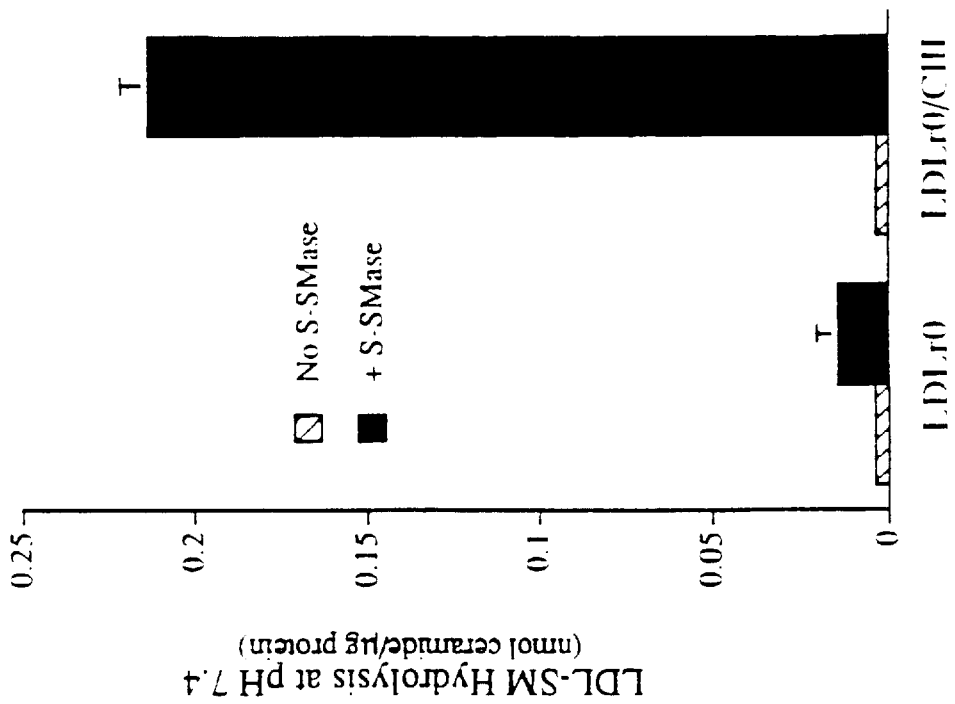
FIGS. 11A–B. Apo CIII enhances the susceptibility of [$^3$H]SM-emulsions and murine plasma LDL to hydrolysis by S-SMase at neutral pH.

Apolipoprotein CIII stimulates S-SMase hydrolysis of lipoprotein-SM. Apolipoprotein CIII (apo CIII) is associated with severe hypertriglyceridemia (Ito et al. 1990; Dammerman et al., 1993) and, recently, has been identified as a possible contributing factor in familial combined hyperlipidemia (Masucci-Magoulas et al., 1997; Dallinga-Thie et al., 1997). In addition, apo CIII has been linked to certain forms of coronary heart disease (Rigoli et al., 1995), and its overexpression in mice significantly increases atherosclerosis (Masucci-Magoulas et al., 1997). While apo CIII is known to inhibit lipoprotein lipolysis (Ito et al., 1990), the atherogenic mechanisms of apo CIII are not known. Interestingly, Ahmad et al. (Ahmad et al., 1986) have shown that Apo CIII, but not other apolipoproteins, stimulates L-SMase hydrolysis of SM-liposomes. Given that L-SMase and S-SMase are such similar enzymes (Schissel et al., 1996), the next question was whether Apo CIII could stimulate S-SMase hydrolysis of lipoprotein-SM at neutral pH. Because enriching native LDL with apo CIII in vitro proved extremely difficult, the effect of apo CIII on S-SMase hydrolysis of [$^3$H]SM-labeled emulsions containing lipids in the same proportions as in LDL was examined first. For this experiment, three different types of emulsions were treated with S-SMase at pH 7.4: control emulsions not enriched with Apo CIII (control), emulsions mixed with apo CIII (+CIII, emulsion-bound+free CIII), and emulsions mixed with apo CIII followed by re-isolation from free apo CIII (+CIII, emulsion-bound only). While S-SMase hydrolysis of the emulsions with bound plus free CIII was two-fold greater than hydrolysis of the control emulsions, similar to Ahmad et al. (Ahmad et al., 1989), it was found that emulsions with only bound CIII were hydrolyzed approximately ten-fold more than control emulsions (FIG. 11A). Thus, apo CIII stimulates S-SMase hydrolysis of LDL-like emulsions, particularly in the absence of free apo CIII.

Figure 11B:
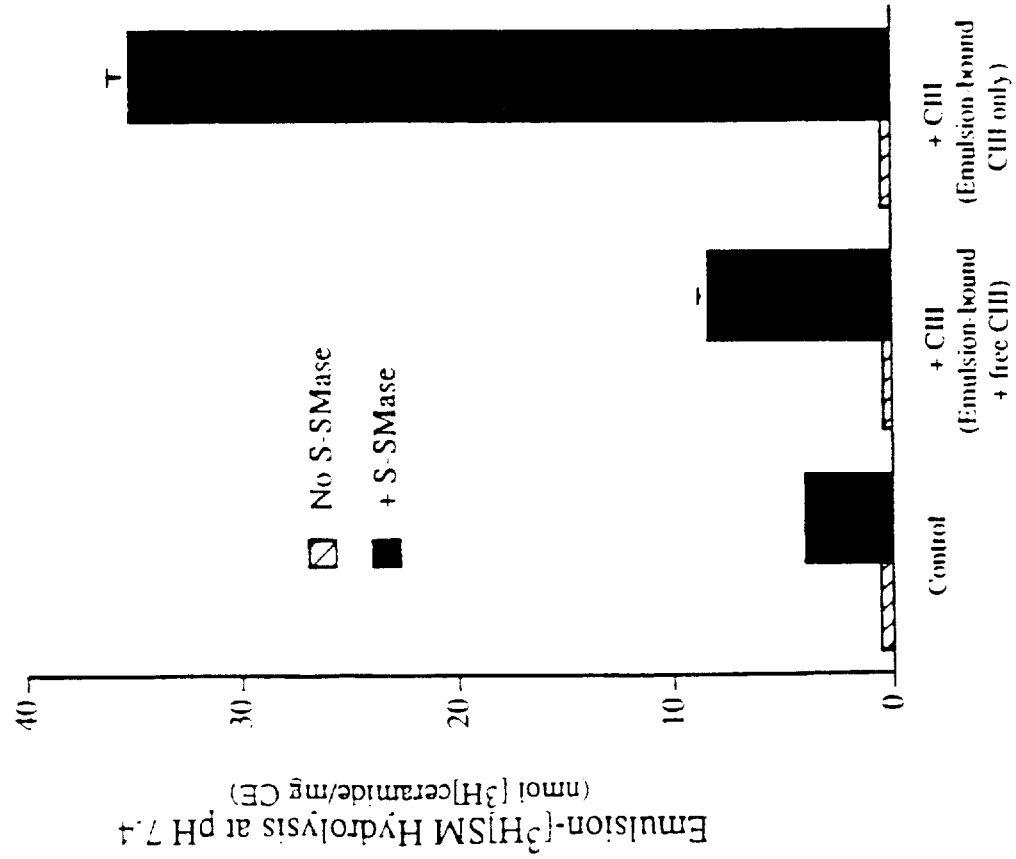

To determine whether apo CIII stimulates S-SMase hydrolysis of lipoprotein-SM, the hydrolysis of LDL from LDLr0 mice expressing a human apo CIII transgene (LDLr0/CIII) (Masucci-Magoulas et al., 1997) was compared with the hydrolysis of LDL from LDLr0 mice (Ishibashi et al., 1993); LDL from the LDLr0/CIII mouse is enriched in apo CIII, whereas LDL from the LDLr0 mouse is not. The data in FIG. 11B clearly show that LDL from LDLr0/CIII mice is significantly hydrolyzed by S-SMase at pH 7.4, whereas LDL from LDLr0 mice is hydrolyzed very little. Importantly, the turbidity at $A_{430}$ nm of LDLr0/CIII LDL, but not for the LDLr0 LDL, increased 1.5 fold following treatment with S-SMase, indicating particle aggregation. Lipoprotein enrichment with apo CIII, therefore, increases its susceptibility to hydrolysis and aggregation induced by S-SMase.

Plasma LDL from E0 mice is efficiently hydrolyzed by S-SMase at neutral pH. The E0 mouse develops widely distributed and complex atherosclerotic lesions like those seen in humans and thus has become a widely used model of atherosclerosis (Plump et al., 1993; Zhang et al., 1992). A likely factor contributing to the extensive atherosclerosis in these mice is the atherogenicity of E0 lipoproteins, but the mechanisms whereby apo E-deficient lipoproteins lead to foam cell formation and other lesional events is not known. Another question was whether plasma LDL from these mice was susceptible to S-SMase at neutral pH; as a comparison, plasma LDL from LDLr0 mice was used, which mice also develop atherosclerosis, though to a lesser degree than E0 mice (Ishibashi et al., 1993; Plump et al., 1992; Zhang et al., 1992). While the ceramide contents of native plasma LDL from these two strains of mice are equivalent (FIG. 12A, hatched bars), treatment with S-SMase at pH 7.4 resulted in generation of 4–5-fold more ceramide in LDL from E0 mice than in LDL from LDLr0 mice (FIG. 12A, solid bars), which resulted in aggregation of E0 LDL.

Figure 12B:
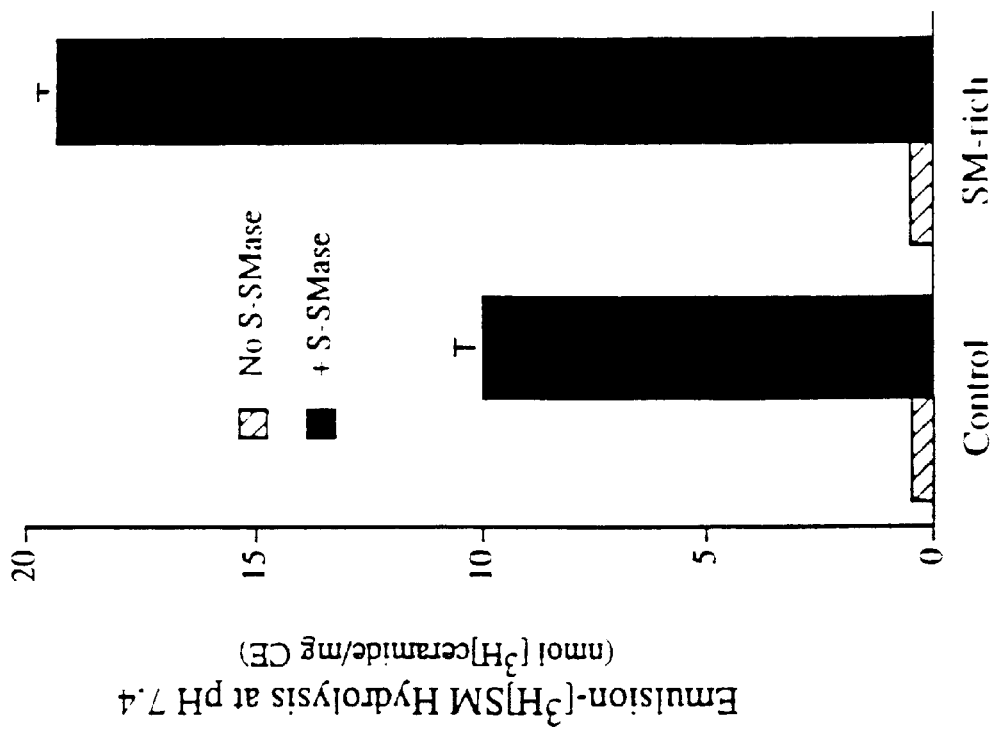
FIGS. 12A–12B. E0 LDL and SM-rich [$^3$H]SM-emulsions are susceptible to hydrolysis by S-SMase at neutral pH.
Figure 12A:
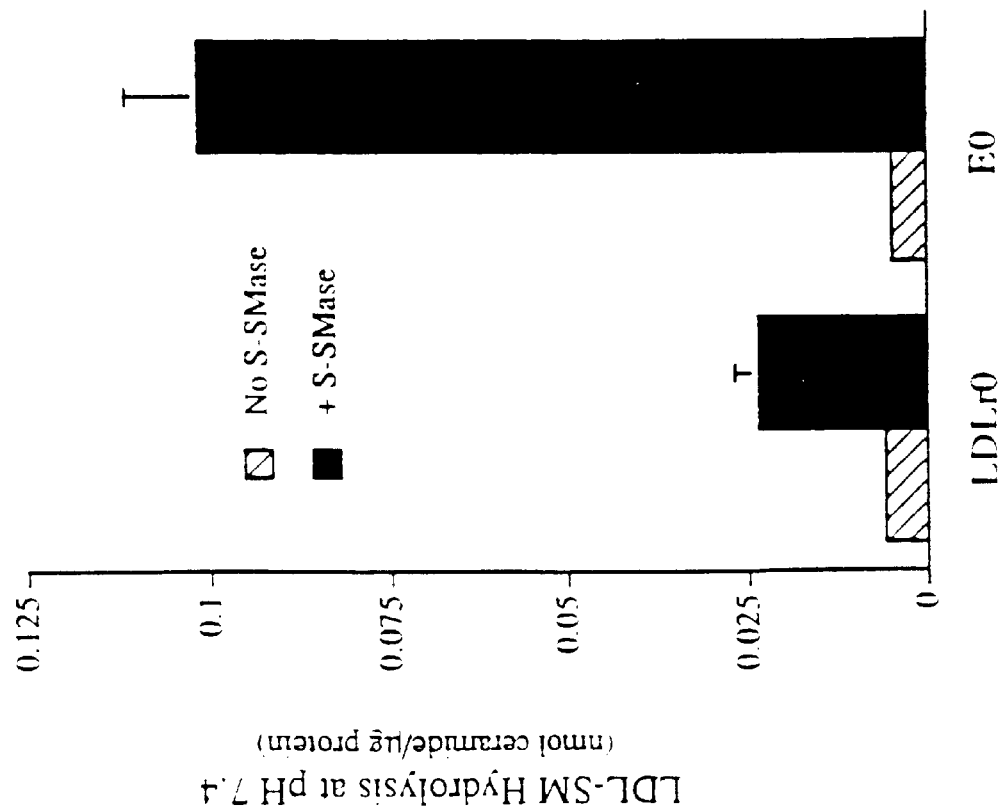

E0 LDL has a high SM:PC molar ratio (0.36) compared with LDLr0 LDL, which has a SM:PC ratio of 0.19; the mechanism appears to be a combination of increased SM synthesis and decreased plasma SM clearance in the E0 mice. SM-enrichment of LDL may increase substrate availability to S-SMase and thereby promote ceramide generation, which is required for LDL aggregation (Schissel et al., 1996); note that particles enriched in both SM and ceramide aggregate readily (Schissel et al., 1996). Thus, one possible factor contributing to the increased susceptibility of E0 LDL to S-SMase is its relatively high SM:PC ratio. To test the importance of the membrane SM:PC ratio on S-SMase activity in a more controlled system, [$^3$H]SM-labeled emulsions were prepared containing lipids similar to those in human LDL with a SM:PC ratio of either 0.5 (control emulsions) or 1.5 (SM-rich emulsions) and then treated with S-SMase at pH 7.4. Although the control emulsions, unlike native plasma LDL, were significantly hydrolyzed by S-SMase, SM-enrichment resulted in a two-fold stimulation of [$^3$H]SM-emulsion hydrolysis by S-SMase (FIG. 12B). Together, these findings demonstrate that SM enrichment of lipoproteins may markedly enhance their hydrolysis by S-SMase at neutral pH. Note, however, that other factors must be involved. For example, human native plasma LDL has a higher SM:PC ratio than E0 LDL and the same ratio as the "control" emulsions in FIG. 12B, and yet it is a worse substrate for S-SMase at neutral pH than either of these two particles (see FIG. 12).

Figure 13:
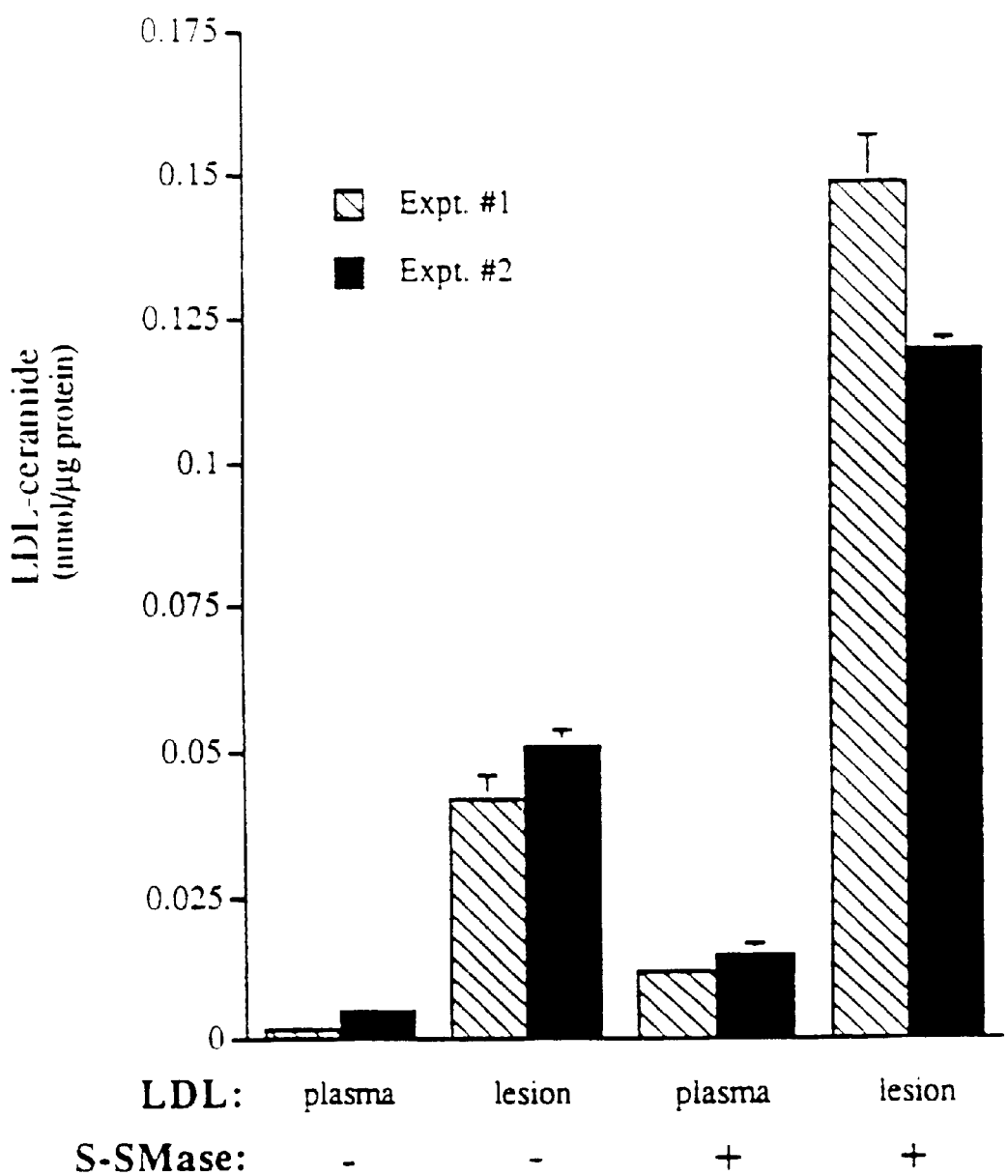
FIG. 13. Human lesional LDL is susceptible to hydrolysis by S-SMase at neutral pH. Human plasma LDL (plasma) and LDL extracted from human atherectomy specimens (lesion) were isolated from the same donor. LDL preparations from two different patients (Expte. #1, hatched bars and Expt. #2, solid bars) were incubated at a concentration of 100 μg protein/mL in the absence (−) or presence (+) of S-SMase-containing conditioned media (125 μL/mL) at pH 7.4 for 14 h at 37° C. Lipids were then extracted and assayed for ceramide mass. Incubation at 37° C. in the absence of S-SMase did not affect the ceramide contents of plasma and lesional LDL.

Human atheroma-derived LDL is hydrolyzed by S-SMase at neutral pH. The data presented thus far clearly demonstrate that LDL modified in vitro to forms reported to be present in vivo is a significantly better substrate than native LDL for S-SMase at neutral pH. A critical issue regarding the physiologic relevance of these findings, however, is whether LDL modified in the arterial wall shows greater susceptibility to hydrolysis by S-SMase than native LDL. To address this important point, we compared the S-SMase hydrolysis of lesional LDL, extracted from two different atherectomy samples, to the hydrolysis of same-donor plasma LDL. First, the data in FIG. 13 confirm the report that lesion LDL is markedly enriched in ceramide compared to plasma LDL (compare first pair of bars to second pair of bars), indicating that LDL is hydrolyzed by a SMase in the arterial wall. Most importantly, however, treatment of lesional LDL with S-SMase at pH 7.4 generates nearly ten-fold more ceramide than treatment of plasma LDL (FIG. 13, compare third pair of bars to fourth pair of bars). LDL retained in the arterial wall, therefore, is an excellent substrate for S-SMase at neutral pH.

What are the critical modifications to lesional LDL that stimulate its hydrolysis by S-SMase? To begin addressing this question, lesional LDL was examined for the presence of the LDL modifications that have been identified above as increasing susceptibility to hydrolysis by S-SMase at neutral pH in vitro. To determine whether lesional LDL shows evidence of oxidation, the levels of TBARS was compared and lipid peroxides in the lesional LDL samples from FIG. 13 to those in the same-donor plasma LDL. The levels of TBARS and lipid peroxides, however, in both plasma and lesional LDL were below the detection limit of the assay (<0.5 nmol/mg protein and <4 nmol/mg protein for TBARS and lipid peroxides, respectively). Although one interpretation of these findings is that the lesional LDL was not oxidized, other studies have suggested that these markers of oxidation can be lost during the isolation of LDL (Esterbauer et al., 1987; Steinbrecher et al., 1987) or that other markers of oxidation may be more relevant to in-vivo events (Leeuwenburgh et al., 1997). Thus, pending further study, oxidation may still prove to be an important modification to lesional LDL that stimulates S-SMase. Similarly, detection of apo CIII in the two samples of lesional LDL was not accomplised, but it is possible that less dense lesional lipoproteins, or lipoproteins isolated from other individuals or from earlier lesions might have shown evidence of apo CIII.

The next question was whether the ratio of SM to PC was different for lesional and plasma LDL. Note that other investigators have shown previously that LDL extracted from both animal and human atherosclerotic lesions is enriched in sphingomyelin compared with plasma LDL (Ylä-Herttuala et al., 1989; Daugherty et al., 1988; Hoff, 1983). The data in Table 1 show the SM and PC contents of the lesional and same-donor plasma LDL samples from FIG. 13. Whereas the PC level in lesional LDL was modestly reduced compared with plasma LDL, suggesting limited arterial-wall PC hydrolysis, the SM content of lesional LDL was nearly three-fold higher than the level of SM in plasma LDL. As a result, the SM:PC ratio for lesional LDL was 3–4-fold higher than the ratio for plasma LDL (Table 1). Thus, lesional LDL is highly enriched in SM, a modification that stimulates S-SMase hydrolysis of LDL at neutral pH in vitro (see FIG. 12).

Discussion

LDL hydrolysis by bacterial SMase causes LDL self-aggregation, an important process in atherogenesis (see Introduction), and that aggregated LDL retained in vivo shows evidence of hydrolysis by a SMase in the subendothelium (Schissel et al., 1996). Although the mammalian SMase responsible for subendothelial lipoprotein-SM hydrolysis has yet to be identified, several cell types, including macrophages, secrete a zinc-activated SMase (S-SMase) (Schissel et al., 1996). Cultured human coronary artery endothelial cells secrete abundant amounts of S-SMase basolaterally, making the endothelium a potential source of the enzyme in the pre-lesional artery. Furthermore, preliminary immunohistochemistry studies indicate that S-SMase is present in both the pre-lesional artery and in atherosclerotic lesions. Thus, S-SMase is a leading candidate for the arterial-wall SMase that hydrolyzes retained lipoproteins. S-SMase, however, has an acid pH optimum using a standard in-vitro, detergent-based SM-micelle assay (Schissel et al., 1996; Spence et al., 1989). Thus, the goal of this study was to determine whether LDL-SM could be hydrolyzed by S-SMase under more physiologic conditions. S-SMase can hydrolyze and aggregate native plasma LDL, but only at acid pH (FIG. 7). Although S-SMase-induced LDL aggregation under these conditions may be relevant in more advanced lesions, where an acidic environment may exist in the vicinity of lesion macrophages (Tapper et al., 1992; Silver et al., 1988) or as a result of hypoxia-induced metabolic acidosis (Tsukamoto et al., 1996), early lipoprotein aggregation likely occurs at a more neutral, physiologic pH. Remarkably, several modified forms of LDL, known to be atherogenic and occur in vivo, are much better substrates for S-SMase at neutral pH than native LDL.

Figure 2:
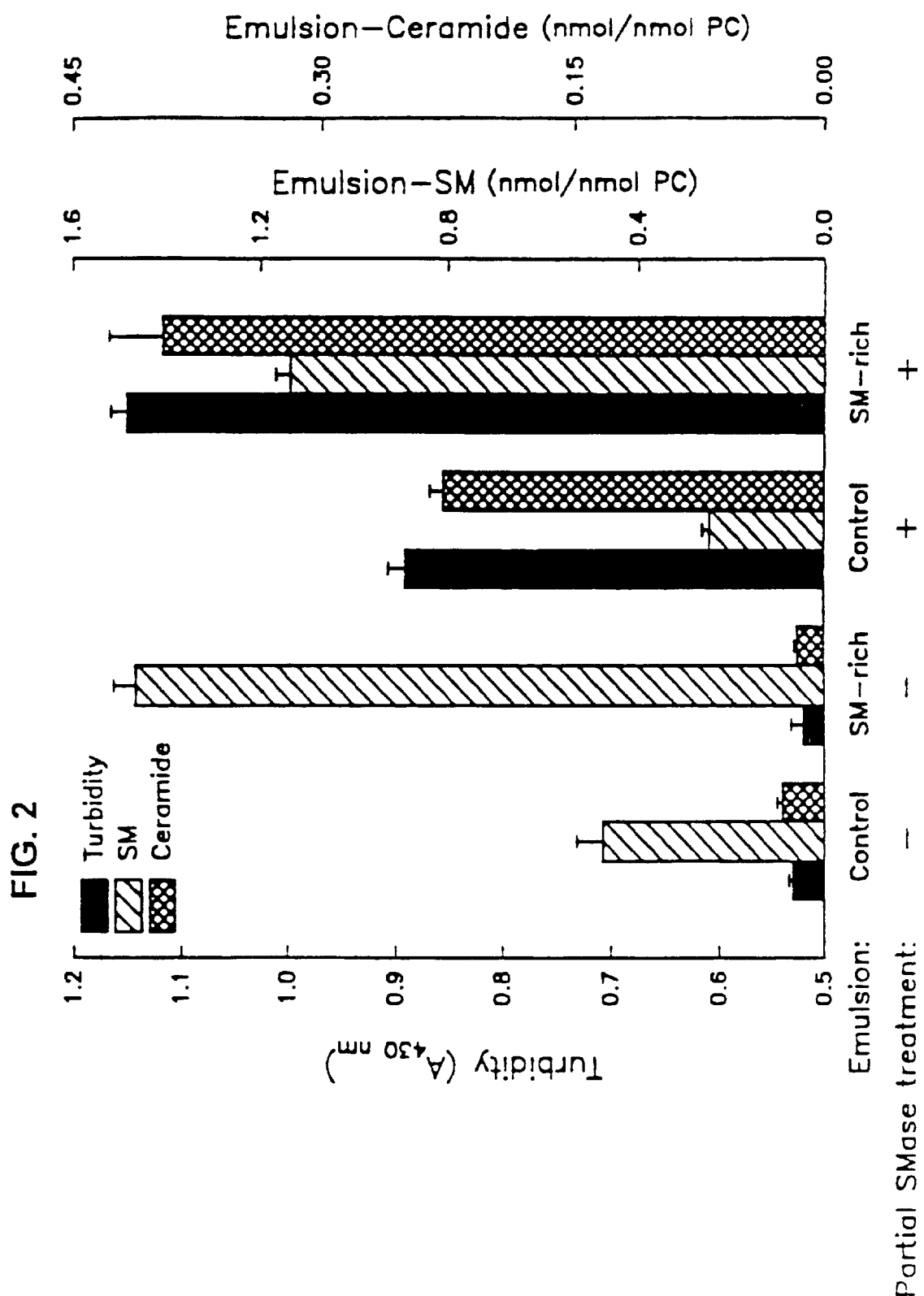
FIG. 2. Dependence of SMase-induced aggregation of LDL-lipid emulsions on the presence of ceramide. Emulsions made from LDL lipids (control) or LDL lipids enriched with SM (SM-rich) were incubated at 37° C. for 15 min in PBS containing 5 mM $MgCl_3 \pm 50$ mU B. cereus SMase/ml. EDTA was then added to a final concentration of 25 mM to stop SM hydrolysis before it had proceeded to completion, and the emulsions were incubated for an additional 4 h to allow aggregation to occur. Samples were then assayed for turbidity (solid bars), SM content (diagonally hatched bars), and ceramide content (cross-hatched bars).
Figure 3:
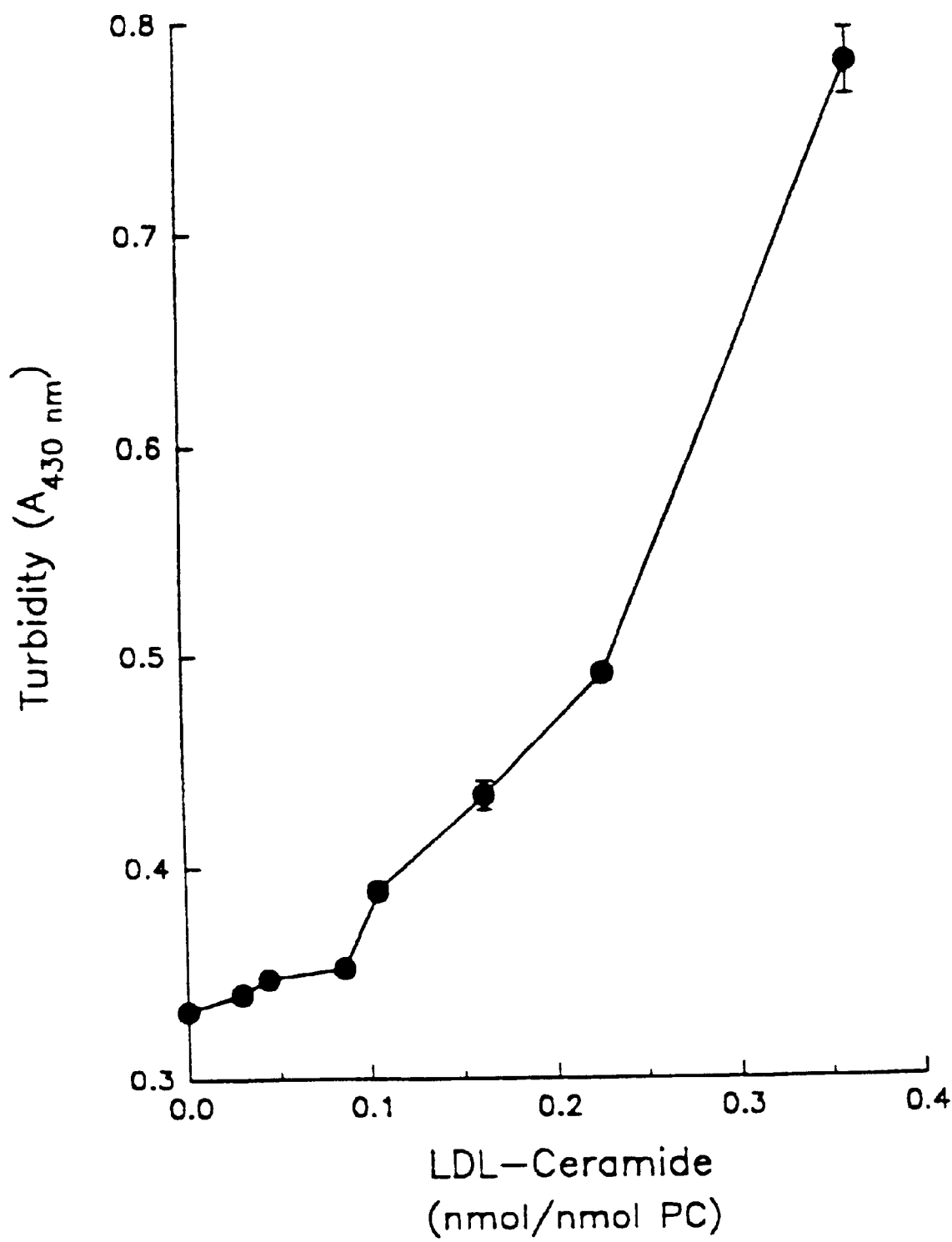
FIG. 3. Relationship between LDL-ceramide content and LDL aggregation. LDL was incubated with B. cereus SMase as described in the legend to FIG. 1 for 0, 1, 3, 5, 7, 10, 12, 15, 20, or 60 min. At the end of the SMase incubation 25 mM EDTA was added to stop SM hydrolysis and the samples were incubated further so that the total incubation time for all samples was 4 h. Displayed are particle ceramide contents on the x-axis and aggregation (turbidity) on the y-axis.

Oxidized LDL, for example, is significantly hydrolyzed by S-SMase at neutral pH (FIGS. 2 and 3). Although this hydrolysis was not sufficient to cause visible aggregation, the level of ceramide generated (~0.5 nmol ceramide/$\mu$g protein) was very close to the threshold level (~0.8 nmol ceramide/$\mu$g protein) required for LDL aggregation in vitro (Schissel et al., 1996). Furthermore, it is possible that other arterial-wall factors, such as proteoglycans, collagen, and lipoprotein lipase (5, Camejo et al., 1993; Goldber et al., 1996), lower the threshold for ceramide-mediated LDL aggregation in vivo. Interestingly, oxidized LDL treated with S-SMase at neutral pH contained similar levels of ceramide as aggregated lesional LDL (Schissel et al., 1996) (also, compare FIG. 8A with FIG. 13), consistent with the idea that the threshold for ceramide-mediated aggregation may be lowered in vivo. Although several consequences of LDL oxidation may contribute to stimulation of S-SMase, one of these, namely, hydrolysis of LDL by PLA (Parthasarathy et al., 1985; Ivandic et al., 1996, may be particularly important. Specifically, LDL hydrolyzed by sPLA$_2$, an enzyme known to be present in the arterial wall (Hurt-Camejo et al., 1997), was hydrolyzed significantly more than native LDL by S-SMase at neutral pH (FIG. 10).

Other atherogenic particles are susceptible to S-SMase at neutral pH include apo CIII-enriched lipoproteins (FIG. 11) and plasma LDL from E0 mice (FIG. 12A); the E0 particles aggregate after treatment with S-SMase at neutral pH (see text). Since susceptibility of SM and apo CIII-containing emulsions to hydrolysis by S-SMase is greater in the absence of free apo CIII (FIG. 11A), apo CIII may act as a bridge between S-SMase and membrane SM, thereby stimulating SM hydrolysis. A property of E0 LDL that likely plays a role in its susceptibility to S-SMase is the high SM:PC ratio in these particles (FIG. 12B), although other factors are probably also involved. In particular, human native plasma LDL has a SM:PC ratio that is greater than E0 LDL and equal to the "control" emulsions in FIG. 12B and yet is substantially less susceptible to hydrolysis by S-SMase at neutral pH than these particles. Since E0 LDL contains mostly apo B48 (Plump et al., 1992; Zhang et al., 1992) and the emulsions contain no protein, it is possible that apo B100, the protein in human native plasma LDL, confers relative resistance to hydrolysis by S-SMase. In this context, ii is possible that oxidative degradation of apo B100 contributes to the enhanced susceptibility of oxidized LDL to hydrolysis by S-SMase.

Most importantly, LDL extracted from atherosclerotic lesions was hydrolyzed ten-fold more than same-donor plasma LDL by S-SMase at neutral pH (FIG. 13), indicating that lesional LDL is modified in vivo, either before or after retention in lesions (see below), to a form that renders it more susceptible to hydrolysis by S-SMase. Although it is difficult to determine the specific characteristics of lesional LDL that increase its susceptibility to S-SMase, lesional LDL is enriched in SM (Table 1), which is shown here to be a potent stimulator of S-SMase hydrolysis of LDL (FIG. 12B). Evidence of oxidation was not found. Detecting oxidation of lesional LDL may require more sensitive and/or specific techniques, such as immunostaining for oxidized epitopes (Ylä-Herttuala et al., 1989) or evidence of myeloperoxidase-induced oxidation (Leeuwenburgh et al., 1997). Thus, oxidation may, in fact, be an important modification of LDL in vivo that increases LDL-SM hydrolysis by S-SMase. Nonetheless, SM-enrichment of LDL in the arterial wall may prove to be an important process regulating hydrolysis and aggregation of LDL in the subendothelium. The mechanism of SM enrichment of lesional LDL is not known. The possibilities include SM enrichment of LDL retained in the subendothelium (e.g., by increased arterial-wall synthesis of SM followed by transfer of the SM to retained LDL) or selective uptake of SM-rich LDL from the plasma (see, for example, Portman et al., 1970).

In summary, lipoprotein-SM hydrolysis, which occurs in the subendothelium in vivo (Schissel et al., 1996), causes LDL aggregation and enhances lipoprotein retention on matrix (Tabas et al., 1993; Xu et al., 1991). S-SMase, which is secreted by arterial-wall and lesional cells in culture, can efficiently hydrolyze and aggregate modified LDL at neutral pH. Most importantly, LDL extracted from atherosclerotic lesions, but not plasma LDL, is significantly hydrolyzed by S-SMase at neutral pH, indicating that modifications present in vivo can stimulate S-SMase hydrolysis of LDL. S-SMase, therefore, is a prime candidate for the arterial-wall SMase that acts on retained lipoproteins, causing lipoprotein aggregation and leading to lesion initiation and progression.

Footnotes

1. Abbreviations used: apo, apolipoprotein; DMEM, Dulbecco's modified Eagle's medium; LDL, low-density lipoprotein; L-SMase, lysosomal sphingomyelinase; PBS, phosphate-buffered saline; PC, phosphatidylcholine; SM, sphingomyelin; SMase, sphingomyelinase; sPLA$_2$, non-pancreatic secretory phospholipase A$_2$; S-SMase; secretory sphingomyelinase; TBARS, thiobarbituric acid-reactive substances; TLC, thin-layer chromatography.

TABLE I

SPHINGOMYELIN AND PHOSPHATIDYLCHOLINE CONTENTS OF PLASMA AND LESION LDL[b]

| Sample | Sphingomyelin Content (nmol/mg protein) | Phosphatidylcholine Content (nmol/mg protein) | SM: PC Molar Ratio |
|---|---|---|---|
| Plasma LDL #1 | 376 ± 20 | 785 ± 13 | 0.478 ± 0.022 |
| Plasma | 352 ± 10 | 727 ± 6 | 0.473 ± 0.025 |

TABLE I-continued

SPHINGOMYELIN AND PHOSPHATIDYLCHOLINE CONTENTS OF PLASMA AND LESION LDL[b]

| Sample | Sphingomyelin Content (nmol/mg protein) | Phosphatidylcholine Content (nmol/mg protein) | SM: PC Molar Ratio |
|---|---|---|---|
| LDL #2 | | | |
| Lesion LDL #1 | 858 ± 19 | 710 ± 14 | 1.203 ± 0.040 |
| Lesion LDL #2 | 902 ± 50 | 516 ± 22 | 1.740 ± 0.170 |

Plasma and lesional LDL from FIG. 13 (25 μg protein) were lipid-extracted, and the sphingomyelin and phosphatidylcholine contents in the lipid extracts were assayed as described under "Experimental Procedures".

EXAMPLE 3

Evidence that Both Secreted and Lysosomal Sphingomyelinase are Directly Activated by Zinc but Differ in Their Exposure to Intracellular Zinc*

Many cell types secrete a $Zn^{2+}$-dependent SMase (S-SMase) This enzyme arises from the same gene and the same mRNA that gives rise to lysosomal SMase (L-SMase), which has been reported to be a cation-independent enzyme. Herein, evidence is presented for a model to explain how a single mRNA gives rise to two forms of SMase with apparent differences in $Zn^{2+}$-dependency. First, $Zn^{2+}$-induced activation of S-SMase does not involve a $Zn^{2+}$-dependent cofactor, indicating direct activation by $Zn^{2+}$, and the enzyme binds $Zn^{2+}$ as assessed by zinc-chelate chromatography Second, L-SMase activity in sonicated cell homogenates was inhibited by vigorous chelation of $Zn^{2+}$ and partially reactivated by addition of exogenous $Zn^{2+}$. Thus, both L- and S-SMase are zinc-activated enzymes, and, indeed, the amino acid sequence includes several $Zn^{2+}$-binding motifs. Interestingly, SMase activity in a lysosome-rich 16,000-x-g pellet was ~50% $Zn^{2+}$-dependent, suggesting sub-saturating levels of $Zn^{2+}$ in intact lysosomes and raising the possibility of regulation by $Zn^{2+}$ availability. Third, when S-SMase was incubated with SMase-negative cells, the enzyme was internalized and trafficked to lysosomes; when subsequently assayed in the cell homogenate, the enzyme became active in the absence of exogenously added $Zn^{2+}$ and was inactivated by subsequent chelation of $Zn^{2+}$. These data suggest a model in which L-SMase is exposed to cellular $Zn^{2+}$ during trafficking to lysosomes or in lysosomes, and some additional $Zn^{2+}$ exposure may occur during preparation of the sonicated cell homogenate. In contrast, the pathway targeting S-SMase to secretion, which we showed is clearly distinct from the lysosomal targeting pathway, appears to be sequestered from cellular pools of $Zn^{2+}$; thus S-SMase requires exogenous $Zn^{2+}$ for activity. This model provides important information for understanding the enzymology and regulation of L- and S-SMase and for the design of animal models to explore their functions in vivo.

SMases[2] (SM phosphodiesterase, E.C. 3.1.4.12) have been implicated in a wide variety of physiological and pathophysiological processes, including lysosomal hydrolysis of endocytosed SM (Levade et al., 1986; Brady, 1983). ceramide-mediated cell signalling (Kolesnick, 1991; Hannun et al., 1989), membrane vesiculation (Skiba et al., 1996) alterations in intracellular cholesterol trafficking (Skiba et al., 1996; Slotte et al., 1988; Porn et al., 1995; Okwu et al., 1994), and atherogenesis (Xu et al., 1991; Tabas et al., 1993; Schissel et al., 1996; Williams et al., 1995). far, only one mammalian SMase gene has been cloned, the "acid SMase" or "ASM" gene, which gives rise to lysosomal SMase (L-SMase) (Schuchman et al., 1991). This gene can also give rise to a secreted SMase (S-SMase) (Schissel et al., 1996). Both L- and S-SMase are absent from the cells of patients with types A and B Niemann-Pick disease, which is due to mutations in the ASM gene, and from ASM knock-out mice (Schissel et al., 1996). The secreted form of the enzyme, which requires exogenously added $Zn^{2+}$ for activity (Schissel et al., 1996), may also be involved in some of the processes mentioned above.

S-SMase may have significant physiologic roles, since extracellular SM hydrolysis may be involved in some or all of the non-lysosomal processes listed above. For example, several lines of evidence have implicated extracellular SM hydrolysis in atherogenesis. First, treatment of LDL with SMase ifn vitro leads to LDL aggregation (Xu et al., 1991; Tabas et al., 1993), which is a prominent event during atherogenesis (Hoff et al., 1985; Nievelstein et al., 1991; Guyton et al., 1996) and one that leads to massive macrophage foam cell formation (Xu et al., 1991; Tabas et al., 1993; Hoff et al., 1990; Khoo et al., 1988; suits et al., 1989). Second, aggregated LDL from human and animal atherosclerotic lesions shows evidence of hydrolysis by extracellular SMase, and LDL retained in rabbit aortic strips ex vivo is hydrolyzed by an extracellular, cation-dependent SMase (Schissel et al., 1996). Third, S-SMase, a leading candidate for this arterial-wall enzyme, is secreted by macrophages (Schissel et al., 1996) and endothelial cells[2], cell types found in atherosclerotic lesions. Fourth, S-SMase is able to hydrolyze the SM in atherogenic lipoproteins at neutral pH.[2+] Other possible roles for S-SMase may be in ceramide-mediated cell signalling, perhaps after reuptake of the secreted enzyme into endosomal vesicles (cf. Wiegmann et al., 1994; Cifone et al., 1995), in extracellular sphingomyelin catabolism after nerve injury and during demyelination (Schissel et al., 1996; Svensson et al., 1993; Bauer et al., 1994; Hartung et al., 1992), and in defense against viruses, many of which are enriched in SM (van Genderen et al., 1994; Aloia et al., 1988) and can be inactivated by treatment with SMase in vitro.

L- and S-SMase are very similar proteins. Cells transfected with an ASM cDNA overexpress both L-SMase and S-SMase (Schissel et al., 1996), indicating that S-SMase does not arise by alternative processing of the ASM gene. In addition, antibodies made against L-SMase recognize S-SMase, indicating that the common mRNA is translated in the same reading frame, and the molecular weights of the enzymes on Western blot are very close to one another (see Schissel et al., 1996). Nevertheless, S-SMase requires exogenously added $Zn^{2+}$ for activation in in-vitro assays whereas L-SMase does not (Schissel et al., 1996). In fact, the lack of stimulation of L-SMase by any cations and its lack of inhibition by EDTA has led to a long-standing body of literature labeling L-SMase as a "cation-independent" enzyme (Lebade et al., 1986).

What is the basis for this apparent difference in $Zn^{2+}$ dependency between L- and S-SMase? Data is presented herein to support the hypothesis that, in fact, both forms of the enzyme are zinc-activated enzymes. The $Zn^{2+}$-dependency of L-SMase has been overlooked because it is already saturated with $Zn^{2+}$ upon isolation from cell homogenates and thus does not respond to exogenous $Zn^{2+}$ at the time of assay. Furthermore, as is the case with known zinc-metalloenzymes (cf. Little et al., 1975), the $Zn^{2+}$ cannot be stripped from L-SMase by simple exposure to EDTA.

S-SMase escapes lysosomal targeting and travels through a secretory pathway that does not come into contact with intracellular stores of $Zn^{2+}$. Thus, this enzyme requires $Zn^{2+}$ during subsequent in-vitro assay. The information herein presented should prove useful for future studies that explore the enzymology and regulation of these important SMases and for the design of animal models to explore their functions in vivo.

Experimental Procedures

Materials—The FALCON® tissue culture plasticware used in these studies was purchased from FISHER® Scientific Co. (Springfield, N.J.). Tissue culture media and other tissue culture reagents were obtained from LIFE TECHNOLOGIES® (Baltimore, Md.). Fetal bovine serum (FBS) was obtained from HYCLONE LABORATORIES® (Logan, Utah) and was heat-inactivated for 1 h at 65° C. (HI-FBS). [9,10-$^3$H]Palmitic acid (56 Ci/mmol) was purchased from DUPONT NENS and [N-palmitoyl-9-10-$^3$H] Sphingomyelin was synthesized as previously described (Schissel et al., 1996; Sripada et al., 1987; Ahmad et al., 1985). (N,N)-Dimethylformamide; 1,3-dicyclohexylcarbodiimide; (N)-hydroxysuccinimide; and (N,N)-diisopropylethylamine were purchased from ALDRICH® Chemical Inc. Precast 4–20% gradient Dolyacrylamide gels were purchased from NOVEX® (San Diego, Calif.). Nitrocellulose was from Schleicher and Schuell (Keene, N.H.). FLAG-tagged S-SMase and rabbit anti-FLAG-tagged S-SMase was from (AMGEN®, Boulder, Colo.); the FLAG-tagged S-SMase was purified by anti-FLAG immunoaffinity chromatography from the conditioned medium of cells transfected with a human ASM-FLAG cDNA. Peroxidase-conjugated goat anti-rabbit IgG was purchased from PIERCE® Chemical Co. (Rockford, Ill.). The thiol-based metalloproteinase inhibitors, HS—$CH_2$—R—CH($CH_2$—CH($CH_3$)$_2$) —C)-Phe-Ala-NH, and HO—NH—CO—$CH_2$—CH($CH_2$CH($CH_3$)$_2$)—C)-Nal-Ala-NH—$CH_2$—$CH_2$—$NH_2$, were purchased from Peptides International, Inc. (Louisville, Ky.). β-endo-N-acetylglucosaminidase H (endo H) and peptide-N-glycanase F were purchased from Boehringer Mannheim. Bovine liver 215-kD mannose-6-phosphate receptor linked to Affigel 15 was made as described by Varki and Kornfeld (Varki et al., 1983). Sphingosylphosphorylcholine, 1,10-phenanthroline, and all other chemicals and reagents were from SIGMAS Chemical Co. (St. Louis, Mo.), and all organic solvents were from FISHER® Scientific Co.

Cells—Monolayer cultures of J774.A1 cells (from the American Type Culture Collection—see Khoo et al., 1989) were grown and maintained in spinner culture with DMEM/HI-FBS/PSG as described previously (Okwu et al., 1994; Khoo et al., 1989). Truman skin fibroblasts obtained from a patient with type A Niemann-Pick disease (R496L mutation Levran et al., 1991) were grown in DMEM/HI-FBS/PSG. CHO-KL cells were grown in Ham's F-12 containing 10% HI-FBS and PSG. CHO cells stably transfected with ASM cDNA were maintained in DMEM/HI-FBS/PSG (Schissel et al., 1996). Cells were plated in 35-mm (6-well) or 100-mm dishes in media containing HI-FBS for 48 h. The cells were then washed 3 times with PBS and incubated for 24 h in fresh serum-free media (1 ml and 6 ml per 35-mm and 100-mm dishes, respectively) containing 0.2% BSA. This 24-h conditioned medium was collected for SMase assays.

Harvesting of Cells and Conditioned Media—Following the incubations described above and in the figure legends, cells were placed on ice and the serum-free conditioned media was removed. The cells were washed two times with ice-cold 0.25 M sucrose and scraped into 0.3 ml and 3.0 ml of this sucrose solution per 35-mm and 100-mm dishes, respectively. Unless indicated otherwise, the scraped cells were disrupted by sonication on ice using three 5-second bursts (Branson 450 Sonifier), and the cellular homogenates were assayed for total protein by the method of Lowry et al. (Merrill et al., 1990) and for SMase activity as described below. The conditioned media were spun at 800×g for 5 min to pellet any contaminating cells and concentrated six-fold using a Centriprep 30 (Amicon; Beverly, Mass.) concentrator (molecular weight cut off=30,000). For the experiment in FIG. 18, CHO-K1 cells were incubated in 100-mm dishes in serum-free media and washed as described above. Cells were then scraped in 5 ml of 0.25 M sucrose and broken open under 500 psi of nitrogen pressure for 1.5 minutes using a nitrogen cell disruption bomb (Parr Instrument Company. Moline, Ill.). Following disruption, a portion of the cells was subjected to brief sonication as described above; this portion of cells is referred to as the cell homogenate. The remainder of disrupted cells was spun at 1300×g for 5 min to pellet any remaining intact cells and nuclei. This post-nuclear supernate (PNS) was collected, and the volume was increased to 15 ml with 0.25 M sucrose and then spun at 16,000×g for 30 min. The pellet from this centrifugation was resuspended in 1 ml of 0.25 M sucrose and sonicated as above, and this material, as well as the cell homogenate, were assayed for SMase activity.

SMase Assay—As previously described (Schissel et al., 1996), the standard 200-μl assay mixture consisted of up to 40 μl of sample (conditioned media or homogenized cells; see above) and a volume of assay buffer (0.1 M sodium acetate, pH 5.0) to bring the volume to 160 μl. The reaction was initiated by the addition of 40 μl substrate (50 pmol [$^3$H]sphingomyelin) in 0.25 M sucrose containing 3% Triton X-100 (final concentration of Triton X-100 in the 200-μl assay mix=0.6%). When added, the final concentrations of EDTA and $Zn^{2+}$ were 5 mM and 0.1 mm, respectively, unless indicated otherwise. The assay mixtures were incubated at 37° C. for no longer than 3 h and then extracted by the method of Bligh and Dyer (Bligh et al., 1959); the lower, organic phase was harvested, evaporated under $N_2$, and fractionated by TLC using chloroform:methanol (95:5). The ceramide spots were scraped and directly counted to quantify [$^3$H]ceramide. Typically, the assay reactions contained approximately 20 μg of cellular homogenate protein and a volume of conditioned media derived from a quantity of cells equivalent to approximately 50 μg of cellular protein.

SDS-Polyacrylamide Gel Electrophoresis and Immunoblotting—Protein samples were boiled in buffer containing 1% SDS and 10 mM dithiothreitol for 10 min, loaded onto 4–20% gradient polyacrylamide gels, and electrophoresed for 50 min at 35 milliamps in buffer containing 0.1% SDS (SDS-PAGE). Following electrophoresis, some gels were fixed in methanol/glacial acetic acid/water (5:2:3, v/v/v) and then silver-stained using reagents from BioRad (Hercules, Calif.). Other gels were electrotransferred (100V for 1.5 h) to nitrocellulose for immunoblotting. For immunoblotting, the nitrocellulose membranes were incubated with 5% Carnation nonfat dry milk in buffer A (24 mM Tris, pH 7.4, containing 0.5 M NaCl) for 3 h at room temperature. The membranes were then incubated with rabbit anti-FLAG-tagged S-SMase polyclonal antiserum (1:2000) in buffer B (buffer A containing 0.1% Tween-20, 3% nonfat dry milk, and 0.1% bovine serum albumin) for 1 h at room temperature. After washing four times with buffer A containing 0.1% Tween-20, the blots were incubated with horseradish peroxidase-conjugated goat anti-rabbit IgG (1:2000) for 1 h in buffer B at room temperature. The membranes were subsequently washed twice with 0.3% Tween-20 in buffer A and twice with 0.1% Tween-20 in buffer A. Finally, the blots were soaked in the enhanced chemiluminescence reagent (DuPont NEN®) for 2 min and exposed to X-ray film for 1 min.

Glycosidase Treatments—The procedure described by Hurwitz et al. (Hurwitz et al., 1994) was followed. CHO-K1 cells were incubated overnight with serum-free medium (CHO-S-SFM II from GIBCO). Fifty µg of 30-fold-concentrated conditioned medium and 50 µg of cell homogenate were diluted 1:1 (v/v) with 50 mM sodium acetate buffer, pH 5.0, containing 2% SDS and 20 mM β-mercaptoethanol (Hurwitz et al., 1994). One set of aliquots of the diluted conditioned medium and cell homogenate were treated for 16 h at 37° C. with 4 mU endo H. Another set of aliquots was diluted another 15-fold with 50 mM sodium phosphate buffer, pH 7.2, containing 1% Nonidet P-40, and treated for 16 h at 37° C. with 100 mU peptide-N-glycanase F. The endo H digest and a trichloroacetic-acid pellet of the peptide-N-glycanase F digest (Hurwitz et al., 1994) were boiled in SDS/dithiothreitol buffer and then electrophoresed and immunoblotted as described above.

Zinc-chelate Chromatography—We used a modification of the method of Hortin and Gibson (Hortin et al., 1989). Packed one-ml columns of chelating Sepharose 6B (iminodiacetic acid coupled to agarose gel via a hydrophilic spacer; from Pharmacia) were washed with 10 mM sodium acetate buffer, pH 6.0, containing 10 mM EDTA, to leave the column uncharged, or containing 60 mM $ZnCl_2$, to charge the column with $Zn^{2+}$. The columns were then equilibrated with 50 mM Hepes (N-2-hydroxyethylpiperazine-N'-2-ethanesulfonic acid) buffer, pH 7.4, containing 50 mM NaCl. One-ml samples of a 1:1 (v/v) mixture of this equilibration buffer and unconcentrated conditioned medium from ASM-transfected CHO cells (above) were loaded onto the columns and incubated for 15 min at room temperature. The columns were then washed with 7.5 ml of 50 mM Hepes, pH 7.4, containing either 100 mM NaCl or 1 M NaCl, which was collected as ten 0.75-ml fractions. The columns were eluted with 3.75 ml of 50 mM Hepes, pH 7.4, containing 50 mM EDTA plus 1 mM 1,10-phenanthroline, which was collected as five 0.75-ml fractions. Aliquots of each of the fractions were spotted on nitrocellulose using a slot-blot apparatus and then immunoblotted using goat anti-human L-SMase polyclonal antiserum as described above.

Statistics—Unless otherwise indicated, results are given as means±S.D. (n=3); absent error bars in the figures signify S.D. values smaller than the graphic symbols.

Results $Zn^{2+}$ requirement for S-smase does not involve a $Zn^{2+}$-dependent cofactor. One question was how L- and S-SMase acquire their apparent differences in zinc-dependency. One explanation would be that the secreted form requires a $Zn^{2+}$-dependent co-factor. Because many lysosomal enzymes undergo proteolytic activation (Hasilik, 1992), an obvious candidate for a $Zn^{2+}$-dependent co-factor would be a zinc-metalloproteinase. The results of five experiments, however, ruled out this possibility. First, $Zn^{2+}$-activated S-SMase can be subsequently inactivated by $Zn^{2+}$-chelation (see below); reversibility of $Zn^{2+}$-induced activation is not consistent with proteolytic activation. Second, inhibitors of zinc-metalloproteinases, such as tissue inhibitor of metalloproteinase-1 (TIMP-1) (Nagase et al., 1996) and two different thiol-based peptide inhibitors, HS—$CH_2$—R—CH($CH_2$—CH($CH_3)_2$)—C)-Phe-Ala-$NH_2$ and HO—NH—CO—$CH_2$—CH($CH_2CH(CH_3)_2$)—C)-Nal-Ala-NH—$CH_2$—$CH_2$—$NH_2$ (Panchenko et al., 1996), did not affect the ability of $Zn^{2+}$ to activate S-SMase. Third, mammalian zinc-metalloproteinases require $Ca^{2+}$ as well as $Zn^{2+}$, for activity (Reynolds, 1996), whereas $Ca^{2+}$ is not a requirement for the activation of S-SMase (Schissel et al., 1996). Fourth, comparison of $Zn^{2+}$-activated S-SMase from CHO cells with that of the intracellular (lysosomal) enzyme by immunoblot analysis showed that the activated secreted form had a somewhat higher, not lower, apparent $M_r$ (see control data in FIG. 16, below); in addition, S-SMase not activated with $Zn^{2+}$ had the same apparent $M_r$ as $Zn^{2+}$-activated S-SMase. Fifth, we found that highly purified S-SMase, obtained by either anti-FLAG immunoaffinity purification of a FLAG-tagged S-SMase or by concanavalin A chromatography followed by anti-SMase immunoaffinity purification of S-SMase from ASM-transfected CHO cells (Schissel et al., 1996), was ~95% $Zn^{2+}$-dependent. Thus, neither a zinc-metalloproteinase nor any other $Zn^{2+}$-dependent cofactor appears to be involved in the activation of S-SMase, suggesting direct activation of S-SMase by $Zn^{2+}$.

To further support this conclusion, a demonstration that S-SMase directly binds $Zn^{2+}$ by subjecting conditioned media from ASM-transfected CHO cells (Schissel et al., 1996) to zinc-chelate chromatography (cf. Hortin et al., 1989) was undertaken. None of the S-SMase from the conditioned medium bound to an uncharged column, whereas >95% of the S-SMase bound to a $Zn^{2+}$-charged column, even when washed with buffer containing 1 M NaCl; all of the bound material was eluted by EDTA plus 1,10-phenanthroline. These data and the previous data are consistent with the conclusion that S-SMase binds and is directly activated by $Zn^{2+}$.

Evidence for direct activation of L-SMase by $Zn^{2+}$— Despite the long-standing tenet that L-SMase is a cation-independent enzyme (Brady, 1983), it was hypothesized that L-SMase was a zinc-activated enzyme. First, L-SMase and S-SMase come from the same gene and same mRNA in the same reading frame (Schissel et al., 1996), and S-SMase binds and is directly activated by $Zn^{2+}$ (above). Second, there are seven amino acyl sequences in the enzyme that are homologous to $Zn^{2+}$-binding sequences in known zinc-metalloenzymes[4] (Valle et al., 1990), including one sequence that is very similar to that in another phosphodiesterase enzyme (Table 2). Third, L-SMase shares two other properties of known zinc-metalloenzymes, namely, inhibition by phosphate ions (Levade et al., 1986; Brady, 1983), which are thought to block the $Zn^{2+}$-binding pocket(s) in zinc-metalloenzymes (Hough et al., 1989), and inhibition by high concentrations (e.g., 6 mM) of $ZnCl_2$ (Reynolds, 1996; Spence et al., 1989).

To directly test whether L-SMase is a zinc-activated enzyme, chelation of $Zn^{2+}$ away from each enzyme in vitro was tried to determine the effect on catalytic activity. In fact, the conclusion by others that L-SMase is a cation-independent enzyme is based partly on the observation that EDTA does not inhibit activity (Schneider et al., 1967; Rao et al. 1976; Yamaguchi et al., 1977; Callahan t al., 1978; Bowser et al., 1978. Watanabe et al., 1983). Many zinc-metalloenzymes, however, bind the metal very tightly and thus require more potent chelation, such as by long-term incubation with the $Zn^{2+}$ chelator 1,10-phenanthroline (Little et al., 1975). To begin, studies were conducted with S-SMase. which was shown herein to bind and be directly activated by $Zn^{2+}$. In FIG. 14 A, conditioned medium from J774 macrophages was incubated with either EDTA or $Zn^{2+}$ (first two bars) and then assayed for SMase activity. The S-SMase is markedly activated by $Zn^{2+}$ (Schissel et al., 1996). An aliquot of $Zn^{2+}$-activated S-SMase was incubated for 18 h with EDTA plus 1,10-phenanthroline in an attempt to chelate the enzyme-bound $Zn^{2+}$. As shown in the third bar in FIG. 14A, this treatment resulted in an approximately 50% loss of activity; treatment with EDTA alone did not affect enzyme activity. Finally, the partially inactivated S-SMase was dialyzed against $Zn^{2+}$-containing buffer (fourth bar), which restored activity to the original level observed when $Zn^{2+}$ was added initially to the conditioned medium (compare fourth and second bars in FIG. 14A).

Next, cellular (i.e., lysosomal) SMase[3] (FIG. 14B) was examined. As reported (Levade et al., 1986; Brady, 1983; Schissel et al., 1996), and in contrast to the situation with the secreted enzyme, L-SMase in cell homogenates shows maximal activity without added $Zn^{2+}$ and is not inhibited by EDTA (first three bars of FIG. 14B). The original, active cellular enzyme (i.e., not exposed to exogenous $Zn^{2+}$ in vitro) was incubated with EDTA plus 1,10-phenanthroline for 8 h (fourth bar). This treatment resulted in almost total inactivation of the enzyme, and substantial activity was restored by dialyzing against $Zn^{2+}$ (fifth bar) or by directly adding back excess $Zn^{2+}$.[6] The actual degree of inhibition by chelation and re-activation by $Zn^{2+}$-dialysis differed somewhat between the secreted and cellular SMases, perhaps due to a lesser stability of the cellular enzyme under the incubation conditions employed. Nonetheless, the overall patterns of inhibition and reactivation shown in FIG. 14, together with the lines of evidence mentioned earlier, provide strong evidence that L-SMase, like S-SMase, is a zinc-activated enzyme.

The difference in requirement for $Zn^{2+}$ in the in-vitro assays of L- and S-SMase: differential $Zn^{2+}$-affinity versus differential exposure to cellular $Zn^{2+}$ prior to the assay— One possible explanation for the difference in $Zn^{2+}$-requirement in the in-vitro assays of L- and S-SMase is that the two enzymes would both be exposed to the same, though limiting, concentration of intracellular $Zn^{2+}$, but that the lysosomal enzyme would have a higher affinity for the cation, perhaps owing to a difference in post-translation modification. Thus, L-SMase would already have bound $Zn^{2+}$ at the time of the assay. The secreted enzyme would have lower affinity for $Zn^{2+}$, and thus excess exogenous $Zn^{2+}$ would have to be added for activation in vitro.

Figure 15:
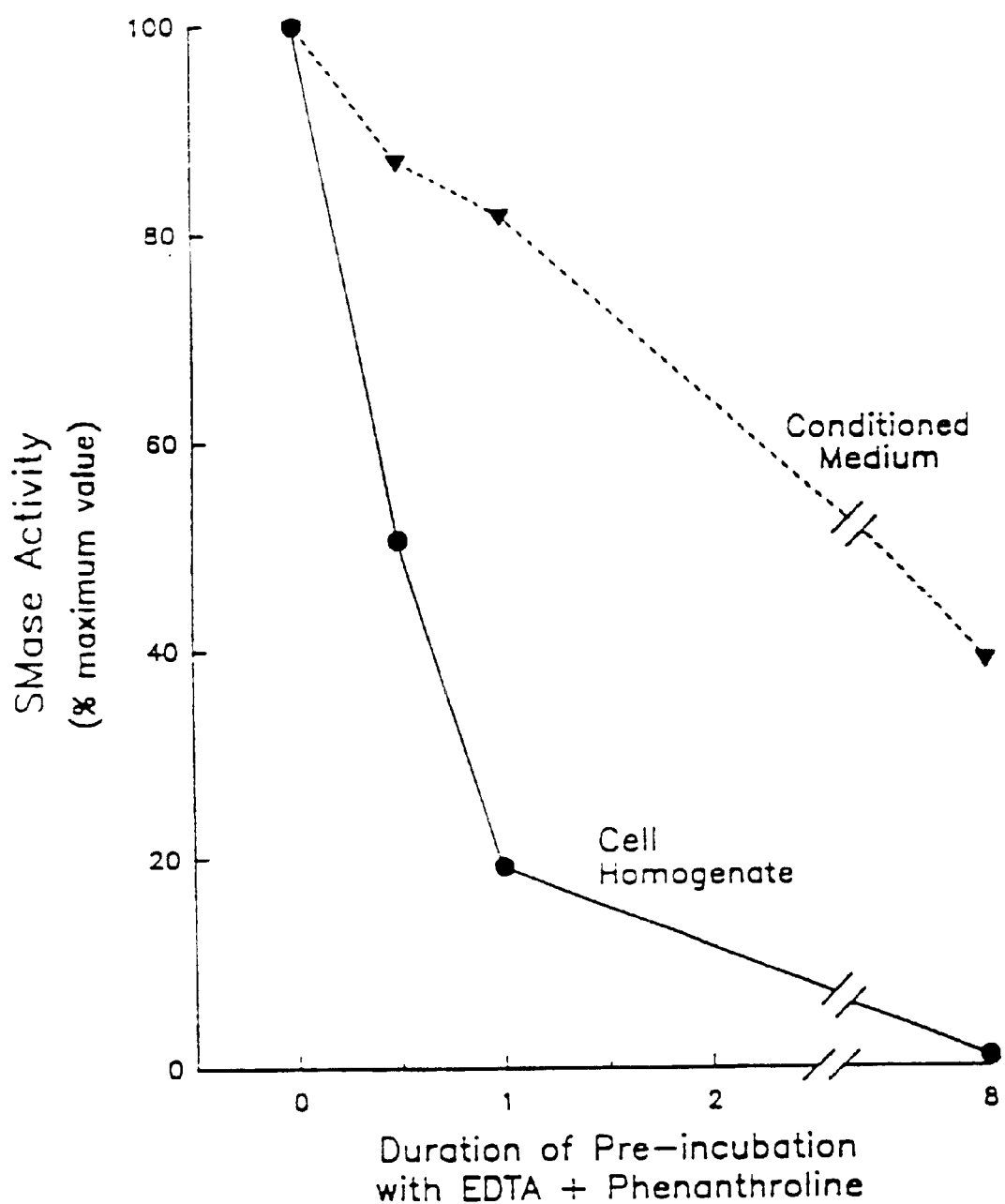
FIG. 15. Time-course of inactivation of secreted and intracellular SMase by $Zn^{2+}$-chelation. Serum-free conditioned medium, pre-activated by incubation with 0.1 mM $ZnCl_2$ at 37° C. for 10 min, and cell homogenate from J774 macrophages were incubated in the presence of 10 mM EDTA, 10 mM 1,10-phenanthroline, and 0.6% Triton X-100 at 4° C. for the indicated times. Each sample was then assayed for SMase activity in the presence of 5 mM EDTA for 1 h at 37° C. at pH 5.0. The maximum values (100% on the y-axis) for the cell homogenate and conditioned medium were, respectively, 72.0±0.3 and 17.1±0.3 pmol [$^3$H] ceramide/mg protein/h.

The relative $Zn^{2+}$-affinities of these two enzymes was estimated by assaying their inactivation as a function of increasing exposure to metal chelators (Little et al., 1975). Therefore, a cellular homogenate of J774 macrophages and the conditioned medium from these cells was incubated with EDTA plus the 1,10-phenanthroline for increasing times at 4° C. and then assayed these two fractions for SMase activity at each time point. Both enzymes lost activity with increasing duration of chelation (FIG. 15), whereas incubation in the absence of the chelators for 8 h at 4° C. resulted in no loss of either secreted or cellular SMase activity. Surprisingly, cellular SMase activity decreased at a greater rate and to a greater extent than secreted SMase activity, which is not consistent with the hypothesis that L-SMase has a higher affinity for $Zn^{2+}$ than S-SMase.

Figure 16:
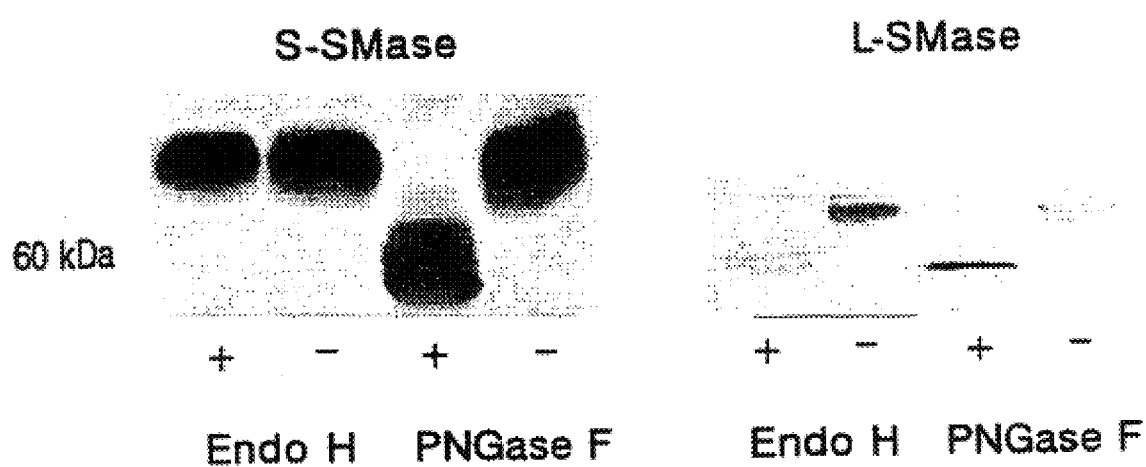
FIG. 16. Susceptibility of S- and L-SMase to endo H and peptide-N-glycanase F. Aliquots of concentrated conditioned media (as a source of S-SMase) and cellular homogenate (as a source of L-SMase) from CHO cells were incubated in the absence or presence of endo H or peptide-N-glycanase F (PNGase F) for 16 h at 37° C. and then subjected to SDS-PAGE. The electrophoresed proteins were transferred to a nitrocellulose membrane and then immunoblotted using rabbit anti-FLAG-tagged S-SMase anti-serum.

The other possibility is that both enzymes bind $Zn^{2+}$ with similar affinities, but only the lysosomal enzyme would be exposed to pools of intracellular $Zn^{2+}$ prior to the assay: this exposure to $Zn^{2+}$ could occur during transit to or residence in lysosomes and/or during preparation of the cell homogenate. Indeed, studies in many different cell types have shown that $Zn^{2+}$ is distributed in various intracellular organelles, including lysosomes (Bettger et al., 1981) and cytoplasmic vesicles (Sanscher et al., 1985). This model makes several assumptions and predictions that we tested experimentally. First, the idea that exposure of L-SMase to $Zn^{2+}$ could occur during transit to or residence in lysosomes assumes that S-SMase does not simply arise by exocytosis of lysosomal vesicles (cf. Ref. Hasilik, 1992). To directly test this important point, data was obtained on the carbohydrates of L- and S-SMase. The lysosomal targeting of L-SMase is typical for most lysosomal enzymes: acquisition of Asn-linked high-mannose oligosaccharides (Hurwitz et al. 1994; Newrzella et al., 1996) followed by phosphorylation of some of the mannose residues and shuttling from the trans-Golgi to late endosomes/prelysosomes via mannose-phosphate receptor-containing vesicles (Hasilik, 1992; Kornfeld, 1987). In the typical (i.e., non-lysosomal) secretory pathway, however, the original high-mannose oligosaccharides on the SMase would be expected to undergo processing to complex oligosaccharides during transit through the Golgi (Hurwitz et al., 1994; Hasilik, 1992; Newrzella et al., 1996; Kornfeld, 1987). Therefore, aliquots of conditioned medium and homogenates from untransfected CHO cells were incubated with endo H, which is specific for high mannose-type Asn-linked oligosaccharides (Yamamoto, 1994); other aliquots were incubated with peptide-N-glycanase F, which cleaves both high mannose and complex Asn-linked oligosaccharides (Yamamoto, 1994). These incubations were then analyzed by anti-SMase immunoblots. As shown in FIG. 16, S-SMase was completely resistant to endo H but susceptible to peptide-N-glycanase F. indicating the presence of complex-type Asn-linked oligosaccharides. In contrast, L-SMase was susceptible to both glycosidases, which confirms that this form of the enzyme has high mannose-type oligosaccharides. These data Indicate that S-SMase does not arise via exocytosis of lysosomes or vesicles in transit to lysosomes but rather through the typical secretory pathway. These distinctly divergent pathways provide the opportunity for one of the SMase to be exposed to different levels of cellular $Zn^{2+}$ than the other form of the enzyme.

Second, the model implies that it is the sequestration of S-SMase away from $Zn^{2+}$ in the lysosomal pathway, not the oligosaccharide processing of S-SMase per se, that confers $Zn^{2+}$-dependency on S-SMase. To test this idea, a system in which cells secreted S-SMase that was mannose-phosphorylated but not exposed to the lysosomal pathway was investigated. In transfected cells that massively overexpress a lysosomal enzyme, a substantial portion of the mannose-phosphorylated form of this enzyme saturates the mannose-6-phosphate receptor shuttling mechanism (Ioannou et al., 1992). Therefore, these cells secrete lysosomal enzymes that are mannose-phosphorylated but that have not been exposed to the lysosomal targeting pathway or to lysosomes (Ioannu et al., 1992). Indeed, ~80% of S-SMase from ASM-transfected CHO cells bound to a mannose-6-phosphate receptor affinity column and could be eluted with mannose-6-phosphate (cf. Faust et al., 1987). This secreted SMase was 98% $Zn^{2+}$-dependent, while the lysosomal SMase in these cells required no added $Zn^{2+}$ when assayed in cellular homogenates. Thus, even though the S-SMase from these overexpressing cells underwent the typical carbohydrate modifications of a lysosomal, not a secretory, enzyme, it had the same degree of $Zn^2+$-dependency seen with S-SMase from non-transfected cells. This finding is consistent with the model herein, since the S-SMase from these cells bypassed lysosomal targeting and thus would not be exposed to cellular pools of These data demonstrate that $Zn^{2+}$-dependent secreted SMase can become maximally activated by exposure to intracellular pools of $Zn^{2+}$ during internalization, intracellular sorting, and/or cellular sonication. Once sonic disruption of the cells is completed, however, these pools of $Zn^{2+}$ are too diluted to activate the enzyme, since simply adding S-SMase to sonicated cell homogenates does not reduce the $Zn^{2}$-dependency of the enzyme.

Figure 18B:
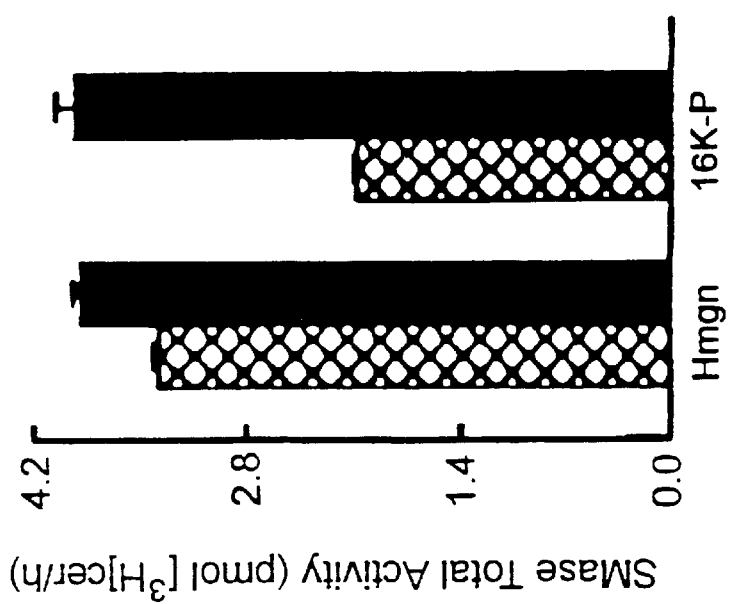
FIGS. 18A–B. $Zn^{2+}$-dependency of SMase in a sonicated cell homogenate and 16,000-x-g pellet. CHO cells were grown to 90% confluency in Ham's F-12 media containing 10% HI-FBS and PSG and then washed 3 times with PBS before incubation in serum-free medium containing 0.2% BSA for 24 h. The cells were then washed 3 times in 0.25 M sucrose and the total cell homogenate and the 16,000-x-g cellular subfraction were isolated as described in "Experimental Procedures". Twelve micrograms of the cell homogenate (Homogenate) and 2.5 μg of the 16,000-x-g pellet (16K-xg Pellet) were assayed for SMase activity in the presence of either 5 mM EDTA (hatched bars) or 0.1 mM $ZnCl_2$ (solid bars) for 1 h at 37° C. at pH 5.0. The main graph displays specific enzymatic activities, and the inset shows total SMase activity in the cell homogenate (Hmgn) and the 16,000-x-g pellet (16K-P).
Figure 18A:
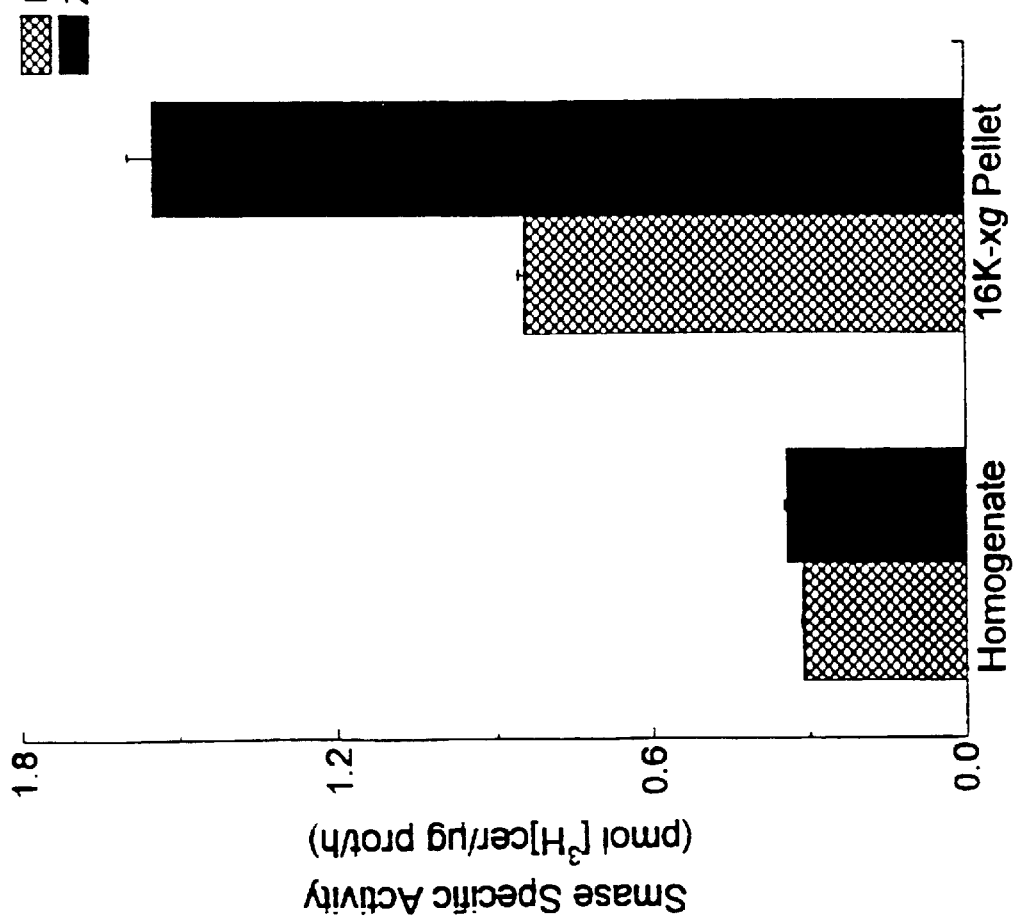

The $Zn^{2+}$-dependency of L-SMase and previous work demonstrating discrete intracellular $Zn^{2+}$ pools that can change under certain metabolic conditions (cf. Csermely et al., 1987; Brand et al., 1996) led us to consider the hypothesis that $Zn^{2+}$ availability to lysosomes and to L-SMase might be involved in the regulation of this enzyme. A prediction of our hypothesis is that L-SMase may not always be maximally stimulated by intracellular $Zn^{2+}$. In the standard L-SMase assay, transfected CHO cells are completely homogenized (by sonication), and the cell homogenate is assayed. Under these conditions, the enzyme is maximally activated, and exogenous $Zn^{2+}$ has no effect (FIG. 18A). To obtain a less damaged lysosomal preparation, a separate aliquot of these CHO cells was disrupted under 500 psi of nitrogen pressure for 1.5 min, and a 16,000-x-g pellet was isolated, which consists of intact lysosomes, as well as mitochondria and peroxisomes (cf. Watanabe et al., 1983). This 16,000-x-g pellet was then sonicated and assayed for SMase activity. Remarkably, under these conditions, the enzyme was only ~50% activated and was substantially stimulated by exogenous $Zn^{2+}$ (FIG. 18B). Thus, L-SMase encounters sub-saturating levels of $Zn^{2+}$ during transit to lysosomes and/or after subsequent storage there. In contrast, when the cells are disrupted by sonication, nearby intracellular pools of $Zn^{2+}$ are released, which leads to saturation of the enzyme with $Zn^{2+}$ prior to dissipation of these pools throughout the entire homogenate. Thus, in the standard In-vitro assay, which uses sonicated whole-cell $Zn^{2+}$.

Figure 17:
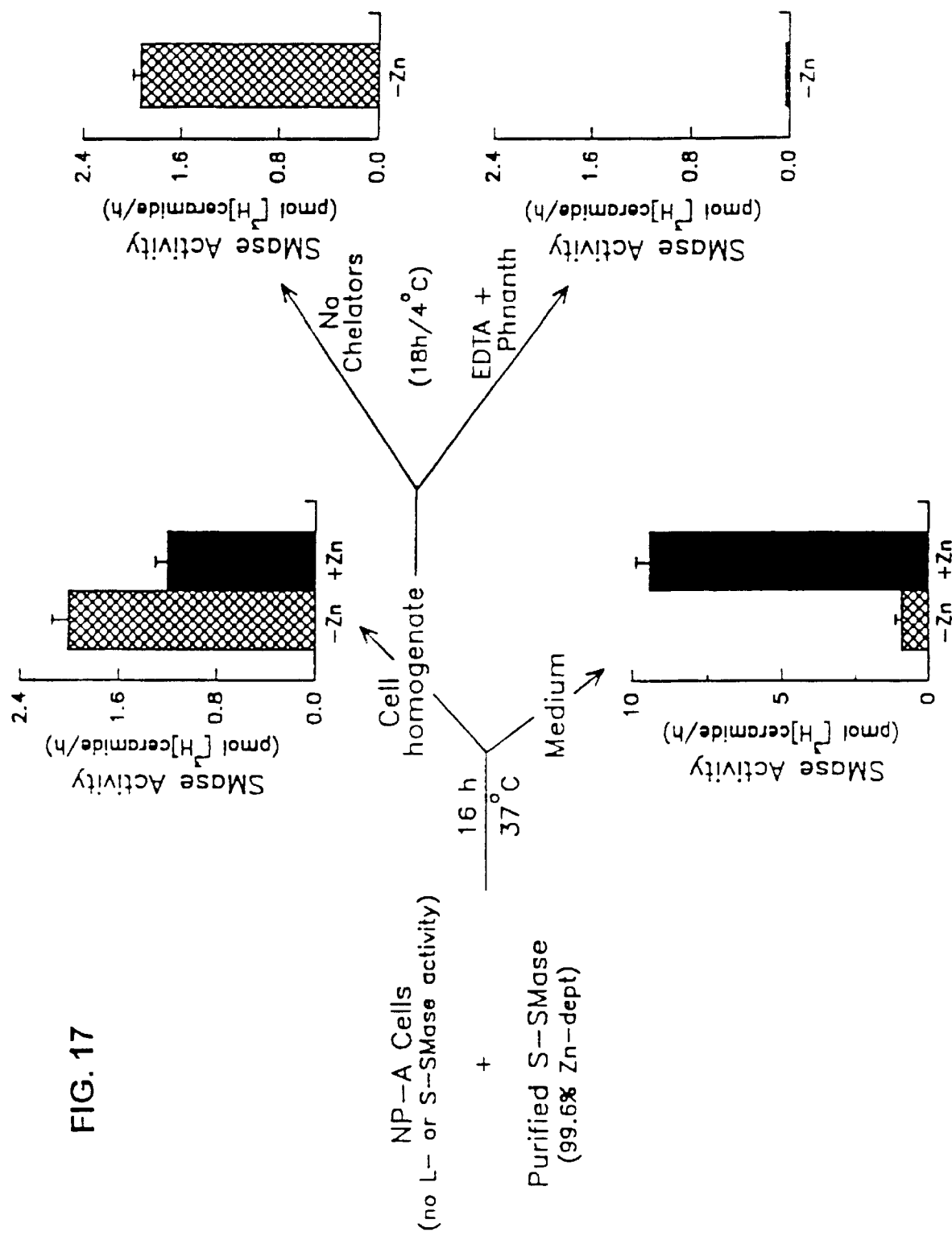
FIG. 17. $Zn^{2+}$-dependency of S-SMase after internalization by type A Niemann-Pick cells. Skin fibroblasts from a patient with type A Niemann-Pick disease (NP-A Cells) were grown to 90% confluency in medium supplemented with 10% HI-FBS. The cells were then washed three times with PBS and incubated in serum-free media containing 0.2% BSA and 850 ng immunoaffinity-isolated FLAG-tagged S-SMase (Purified S-SMase)/ml at 37° C. for 16 h. The cell homogenate and incubation medium were then prepared as described in "Experimental Procedures", and aliquots were assayed for SMase activity in the presence of either 5 mM EDTA (hatched bars) or 0.1 mM $ZnCl_2$ (solid bars) for 2 h at 37° C. at pH 5.0. Other aliquots of the cell homogenate were incubated in the presence of 0.6% Triton X-100 alone (No Chelators) or in the presence of 10 mM EDTA, 10 mM 1,10-phenanthroline, and 0.6% Triton X-100 (EDTA+Phnanth) for 18 h at 4° C. and then assayed for SMase activity in the presence of 5 mM EDTA. All values are total SMase activity in each sample.

Third, the model predicts that secreted, $Zn^{2+}$ dependent S-SMase, when endocytosed by cells and delivered to lysosomes. would be exposed to cellular $Zn^{2+}$ and thus no longer require exogenously added $Zn^{2+}$. To test this prediction, highly purified secreted FLAG-tagged SMase, which is 99.6% $Zn^{2}$-dependent, and fibroblasts from a patient with type A Niemann-Pick disease, which completely lack both L- and S-SMase were used (Schissel et al., 1996). To introduce the FLAG-S-SMase into intact Niemann-Pick fibroblasts, the enzyme was added to media on living cells and then incubated for 16 h at 37° C. It was found that these cells can endocytose S-SMase and target it to lysosomes in a catalytically active form, as evidenced by a substantial reduction in lysosomal SM mass, which otherwise accumulates in these mutant fibroblasts (cf. Hurwitz et al., 1994; Neufeld, 1980). After the incubation, media and cells were harvested, cells were homogenized, and the media and sonicated cell homogenates were assayed for SMase activity (FIG. 17). As expected, the SMase activity that remained in the media (i.e., the portion of the enzyme that was not internalized) was almost entirely $Zn^{2+}$-dependent. In contrast, the SMase activity in the sonicated cell homogenates, which originated entirely via internalization of the exogenously added secretory enzyme, was maximally activated in the absence of $Zn^{2+}$ (FIG. 17). Addition of $Zn^{2+}$ not only failed to increase the cellular enzymatic activity, but for unclear reasons produced a somewhat lower activity. To demonstrate that the $Zn^{2+}$-independent SMase activity in the cell homogenates was due to exposure of the enzyme to cellular pools of $Zn^{2+}$, homogenates were subsequently incubated for 24 h with EDTA plus 1,10-phenanthroline, to chelate $Zn^{2+}$ (see FIGS. 1 and 2), or with buffer alone as a control. As shown in FIG. 17, the cellular SMase activity was specifically inhibited by $Zn^{2+}$ chelation. Similar results were obtained when the Niemann-Pick cells were incubated with native (i.e., non-FLAG-tagged) S-SMase. homogenates, L-SMase is fully saturated with $Zn^{2+}$. These findings raise the intriguing possibility that the activity of L-SMase in intact cells may be subject to regulation by changes in the concentration or availability of $Zn^{2+}$ in lysosomes.

Discussion

Figure 19:
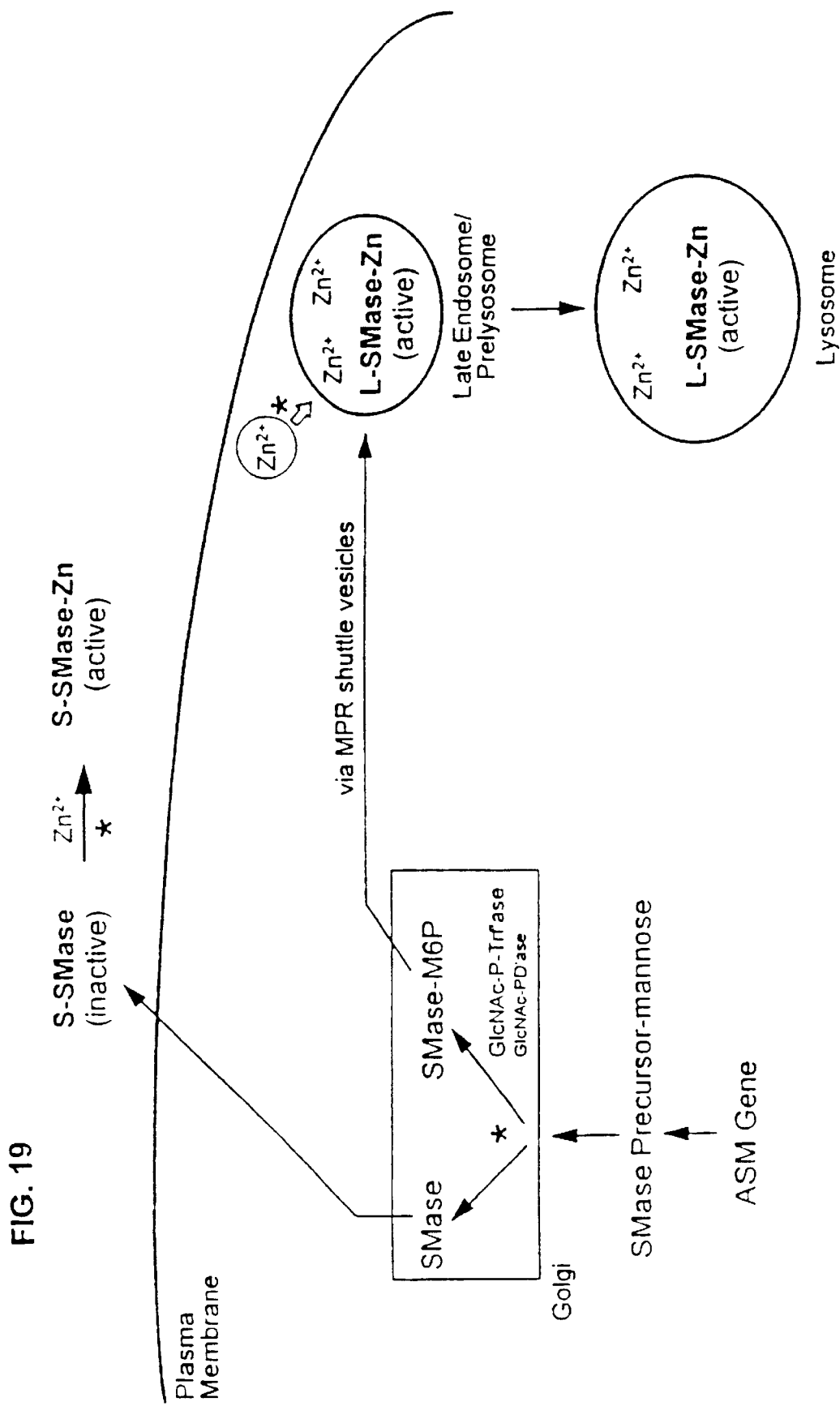
FIG. 19. Model of cellular pathways giving rise to lysosomal and secreted SMase. The ASM gene gives rise to a common mannosylated precursor protein (SMase Precursor-mannose) that gets shuttled into either the lysosomal trafficking pathway (SMase-M6P) or the secretory pathway (SMase) (see data in FIG. 16). According to the model, the enzyme is exposed to cellular pools of $Zn^{2+}$ in the lysosomal pathway but not in the secretory pathway. As is evident from the data in FIG. 18, however; L-SMase may not always be fully saturated with $Zn^{2+}$. Potential sites of regulation are marked by the asterisks; in addition, based upon data with S-SMase from endothelial cells, it is possible that a portion of S-SMase may acquire some $Zn^{2+}$ prior to secretion. In this diagram, $Zn^{2+}$-enrichment of late endosomes/prelysosomes is shown, which are the acidic vesicles where lysosomal enzymes are initially delivered and where hydrolysis by these enzymes can occur. It is possible, however, that mature lysosomes, in addition to or instead of prelysosomes, are enriched with $Zn^{2+}$. GlcNAc-P-Trf'ase, N-acetylglucosamine-1-phosphotransferase; GlcNAc-PD'ase, N-acetylglucosamine phosphodiesterase; M6P, mannose-6-phosphate; MPR, mannose-6-phosphate receptor.

A model to explain the apparent difference in $Zn^{2+}$-dependency of L-SMase versus S-SMase is shown in FIG. 19. The ASM gene (gives rise to a common precursor protein (Schissel et al. 1996), which is then modified by typical high-mannose oligosaccharide residues (Hurwitz et al., 1994; Newrzella et al., 1996; Kornfeld, 1987). This mannosylated precursor then traffics into either the lysosomal or the secretory pathway. In the lysosomal pathway, the SMase undergoes modification and trafficking that is typical for lysosomal enzymes: acquisition of mannose-phosphate residues by the sequential action of N-acetylglucosamine-1-phosphotransferase and N-acetylglucosamine phosphodiesterase on the mannose residues of the precursor (FIG. 16 and Hurwitz et al., 1994; Kornfeld, 1987). Vesicles containing mannose-phosphate receptors then shuttle this modified SMase to late endosomes/prelysosomes (Kornfeld, 1987), and at some point along this pathway the enzyme encounters cellular $Zn^{2+}$ and thus becomes at least partially activated. As mentioned in the Results section, L-SMase appears to be exposed to subsaturating concentrations of $Zn^{2+}$ in lysosomes and thus potentially subject to regulation by changes in $Zn^{2+}$ availability.

L-SMase has been studied for many years, particularly in the context of its absence in a human disease, namely types A and B Niemann-Pick disease (Levade et al., 1986; Brady, 1983). Throughout this period of study, the enzyme has been reported to be "cation-independent" (Levade et al., 1986; Brady, 1983). The data in this report strongly support the conclusion that this enzyme is, indeed, a zinc-activated enzyme. The reason why this fundamental property of this widely studied enzyme has been overlooked is because the enzyme at the time of isolation from whole-cell homogenates, which has been the source of L-SMase for the previous studies (Schneider et al., 1967; Rao et al., 1976; Yamaguchi et al., 1977; Callahan et al., 1978: Bowser et al., 1978: Watanabe et al., 1983), is already tightly bound to $Zn^{2+}$. Thus, exogenous $Zn^{2+}$ is not needed for the in-vitro assay, and typical short-term EDTA chelation incubations will not strip the enzyme of its metal, which has been reported for known zinc-metalloenzymes (Little et al., 1975).

To explain the origin of S-SMase, a portion of the common precursor, via a potentially regulated process, bypasses N-acetylglucosamine-1-phosphotransferase and thus is directed into the secretory pathway, not the lysosomal targeting pathway (Kornfeld, 1987) (FIG. 19). The difference in susceptibility of S- and L-SMase to endo H (FIG. 16) provide direct support for this component of the model. Importantly, the data suggest that SMase in the secretory pathway is not exposed to pools of cellular $Zn^{2+}$, thus explaining the requirement for exogenously added $Zn^{2+}$ when the secreted enzyme is assayed in vitro. As mentioned in the Results section, however, the subcellular location of $Zn^{2+}$ may be subject to cell-type variation or regulation (Bettger et al., 1981; Csermely et al., 1987; Brand et al., 1996). Therefore, it is possible that S-SMase may, under certain circumstances or in certain cell types, be fully or partially $Zn^{2+}$-independent. In fact, it was observed that SMase secreted by endothelial cells, unlike that secreted by macrophages (Schissel et al., 1996), is active in the absence of $Zn^{2+}$ and stimulated only two-fold by exposure to exogenous $Zn^{2+}$.[2]

According to this model, the key step that would determine the fate of SMase is catalysis of the common mannosylated precursor by N-acetylglucosamine-1-phosphotransferase. Extensive work by Kornfeld and colleagues (Baranski et al., 1992; Cantor et al., 1992; Dustin et al., 1995) has shown that N-acetylglucosamine-1-phosphotransferase recognizes a particular three-dimensional structure of lysosomal enzyme precursors, and induced modifications that alter this structure can have profound effects on lysosomal enzyme modification and targeting. Moreover, these workers have found that at least one enzyme, bovine DNase I, is a suboptimal substrate for the phosphotransferase, thus presumably giving rise to both intralysosomal and secretory forms. If the enzymes that undergo secretion by this mechanism can function at neutral pH ksee below) or if the cells are in an acidic environment, this process may enable cells to acquire two groups of functions from a single enzyme, namely, functions in lysosomes and functions in the extracellular milieu. In the case of S-SMase, there is an additional requirement for extracellular $Zn^{2+}$, which is known to exist in sufficient extracellular concentrations in vivo to activate the enzyme (cf. Schissel et al., 1996; Spence et al., 1989). Interestingly, certain cytokines increase the secretion of SMase from endothelial cells without affecting L-SMase activity, suggesting that the phosphotransferase reaction or perhaps another critical step responsible for determining the fate of SMase may be subject to specific regulation.

The current data and previous work by others (Callahan et al., 1983) indicate difficulties with the prior nomenclature of these SMases. First, both forms of the enzymes are zinc-activated enzymes, and so previous designation of the secreted form as "Zn-SMase" (Schissel et al., 1996) is obsolete. Second, the "acid SMase" nomenclature reflects the acid pH optima of the lysosomal and secreted forms of the enzyme in standard in-vitro detergent-based micellar assays and the ability of the lysosomal form to function in the acid environment of lysosomes (Levade et al., 1986). Kinetic studies. however, have shown that acid pH is needed only for proper interaction of the enzyme with the SM in these micelles (i.e. $K_2$) and that $V_{max}$ for hydrolysis is relatively pH-independent (Callahan et al., 1983). Furthermore, it was recently demonstrated that S-SMase can hydrolyze the SM of certain lipoproteins quite well at neutral pH.[3+] Thus, the SM in certain physiological substrates may be in an orientation that allows ready interaction with the enzyme at neutral pH, which, based upon the above-mentioned kinetic data, would then result in neutral SM hydrolysis. For these reasons, and since lysosomes and conditioned media of cells contain no other known SMase activity (Levade et al., 1986; Brady, 1983; Schissel et al., 1996; Horinouchi et al., 1995; Otterbach et al., 1995), the nomenclature herein (L-SMase and S-SMase) is preferred. To maintain consistency with prior literature, however, we still refer to their common gene of origin as the "ASM" gene.

The original impetus for the current mechanistic study was evidence supporting a role for an extracellular arterial-wall SMase in atherogenesis (u et al., 1991; Tabas et al., 1993; Schissel et al., 1996; Schuchman et al., 1991). S-SMase is a leading candidate for this arterial-wall activity. Furthermore, it is theoretically possible that S-SMase plays roles in cell-signalling processes, in extracellular SM catabolism in the central nervous system, and in anti-viral host defense mechanisms. In this context, the information reported herein on the molecular and cellular origin of S-SMase should prove useful in further regulatory studies on this enzyme and in designing strategies to test the role of this enzyme in atherogenesis and possibly other physiologic and pathophysiologic processes.

Footnotes

1. The abbreviations used are: ASM, acid sphingomyelinase; CHO, Chinese hamster ovary; DMEM, Dulbecco's modified Eagle's medium; endo H, β-endo-N-acetylglucosaminidase H; FBS, fetal bovine serum; HI-FBS, heat-inactivated FBS; LDL, low-density lipoprotein; L-SMase, lysosomal sphingomyelinase; PBS, phosphate-buffered saline; PSG, penicillin, streptomycin, & glutamine; SDS-PAGGE sodium dodecylsulfate polyacrylamide gradient-gel electrophoresis SM, sphingomyelin; SMase, sphingomyelinase; S-SMase, secreted sphingomyelinase; TIMP-1, tissue inhibitor of metalloproteinase-1; TLC, thin-layer chromatography.

4. The term "zinc-metalloenzyme", while often used to describe enzymes directly activated by $Zn^{2+}$, should be formally reserved for enzymes that have been purified to homogeneity and shown by atomic absorption spectroscopy or X-ray crystallography to contain one or more moles of zinc per mole of enzyme (Vallee et al., 1990). In this report, the term "zinc-activated" was used to describe current knowledge of S- and L-SMase, namely, $Zn^{2+}$-dependence of catalytic activity. The presence of zinc-binding motifs in the amino acyl sequence of these enzymes, together with the S-SMase data showing binding to the zinc-chelate column and absence of co-factor involvement, suggest that these enzymes are, indeed, "zinc-metalloenzymes", but this designation must await detailed structural studies.

5. Consistent with prior literature (cf. Brady, 1983) SMase activity in whole-cell homogenates using the standard acidic micellar assay, particularly when EDTA is added, has been equated with "lysosomal" SMase activity. Other types of cellular SMase are not active at acidic pH in this assay, and one of these other SMases also requires $Mg^{2+}$ for activity (Brady, 1983).

6. In experiments, it was found that 1,10-phenanthroline alone was not as effective as EDTA plus phenanthroline in inhibiting the activity of S- and L-SMase. One possible explanation is that the enzymes bind another divalent cation in addition to $Zn^{2+}$, and removal of this cation by EDTA facilitates the removal of $Zn^{2+}$ by 1,10-phenanthroline (cf. Little et al., 1975; Spence et al., 1989). Whatever the mechanism, the fact that 1,10-phenanthroline alone does not inhibit S- or L-SMase argues against an unlikely, though formally possible, alternative interpretation of the data in FIG. 14, namely, that 1,10-phenanthroline is a direct SMase inhibitor that becomes inactive as an inhibitor when the compound binds $Zn^{2+}$.

TABLE 2

Comparison of amino acid sequences of portions of L/S-SMase with known $Zn^{2+}$-binding consensus sequences of zinc-metalloenzymes [a]

| Enzyme | Amino acid sequence |
|---|---|
| L/S-SMase (282) [b] | H—(X)$_3$—H—(X)$_{33}$—E [c] |
| L/S-SMase (421) | H—(X)$_3$—H—(X)$_{21}$—E |
| Astracin zinc-protease gene family | H—(X)$_3$—H—(X)$_n$—E (n = 21, 28, 35) |
| cGMP-specific phosphodiesterase | H—(X)$_3$—H—(X)$_{24}$—E |
| Thermolysins & B. Cereus neutral protease | H—(X)$_3$—H—(X)$_{19}$—E |
| L/S-SMase (221) | C—(X)4-C—(X)$_{23}$—C—(X)$_2$—P |
| Aspartate transcarbamoylase | C—(X)$_4$—C—(X)$_{22}$—C—(X)$_2$—C |
| L/S-SMase (136) | H—(X)$_2$—E—(X)$_{142}$—H |
| L/S-SMase (459) | H—(X)$_2$—E—(X)$_{115}$—H |
| Carboxypeptidase A & B | H—(X)$_2$—E—(X)$_{123}$—H |
| L/S-SMase (575) | H—(X)$_2$—H—(X)$_{30}$—H |
| DD carboxypeptidase | H—(X)$_2$—H—(X)$_{40}$—H |
| L/S-SMase (457) | H—(X)—H—(X)$_{118}$—H |
| β-lactamase | H—(X)—H—(X)$_{121}$—H |

[a] L/S-SMase refers to the common amino acid sequence of L- and S-SMase, derived from the ASM cDNA (Schuchman et al., 1991); the sequences of the other enzymes are from Ref. (Vallee et al., 1990), except those of the astracin gene family, which is from Ref. (Hung et al., 1997), and of cGMP-specific phosphodiesterase, which is from Ref. (Francis et al., 1994).
[b] The number in parentheses represents the position of the first amino acid (H or C) of the SMase sequences displayed.
[c] X refers to any amino acid.

EXAMPLE 4

Role of Macrophage-Secreted $Zn^{2+}$-Stimulated Sphingomyelinase in Atherogenesis Focal retention of lipoproteins in the subendothelium is a key step in both the initiation and propagation of atherosclerotic lesions (reviewed in Williams and Tabas, 1–995)). Retained lipoproteins undergo marked aggregation (Nievelstein et al., 1991; Hoff and Morton, 1985), which is important for two major reasons: (1) aggregation of lipoproteins greatly increases the amount of lipoprotein retained (Tabas et al., 1993) and thus increases the atherogenic responses to this retained material; and (2) aggregated lipoproteins are potent stimulators of macrophage foam cell formation (Hoff et al., 1990; Khoo et al, 1988; Suits et al., 1989; Xu and Tabas, 1991), greatly exceeding the potency of oxidized LDL in inducing macrophage cholesteryl ester loading (Hoppe et al., 1994). Macrophage foam cells themselves have been shown to be very important in early lesion development (Smith et al., 1995) and probably also play a major role in late lesion complications, such as plague rupture (Libby and Clinton, 1993). Thus, interventions directed at blocking subendothelial lipoprotein aggregation may be anti-atherogenic at both early and late stages of lesion development. Furthermore, their mechanism of action would be strongly complementary to the currently available statins, which lower serum LDL levels. Along these lines, it should be noted that although the use of statins alone has led to decreased risk of both primary and secondary coronary artery disease, the risk reduction is far from complete. Therefore, the addition of another agent whose mechanism of action is complementary to that of lipid-lowering agents would be expected to have a major beneficial impact on the large number of patients with "statin-resistant" ischemic heart disease (Crouse, 1984).

Sphingomyelinase-Induced LDL Aggregation

Hydrolysis of a relatively small portion of the sphingomyelin content of LDL, using a commercially available bacterial sphingomyelinase (SMase), leads to aggregation of LDL which morphologically resembled aggregates seen in atheromata. These SMase-induced LDL aggregates were potent stimulators of macrophage foam cell formation. Furthermore, SMase was able to enhance LDL retention by 100-fold in a tissue culture model that utilized components thought to be involved in LDL retention in lesions, namely, smooth muscle cell-derived extracellular matrix and the lipoprotein lipase. When macrophages were added to this tissue culture model, massive foam cell formation was seen (Tabas et al., 1993). Thus, in vitro, SMase-induced LDL aggregation resulted in the two consequences described above—foam cell formation and enhanced LDL retention.

The role of SMase in LDL aggregation is enzymatic, not structural (Schissel et al, 1994). Thus, although initial experiments used bacterial SMase, similar results can be expected for mammalian SMases. Second, SMase-induced LDL aggregation was due to an increase in LDL ceramide content, not to low LDL sphingomyelin content or to the generation of choline-phosphate (Schissel et al., 1994). In fact, sphingomyelin enrichment of particles was shown to enhance subsequent SMase-induced aggregation. This was an important finding, since aggregation that depends on a low LDL SM content could not be physiologically significant: lesional LDL is enriched in SM. Overall, the mechanistic studies support a role for arterial-wall SMase in LDL trapping and aggregation.

The next question was whether LDL extracted from human and rabbit atherosclerotic lesions is enriched in ceramide Using both early and late human and rabbit atheromatous material, lesion LDL is markedly enriched in ceramide. whereas plasma LDL has very little ceramide. [$^3$H]sphingomyelin-labeled LDL was incubated with strips of rabbit aorta ex vivo. A portion of the labeled LDL was retained by the aorta, and this material was extracted and found to have a substantial amount of [$^3$H]ceramide. The hydrolysis of the LDL-sphingomyelin was enhanced in lesional vs. normal aorta, was not inhibited by chloroquine sand thus deed not involve lysosomal SMase), and was inhibited by EDTA. Thus, in both humans and rabbits, retained LDL is acted upon by an arterial wall non-lysosomal, cation-dependent SMase activity.

To look for such an activity, a determination of whether cell types prominent in lesions could secrete a Smase was done. In a remarkable series of experiments, it was demonstrated that both murine and human macrophages secrete an abundant $Zn^{2+}$-stimulated sphingomyelinase activity. This macrophage-secreted Zn-SMase has properties identical to a SMase described in 1989 by Spence et al. These workers found the enzyme in fetal calf serum, and there have been no follow-up studies since this original report; the cellular source of their enzyme remained a mystery until this recent discovery. Follow-up studies of the discovery revealed the following: (1) Zn-SMase is markedly up-regulated during monocyte-to-macrophage differentiation; (2) Zn-SMase has an acidic pH optimum using sphingomyelin-detergent micelles as substrate; (3) Zn-SMase can hydrolyze LDL-SM at physiological pH, in the presence of subendothelial factors such as extracellular matrix and lipoprotein lipase (see above); and (4) Zn-SMase is secreted by other cells, including brain-derived microglial cells.

The acidic pH optimum of Zn-SMase when sphingomyelin-detergent micelles were used as substrate prompted us to question whether this enzyme originated form the same gene as acidic lysosomal SMase (lys-SMase). Zn-SMase activity was measured in peritoneal macrophages from wild-type mice and mice that were made to lack one or both acid SMase genes by gene targeting. Remarkably, macrophages from the heterozygous knockout mice had half the normal amount of secreted Zn-SMase activity, and those from the homozygous knockout mouse secreted no Zn-SMase. Further studies revealed that CHO cells stably transfected with lys-SMase cDNA massively overexpressed both intracellular lysosomal SMase activity and secreted Zn-SMase activity. Lastly, when conditioned media cell extracts were mixed, neither the mounts nor the properties of the two SMases were altered, suggesting that cellular or secreted co-facto interaction with the enzymes cannot explain their differences. Thus, secreted Zn-SMase arises from the same gene as lys-SMase and arises by post-translational modification of the lysosomal enzyme. Studies are currently in progress to determine the exact molecular differences between the two SMases and to elucidate the intracellular pathway that converts lys-SMase into Zn-SMase.

Screening of Inhibitors for Zn-SMase and Testing in vitro and in vivo

One embodiment of the present invention is to identify an inhibitor of Zn-SMase and determine whether it is anti-atherogenic in animal models of atherosclerosis. First, a high throughput assay will need to be developed. The source of Zn-SMase activity will be conditioned media from macrophages or transfected CHO cells (see above). There are colorometric assays for acid SMases available and these will need to be tested using secreted Zn-SMase. If necessary, to avoid contaminating activities, a partially purified preparation of Zn-SMase, such as by passing the conditioned media over a sphingosylphosphorylcholine column, can be used as a source of enzyme for these inhibition assays. Once a rapid assay is identified and verified, screening can begin using compounds derived from libraries or other sources. Positive hits would be tested in a more detailed assay that would assess potency, specificity (e.g., Zn-SMase vs. lys-SMase vs. other Zn-requiring enzymes), and mechanism of action. Even compounds that can not distinguish between Zn-SMase and lys-SMase may be useful if they are unable to enter lysosomes or become inactive at acid pH.

Specific and potent Zn-SMase inhibitors will then be tested in a cell-culture system. In this system, smooth muscle cells, lipoprotein lipase, LDL, and macrophages will be coincubated in an attempt to reproduce the synergistic interactions described above for exogenously added bacterial SMase and macrophage conditioned media. The goal will be to establish a "self-sufficient" model of subendothelial LDL retention, aggregation, and foam cell formation. Once established, the Zn-SMase inhibitors will be tested for their ability to block these events. Other responses to retention and aggregation, such as LDL oxidation and monocyte chemotaxis & adhesion, could be modeled by adding an endothelial cell monolayer via a Transwell insert. Inhibition of these responses by Zn-SMase inhibitors would then be tested as above.

The effect of these agents may be tested in animal models of atherosclerosis. The two models that will be used are fat-fed apo B transgenic mice (Purcell-Huynh et al., 1995) and Watanabe heritable hyperlipidemic (WHHL) rabbits (Buja et al., 1983), both of which develop extensive LDL-induced atherosclerotic lesions. The most potent and specific Zn-SMase inhibitors will be fed to the animals at various doses to first determine toxicity and then effectiveness in inhibiting aortic Zn-SMase activity and atherogenesis. Toxicity could arise from both "non-specific" and specific effects of the compounds. The specific effects would be related to physiologically important functions of Zn-SMase. Regarding this point, it is possible that microglial cell-secreted Zn-SMase (above) plays an important role in scavenging myelin in response to nerve injury. Thus, an inhibitor that does not cross the blood-brain barrier might be most useful for the atherosclerosis studies.

Protocols testing both primary prevention and secondary regression will be established, and the extent and nature of atherosclerosis will be determined by both quantitative (Paigen et al, 1987) and morphological (Nakashima et al., 1994) assays. Careful documentation of plasma lipoprotein levels and properties will also be carried out. Evidence of anti-atherogenic effects would be followed by more detailed mechanistic studies that will specifically assess LDL retention (Kreuzer et al, 1994) and aggregation in vivo.

Creation and Examination of Mice that Selectively Lack Zn-SMase

Another embodiment of the present invention is to determine whether mice that specifically lack Zn-SMase, when bred into an atherogenic background (i.e., apo B transgenic mice) will be protected from atherosclerosis. From the recent discovery, it is now known the currently available acid SMase knockout mice lack two distinct enzymes. Since the absence of lys-SMase might complicate the evaluation of atherogenesis, it will be necessary to create a Zn-SMase "knockout" mouse. The overall strategy will be as follows: (1) based upon specific strategies, create a genetic construct that can encode only lysosomal SMase; (2) create transgenic mice based upon this selective lys-SMase construct. Natural flanking regions will be utilized in the transgene to avoid overexpression of the enzyme; and (3) cross these mice with acid SMase knockout mice to create a mouse that lacks only Zn-SMase.

Once created and verified, the Zn-SMase knockout mice will be crossed with apo B transgenic mice. The Zn-SMase knockout x apo B transgenic mice will be compared with apo B transgenic mice for the development of atherosclerosis exactly as described in Section I above, including the in-vivo retention and aggregation mechanistic studies. The creation of a mouse that selectively overexpresses Zn-SMase, using a genetic construct based on the results of our structural studies is also possible, The construct would be ligated to a macrophage-specific promoter, such as the scavenger receptor promoter (Horvai et al, 1995,, so that the mice would oversecrete the enzyme specifically in macrophages. These mice would develop accelerated atherosclerosis that could be ameliorated by the Zn-SMase inhibitors developed.

Arterial wall factors undoubtedly account for a large portion of atherosclerotic disease in humans and probably explain the large number of patients that develop atherosclerosis despite lipid-lowering therapy. In this light, arterial wall molecules that promote subendothelial lipoprotein retention and aggregation are probably very important. A macrophage-secreted molecule—Zn-SMase—may play a key role in these processes. By using both pharmacological inhibitors and genetic manipulations in animal models of atherosclerosis, it is possible to critically test the role of macrophage-secreted Zn-SMase in lipoprotein retention & aggregation and atherogenesis. The usefulness of the pharmacological inhibitors will be evaluated, leading to the development of important statin-complementary anti-atherogenic therapy in humans.

EXAMPLE 5

Human Vascular Endothelial Cells are a Rich and Regulatable Source of Secretory Sphingomyelinase We recently reported that macrophages and fibroblasts secrete a $Zn^{2+}$-dependent SMase (S-SMase), which, like lysosomal SMase, is a product of the acid SMase gene. S-SMase may cause subendothelial retention and aggregation of lipoproteins during atherogenesis, and the acid SMase gene has been implicated in ceramide-mediated cell signalling, especially involving apoptosis of endothelial cells. Because of the central importance of the endothelium in each of these processes, we now sought to examine the secretion and regulation of S-SMase by vascular endothelial cells. Herein we show that cultured human coronary artery and umbilical vein endothelial cells secrete massive amounts of S-SMase (up to 20-fold more than macrophages). Moreover, whereas S-SMase secreted by macrophages and fibroblasts is almost totally dependent on the addition of exogenous $Zn^{2+}$, endothelial-derived S-SMase was partially active ever in the absence of added $Zn^{2+}$. Secretion of S-SMase by endothelial cells occurred both apically and basolaterally, suggesting an endothelial contribution to both serum and arterial-wall SMase. When endothelial cells were incubated with inflammatory cytokines, such as interleukin-1β and interferon-γ, S-SMase secretion by endothelial cells was increased 2–3-fold above the already high level of basal secretion, whereas lysosomal SMase activity was decreased. The mechanism of interleukin-1β-stimulated secretion appears to be through increased routing of a SMase precursor protein through the secretory pathway. In summary, endothelial cells are a rich and regulatable source of enzymatically active S-SMase, suggesting physiologic and pathophysiologic roles for this enzyme.

The enzyme sphingomyelinase (SMase) (sphingomyelin phosphodiesterase; EC 3.1.4.12) catalyzes the hydrolysis of sphingomyelin to ceramide and choline-phosphate (1). SMase reactions have been implicated in specific atherogenic processes (2–5) and in cell-signalling events (6–8). For example, partial hydrolysis of lipoprotein-sphingomyelin by bacterial SMase, via the generation of lipoprotein-ceramide, leads to lipoprotein aggregation (2) and retention onto arterial-derived matrix (3). Aggregation and retention of lipoproteins in the arterial wall are prominent events during atherogenesis (9–11), and these lipoprotein aggregates are among the most potent inducers of macrophage cholesteryl ester accumulation ("foam cell" formation) (2,3,12–14). Most importantly, recent findings indicate that subendothelial LDL, including aggregated LDL isolated from human lesions, is hydrolyzed by an arterial-wall SMase (4). Regarding cell signalling, treatment of certain cell types with bacterial SMase results in cellular differentiation, cellular senescence, or apoptosis, which are thought to be triggered by ceramide-mediated signal transduction pathways (6–8). Moreover, cell-derived SMase activity and then cellular ceramide content rise when these cell types are treated with specific inflammatory cytokines, such as tumor necrosis factor-α, interleukin-1β, and interferon-γ (6–8).

Experimental evidence suggests that products of the acid SMase (ASM) gene may have a prominent role in both atherogenesis and ceramide-mediated apoptosis. Hydrolysis of lipoprotein-SM retained on subendothelial matrix would clearly be expected to be an extracellular event. In this context, our laboratory has reported that the ASM gene in macrophages and fibroblasts gives rise not only to lysosomal SMase (L-SMase) but also, via differential trafficking of the ASM precursor protein, to a secretory SMase (S-SMase) (15). Importantly, S-SMase secreted by these cells, which is activated by physiological levels of $Zn^{2+}$ (15), can hydrolyze and cause the aggregation of atherogenic lipoproteins, even at neutral pH (16). Several cell-culture studies have also implicated a role for acid SMase activity in cytokine-induced, ceramide-mediated apoptosis (17–19), and mice in which the acid SMase (ASM) gene has been disabled by homologous recombination show defective radiation- and endotoxin-induced apoptosis in vivo (20,21). The products of the ASM gene that mediate these cell-signalling events have not been identified, but S-SMase might be an excellent candidate since the outer leaflet of the plasma membrane is rich in SM (22).

The endothelium is central to these processes. Our previous work on S-SMase focused on macrophages (15), which enter the arterial wall in response to the initial retention of lipoproteins in the subendothelial matrix (5,23) and therefore may contribute to lipoprotein aggregation after lesion initiation. Lipoprotein aggregation also occurs, however, in pre-lesional susceptible segments of the subendothelium (10), and thus the endothelium would be a likely candidate for a source of S-SMase in the pre-lesional arterial wall. Likewise. recent in-vivo studies have shown that the endothelium is the key tissue in cytokine-induced, SM-mediated apoptosis (20,21). Moreover, cytokines are important regulators of endothelial function (24,25), atherogenesis, and apoptosis (26,27), which raises the possibility that cytokines influence endothelial secretion of S-SMase.

In this report, we demonstrate that cultured endothelial cells, including human coronary artery endothelial cells, are an even more abundant source of S-SMase than are macrophages. Furthermore, we show that the secretion of S-SMase by endothelial cells is strongly regulated by cytokines known to be present in atherosclerotic and inflammatory lesions. The mechanism of this regulation is primarily through an alteration in the cellular trafficking of the ASM precursor protein. Thus, the vascular endothelium is likely to be a major, regulatable source of S-SMase that may contribute to atherogenesis and inflammation.

Experimental Procedures

Materials—The Falcon tissue culture plasticware used in these studies was purchased from Fisher Scientific Co. (Springfield, N.J.). Millicell-CM 0.4-μm culture plate inserts were from Millipore. Tissue culture media and other tissue culture reagents were obtained from GIBCO BRL. Fetal bovine serum (FBS) was obtained from Hyclone Laboratories (Logan, Utah) and was heat-inactivated for 1 h at 65° C. (HI-FBS). Human recombinant cytokines were obtained as follows: interferon-β and interferon-γ from Biogen (Cambridge, Mass.), interleukin-4 from Peprotech (Rocky Hill, N.J.), and interleukin-1β from R & D Systems Inc (Minneapolis, Minn.). [9,10-$^3$H]Palmitic acid (56 Ci/mmol) was purchased from DuPont NEN and [N-palmitoyl-9-10-$^3$H]Sphingomyelin was synthesized as previously described (15,28,29). (N,N)-Dimethylformamide; 1,3-dicyclohexylcarbodiimide; (N)-hydroxysuccinimide; and (N,N)-diisopropylethylamine were purchased from Aldrich Chemical Inc. Precast 4–20% gradient polyacrylamide gels were purchased from NOVEX (San Diego, Calif.). Nitrocellulose was from Schleicher and Schuell (Keene, N.H.). FLAG-tagged S-SMase and rabbit anti-S-SMase were kindly provided by Dr. Henry Lichtenstein (Amgen, Boulder, Colo.); the FLAG-tagged S-SMase was purified by anti-FLAG immunoaffinity chromatography from the conditioned medium of cells transfected with a human ASM-FLAG cDNA.[2] For the immunoprecipitation protocol (below), this antibody was further purified on an S-SMase-Affigel affinity column (Amgen, Boulder, Colo.). A murine monoclonal antibody against the FLAG epitope was purchased from KODAK®, and peroxidase-conjugated sheep anti-mouse IgG was from Amersham. Peroxidase-conjugated goat anti-rabbit IgG and concanavalin A-Sepharose was purchased from Pierce Chemical Co. (Rockford, Ill.). DEAE-Sephacel was from PHARMACIA®. Bovine liver 215-kD mannose-6-phosphate receptor linked to Affigel 15 was made as described by Varki and Kornfeld (30). All other chemicals and reagents were from Sigma Chemical Co. (St. Louis, Mo.), and all organic solvents were from Fisher Scientific Co.

Cells—Primary cultures of HUVEC were obtained from fresh umbilical cords and maintained in cell culture as previously described (31). Human coronary artery endothelial cells from a 38-year-old female donor were purchased from Clonetics Corp. (San Diego, Calif.; cat. # CC-2585, Strain #3033). The cells were grown in endothelial basal media (EBM) (Clonetics) supplemented with 10% HI-FES; 10 µg endothelial cell growth supplement/ml (Sigma; cat. # E0760) and 50 µg gentamicin/ml. Primary cultures of bovine aortic endothelial, cells were established and subcultured as described previously (32). For the experiment in FIG. 2, the cells were plated on Millicell-CM 0.4-µm culture plate inserts placed in 35-mm wells in (-MEM containing 10% FES; the inserts had been previously coated with 0.1% gelatin for 1 h and then with 5 µg collagen/ml and 20 µg fibronectin/ml for 1h. Monolayer cultures of J774.A1 cells (from the American Type Culture Collection—see Ref. (33)) were grown and maintained in spinner culture with DMEM/HI-FBS/PSG as described previously (33,34). Human peripheral blood monocytes were isolated from normal subjects as previously described (35) and induced to differentiate into macrophages by the addition of 1 ng GM-CSF/ml of media on days 1, 4, and 11 of culture as described previously (35); by day 14, the cells were differentiated as assessed by morphological changes (e.g., increased spreading) and increased expression of scavenger receptor activity (of. Ref. (36)) Unless indicated otherwise, the cells were plated in 35-mm (6-well) dishes in media containing HI-FES for 48 h. The cells were then washed 3 times with PBS and incubated for 24 h in 1 ml fresh serum-free media containing 0.2%6 BSA. This 24-h conditioned medium was collected for SMase assays.

Harvesting of Cells and Conditioned Media—Following the incubations described above and in the figure legends, cells were placed on ice and the serum-free conditioned media was removed. The cells were washed two times with ice-cold 0.25 M sucrose and scraped into 0.3 ml and 3.0 ml of this sucrose solution per 35-mm and 100-mm dishes, respectively. Unless indicated otherwise, the scraped cells were disrupted by sonication on ice using three 5-second bursts (Branson 450 Sonifier), and the cellular homogenates were assayed for total protein by the method of Lowry et al. (22) and for SMase activity as described below. The conditioned media were spun at 800×g for 5 min to pellet any contaminating cells and concentrated six-fold using a Centriprep 30 (Amicon; Beverly, Mass.) concentrator (molecular weight cut off=30,000).

Smase Assay—As previously described (15), the standard 200-µl assay mixture consisted of up to 40 µl of sample (conditioned media or homogenized cells; see above, and a volume of assay buffer (0.1 M sodium acetate, pH 5.0) to bring the volume to 160 µl. The reaction was initiated by the addition of 40 µl substrate (50 pmol [$^3$H]sphingomyelin) in 0.25 M sucrose containing 3% Triton X-100 (final concentration of Triton X-100 in the 200-µl assay mix=0.6%). When added, the final concentrations of EDTA and $Zn^{2+}$ were 5 mM and 0.1 mM, respectively, unless indicated otherwise. The assay mixtures were incubated at 37° C. for no longer than 3 h and then extracted by the method of Bligh and Dyer (37); the lower, organic phase was harvested, evaporated under $N_2$, and fractionated by TLC using chloroform:methanol (95:5). The ceramide spots were scraped and directly counted to quantify [$^3$H]ceramide. Typically, our assay reactions contained approximately 20 µg of cellular homogenate protein and a volume of conditioned media derived from a quantity of cells equivalent to approximately 50 µg of cellular protein.

SMase Immunohistochemistry of Murine Aorta—Hearts from chow-fed, 4-week old female ASM knockout mice and wild-type mice of the same genetic background (SV129/C57BL6) were perfused, embedded in O.C.T. compound, and snap-frozen as previously described (38). 8-µm-thick sections of the proximal aorta were cut on a cryostat and fixed in 10% buffered formalin for 5 min at room temperature. The sections were blocked in 2% murine serum in PBS for 2 h at room temperature and then incubated with 20 µg anti-SMase antibody per ml PBS containing 0.1% Triton X-100 for 2–4 h at room temperature. Bound antibody was detected with a biotinylated secondary antibody followed by streptavidin peroxidase (Vectastain Elite ABC-peroxidase kit; Vector Laboratories Inc., Burlingame, Calif.) and 3,3'-diaminobenzidine. The specimens were counterstained with hematoxylin and then viewed with an Olympus IX 70 inverted microscope using a X100 objective.

Partial Purification of L- and S-SMase from HUVECs—A modification of previously published procedures (39) was used. Cells were scraped in ice-cold 40 mM Tris-HCl, 0.1 mM $ZnCl_2$, 0.1% NP-40, pH 7.2 (Buffer A), disrupted by sonication on ice using three 5-second bursts (Branson 450 Sonifier) and centrifuged at 100,000×g for one hour. The supernate (<5 ml) was applied to a 5-ml column of DEAE-Sephacel, and the column was capped and incubated end-over-end for 90 min at room temperature. The column was then uncapped, and the flow-through fraction was collected; the column was washed with another 1–2 ml of Buffer A, and this flow-through fraction was added to the first. The combined flow-through fractions were loaded onto another DEAE-Sephacel column, and the procedure was repeated. The flow-through fractions from this second column were pooled, concentrated using a Centriprep 30 (see above), assayed for protein concentration by the method of Lowry (40), and subjected to SDS-PAGGE and immunoblotting.

The conditioned medium was concentrated, dialyzed against Buffer A, and subjected to the same two rounds of DEAE-Sephacel chromatography as above. The combined flow-through fractions from the second DEAE-Sephacel step were then concentrated and dialyzed against 10 mM Tris-HCl, 500 mM NaCl, 1 mM $MgCl_2$, 1 mM $MnCl_2$, 1 mM $CaCl_2$, 0.1% NP-40, and 0.02% $NaN_3$, pH 7.2 (Buffer B). This solution (<1 ml) was added to a one-ml concanavalin A-Sepharose column and incubated with the column exactly as described for the DEAE-Sephacel step. The column was then washed with two bed volumes of Buffer B containing 10 mM methyl-glucopyranoside. followed by two bed volumes of Buffer B containing 1 M methyl-glucopyranoside. This last eluate was concentrated, assayed for protein concentration by the method of Lowry (40), and subjected to SDS-PAGGE and immunoblotting.

Northern Blot of SMase mRNA—Total cellular RNA was isolated from HUVECs using RNAzol B (Tel-Test. Inc., Friendswood, Tex.). Approximately 10 µg of RNA was separated on a 1% agarose gel and blotted onto a nylon membrane. The membrane was hybridized in a QuikHyb hybridization solution (Stratagene) with a 1.6-kB EcoRI-XhoI fragment of human ASM cDNA (41) that was labeled with $^{32}$P by the random-priming Procedure (GIBCO-BRL®). The amount of RNA loaded for each condition was normalized using a probe to glyceraldehyde-3-phosphate dehydrogenase. The relative intensities of the mRNA bands were determined by densitometric scanning of the autoradiograms using a Molecular Dynamics Computing Densitometer (model 300A) with Image-Quant software.

LDH Assay—LDH activity was assayed in medium and cells as reported previously (42) using a kit purchased from Sigma (catalogue #500); the assay measures the unreacted pyruvic acid using a colorometric assay.

SDS-Polyacrylamide Gradient Gel Electrophoresis (SDS-PAGGE) and Immunoblotting—Protein samples were boiled in buffer containing 1% SDS and 10 mM dithiothreitol for 10 min, loaded onto 4–20% gradient polyacrylamide gels, and electrophoresed for 50 min at 35 milliamps in buffer containing 0.1% SDS. Following electrophoresis, the proteins on the gels were electrotransferred (100V for 1.5 h) to nitrocellulose for immunoblotting. Next, the nitrocellulose membranes were incubated with 5% Carnation nonfat dry milk in Buffer C (24 mM Tris, pH 7.4, containing 0.5 M NaCl) for 3 h at room temperature. The membranes were then incubated with mouse anti-FLAG monoclonal antibody (1:1000) or rabbit anti-L-SMase antibody (1:1000) in Buffer D (Buffer C containing 0.1% Tween-20, 3% nonfat dry milk, and 0.1% bovine serum albumin) for 1 h at room temperature. After washing four times with Buffer C containing 0.1% Tween-20, the blots were incubated with horseradish peroxidase-conjugated sheep anti-mouse IgG (1:20,000) or goat anti-rabbit IgG (1:20,000) for 1 h in Buffer D at room temperature. The membranes were subsequently washed twice with 0.3% Tween-20 in Buffer C and twice with 0.1% Tween-20 in Buffer C. Finally, the blots were soaked in the enhanced chemiluminescence reagent (Pierce Super Signal, kit) for 2 min and exposed to X-ray film for 1 min.

Immunoprecipitation of S-SMase—20 $\mu$l of HUVEC conditioned medium, 20 $\mu$l of affinity-purified anti-SMase antibody, and 160 $\mu$l of PBS were incubated for 1 h at 4° C. 100 $\mu$l of Protein A-Sepharose (50 mg/ml in 50 mM Tris buffer, pH 7.0) was then added to the incubation mixture, and the slurry was mixed end-over-end for 18 h at 4° C. The suspension was centrifuged for 1 min in a microcentrifuge. The supernate was harvested and assayed for SMase activity.

Statistics—Unless otherwise indicated, results are given as means±S.D. (n=3); absent error bars in the figures signify S.D. values smaller than the graphic symbols.

Results

Figure 1A:
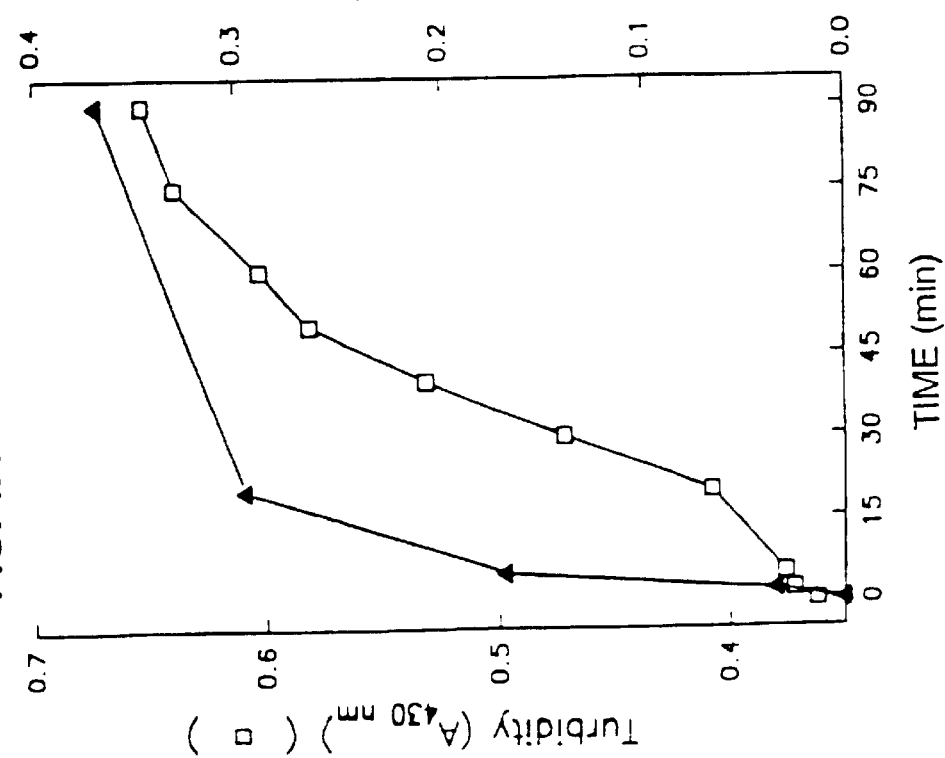

Cultured human vascular endothelial cells secrete abundant amounts of S-SMase—Previous work from our laboratories revealed that human and murine macrophages were a relatively abundant source of S-SMase compared with other cell types such as COS-7 and murine migroglial cells (15). As shown in FIG. 1A, however, both human coronary and umbilical vein endothelial cells (HUVECs) are a much more abundant source of S-SMase; for example, HUVECs secrete almost 20-fold more S-SMase than human macrophages. Interestingly, endothelial-derived S-SMase was partially active in the absence of exogenously added $Zn^{2+}$ (FIGS. 20A–B), whereas S-SMase secreted by macrophages and other cell types previously examined by us was almost entirely $Zn^{2+}$ dependent (15). This observation may be important in the regulation of endothelial-derived S-SMase activity (see Discussion) The data in FIG. 20B show that SMase activity in the cell homogenate, which is not stimulated by exogenous $Zn^{2+}$ and represents L-SMase activity (15), is also very abundant in endothelial cells (recall that S-SMase and L-SMase originate from the same gene (15), mRNA (15), and protein precursor). In summary, the data in FIGS. 20A–B demonstrate that human endothelial cells, including those derived from coronary arteries, are an abundant source of S-SMase, much of which is active in the absence of exogenously added $Zn^{2+}$.

Figure 21A:
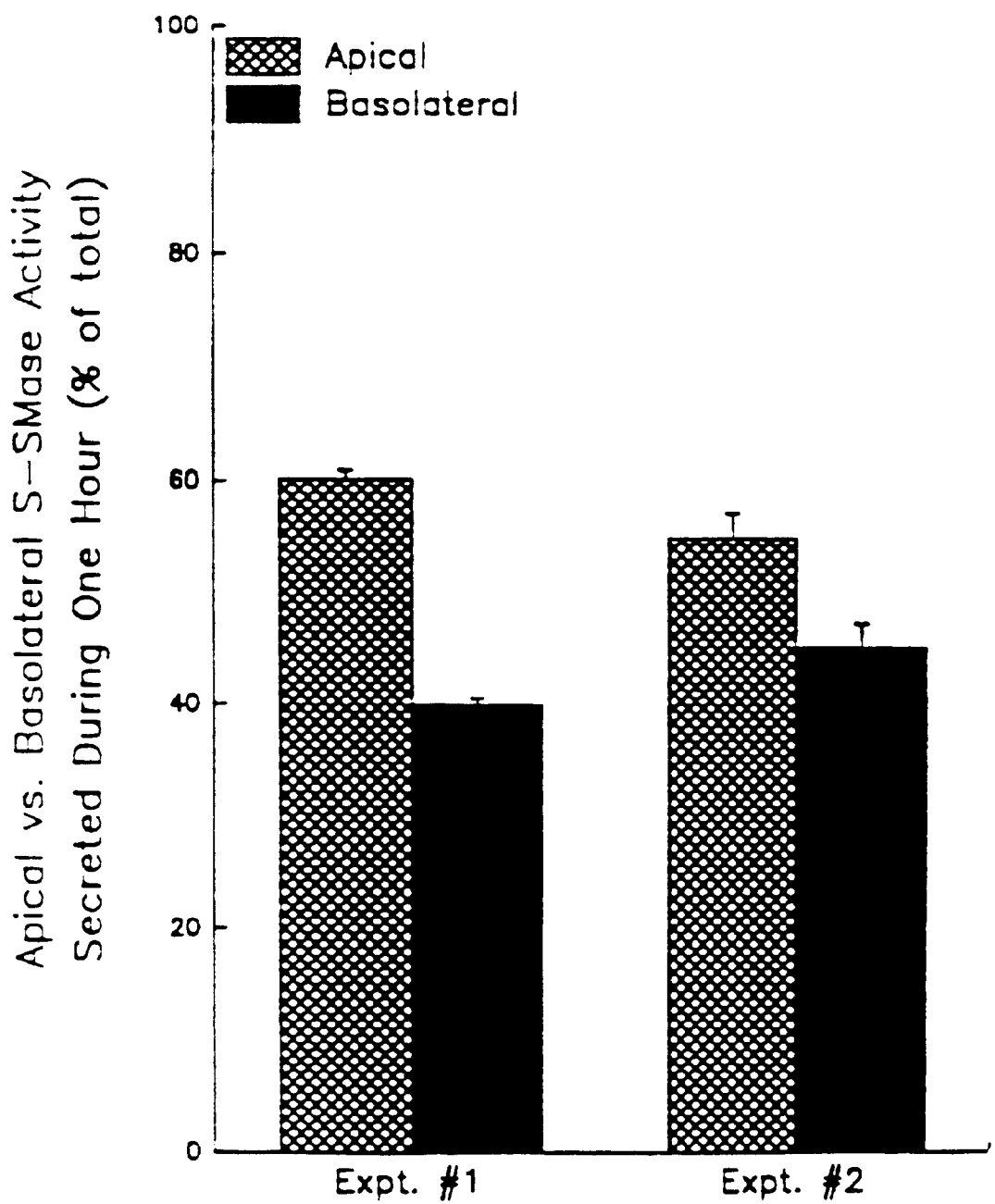
FIGS. 21A–B. Cultured bovine aortic endothelial cells secrete S-SMase from both the apical and basolateral surfaces. Bovine aortic endothelial cells were cultured on Millicell-CM inserts in 35-mm dishes. When the monolayer was confluent, the cells were washed with (MEM containing 0.2% BSA, incubated in this medium for 6 h (to remove any residual serum—see Ref. (15)), washed with PBS, and then incubated with (MEM/BSA again for 1 h. At the end of this 1-h incubation, medium above the cells (apical; cross-hatched bars) and medium under the insert (basolateral; solid bars) were assayed for SMase activity in the presence of 0.1 mM $ZnCl_2$. The results of two separate experiments are shown.
Figure 21B:

We next addressed the polarity of secretion of S-SMase from cultured endothelial cells. Cultures of endothelial cells were established in Trans-well dishes so that S-SMase from the upper (apical) and lower (basolateral) chambers could be assayed separately. As a control for apically secreted enzyme that either "leaked" or was transcytosed into the lower chamber, we set up parallel dishes in which immunoaffinity-purified FLAG-tagged S-SMase was added to the upper chamber and then monitored using an anti-FLAG immunoblot assay. As shown in FIGS. 21A–B, substantial amounts of S-SMase activity were found in both the upper and lower chambers of the Trans-well dishes. In contrast, FLAG-tagged S-SMase added to the upper chamber did not appear in the lower chamber during this one-hour experiment (FIG. 21B). From these data we conclude that cultured endothelial cells secrete S-SMase both apically, and basolaterally. If the endothelium acts similarly in vivo, these findings implicate the endothelium as a possible source of both subendothelial and serum S-SMase (cf. Ref (43)).

Figure 22A:
FIGS. 22A–B. SMase immunohistochemistry of proximal aorta from wild-type and SMase knockout mice. 8-μm sections of proximal aorta from an ASM (SMase) knockout mouse (FIG. 22A) and from a wild-type mouse of the same genetic background (FIG. 22B) were stained with an anti-SMase antibody, counterstained with hematoxylin, and viewed by microscopy as described under "Experimental Procedures." The open arrows show areas of intracellular staining and the closed areas show staining that appears to be on the lumenal surface of the endothelial cells.
Figure 22B:
Figure 23B:
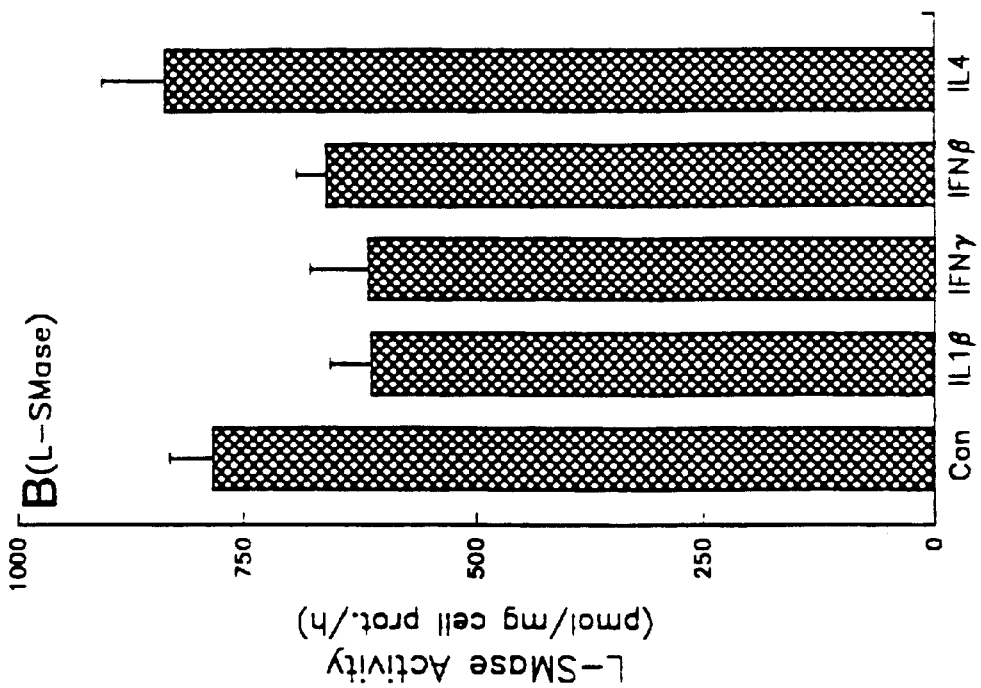
FIGS. 23A–B. Cytokine regulation of S- and L-SMase of HUVECs. HUVECs were incubated for 18 h in DMEM, 0.2% BSA alone or containing human recombinant interleukin-1β (5 ng/ml) interferon-γ (1000 units/ml) interferon-β (1000 units/ml), and interleukin-4 (10 ng/ml) for 18 h. Conditioned media (FIG. 23A) and cell homogenates (FIG. 23B) from these cells were then assayed for SMase activity in the presence or absence of 0.1 mM $ZnCl_2$, respectively.
Figure 23A:
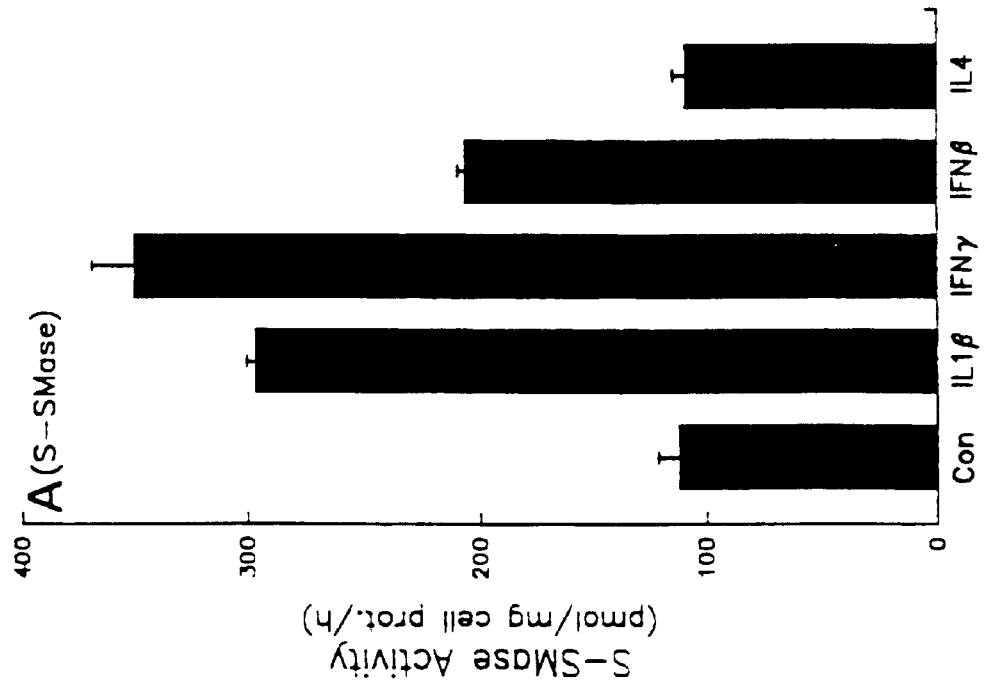

Smase is present in the endothelium of murine aorta—To complement the cell culture studies described above. we used immunohistochemistry to detect SMase in slices of murine proximal aorta. Because L- and S-SMase are derived from the same protein precursor and differ only by post-translational modifications (15), the anti-SMase antibodies currently available to us recognize both forms of the enzyme. To ensure the specificity of the signal for SMase, proximal aorta From ASM knockout mice (44), which lack both L- and S-SMase (15), were used as a negative control (FIG. 22A). FIGS. 23A–B demonstrate substantial SMase staining in the endothelium; much of the stain in this image appears to be intracellular (open arrow), which is most likely L-SMase and possibly some S-SMase in the secretory pathway. By comparison, medial staining was much weaker, though still specific. These data demonstrate that the high levels of intracellular SMase in cultured endothelial cells (FIG. 20B) reflect the situation in an actual vessel wall. In addition, we also noticed areas of dark staining on the lumenal edge of some of the endothelial cells (closed arrow). This staining is specific and does not appear lysosomal, and so it is possible that this signal represents S-SMase that has been secreted and perhaps retained on the cell surface.

Secretion of S-SMase from human endothelial cells is regulated by cytokines—Inflammatory cytokines are important constituents of atherosclerotic lesions and may contribute go various aspects of atherogenesis (26). A manor target of these cytokines is the endothelium (24,25). To determine if cytokines known to be present in atherosclerotic lesions affect endothelial-derived S-SMase, cultured human endothelial cells were exposed to IL-1$\beta$, interferon-$\gamma$, interferon-$\beta$, and IL-4. Each of the first three cytokines substantially increased the accumulation of S-SMase in the conditioned media of these cells, although IL-4 had no effect (FIGS. 23A & B). In particular; IL-1$\beta$ and interferon-$\gamma$ increased S-SMase activity ~3-fold. Interestingly, the stimulatory cytokines led to a decrease in L-SMase activity (FIG. 23B). This pattern is distinct from that observed during monocyte-to-macrophage differentiation, in which both S- and L-SMase activities are increased (15).

Figure 24:
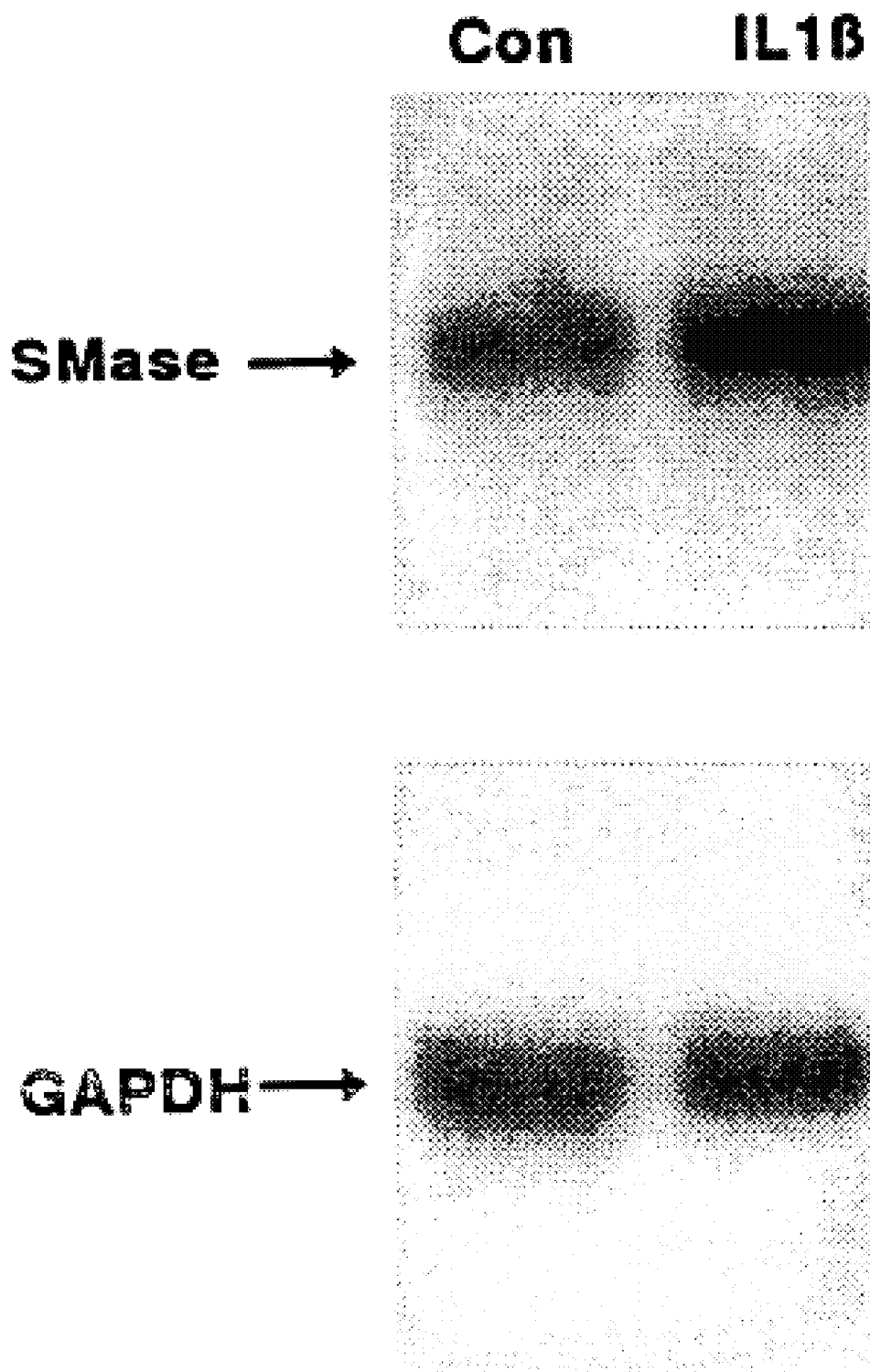
FIG. 24. Northern blot analysis of HUVECs incubated in the absence or presence of IL-1β. HUVECs were incubated for 18 h in DMEM, 0.2% BSA alone (Con) or containing human recombinant interleukin-1β (5 ng/ml) (IL1β). Total RNA was extracted from the cells, electrophoresed, blotted, and probed for ASM (SMase) and GAPDH mRNA as described under "Experimental Procedures." Quantification by phosphoimaging or densitometry indicated ~40% increase in the ratio of ASM:GAPDH mRNA signals with IL-1β treatment.

IL-1$\beta$ increases S-SMase secretion by HUVECs via alteration in the trafficking of the ASM precursor protein—We next sought to determine the mechanism of cytokine-mediated induction of S-SMase secretion by HUVECs. For these studies, we focused on IL-1β, and we first determined whether this cytokine increased SMase mRNA levels in HUVECs. As shown in FIG. 24, there was ~40% increase in SMase mRNA in IL-1β-treated HUVECs, when normalized for GAPDH mRNA and quantified by either densitometry or by using a phosphoimager. Because differences less than 2-fold in Northern blot assays may not be significant and because the IL-1(-induced increase in S-SMase activity was greater than 3-times control, we conclude that most, if not all, of the induction by this cytokine was post-transcriptional. This conclusion is consistent with the finding that the cytokine-mediated increase in S-SMase is accompanied by a decrease in L-SMase (above).

Figure 25A:
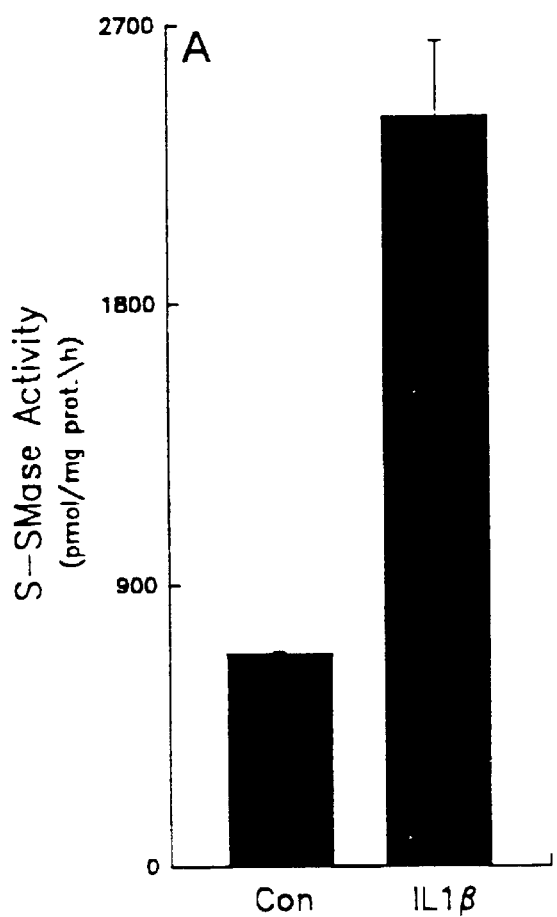
FIGS. 25A–B. Effect of IL-1β on the release of LDH from HUVECs. HUVECs were incubated for 18 h in DMEM, 0.2% BSA alone (Con) or containing human recombinant interleukin-1β (5 ng/ml) (IL1β). Conditioned media from these cells were then assayed for SMase activity (FIG. 25A) and LDH activity (FIG. 25B).
Figure 25B:
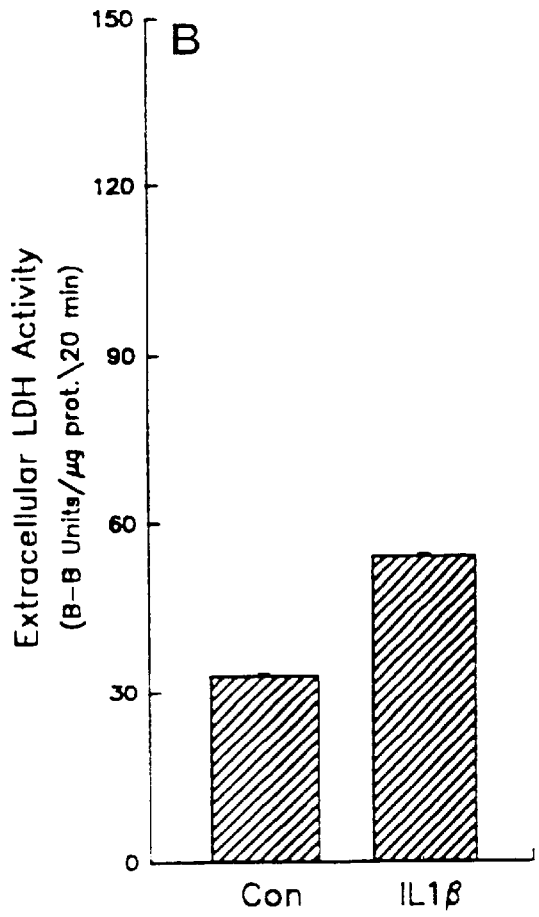

Next, we asked whether the mechanism of IL-1β-induced S-SMase secretion could be the result of cellular lysis. For example, cellular release of certain molecules involved in inflammation may occur physiologically by this mechanism (45). To test this idea, the release of the cytosolic protein LDH was assayed. Under conditions in which S-SMase was induced by IL-1β to 3.6-times control (FIGS. 25A&B). LDH release increased only 60% (FIG. 25B) Thus at most, cellular lysis can account for only a small proportion (i.e., ~20%) of the IL-1β-induced increase in S-SMase.

We recently reported that S-SMase is secreted through a Golgi pathway that bypasses the lysosomal pathway of L-SMase. Thus, we considered three general mechanisms to explain how IL-Lβ increases the secretion of SMase: secretion of mannose-phosphorylated SMase during trafficking of the ASM precursor to lysosomes (e.g., due to saturation of the mannose-6-phosphate receptor—cf. Ref. (46)), induction of secretion of intralysosomal SMase (cf. Ref. (47)), or increased trafficking of the ASM precursor protein through the normal Golgi secretory pathway. To begin, we assessed the mannose-phosphorylation state of S-SMase from control and IL-1β-treated HUVECs by passing conditioned media from these cells over a mannose-phosphate receptor column (cf. Ref. (48)). By Western blot analysis quantified by densitometry, only 7.9% of control S-SMase and 4.9% of S-SMase from the cytokine-treated cells bound to the column and could be eluted with mannose-6-phosphate. As a control for this experiment, we have previously shown that the massive secretion of SMase by ASM-transfected CHO cells can be partly explained by secretion of mannose-phosphorylated SMase due to saturation of the mannose-6-phosphate receptor[2]; when conditioned medium from these cells was passed over the receptor column, 40.3% bound and could be eluted with mannose-6-phosphate. Based on this set of experiments, we conclude that IL-1β-mediated induction of SMase secretion by HUVECs is not due to increased secretion of mannose-phosphorylated SMase during trafficking of the ASM precursor to lysosomes.

Next, we compared the zinc-dependency of S-SMase and L-SMase activities from control and IL-1(-treated HUVECs. $Zn^{2+}$ increased the enzymatic activity of S-SMase 1.77±0.03-fold and 1.78±0.17-fold from IL-1β-treated and untreated cells respectively, whereas $Zn^{2+}$ increased the enzymatic activity of L-SMase 1.13±0.08- and 1.09±0.04-fold from IL-1β-treated and untreated cells, respectively. Thus. S-SMase from IL-1β-treated HUVECs had a zinc-dependency similar to that of S-SMase from untreated cells, not to that so L-SMase. These data support the idea that IL-1β treatment results in increased trafficking of the ASM precursor protein through the normal Golgi secretory pathway, not in increased secretion of L-SMase.

Figure 26:
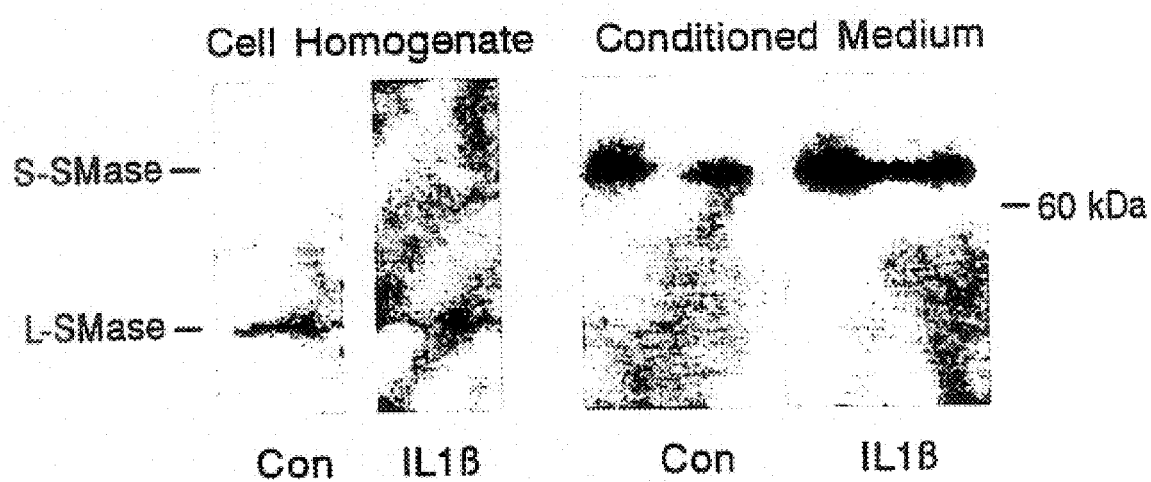
FIG. 26. Immunoblot analysis of L- and S-SMase from control and IL-1β-treated HUVECs. HUVECs were incubated for 18 h in DMEM, 0.2% BSA alone (Con) or containing human recombinant interleukin-1β (5 ng/ml) (IL1β). SMase was partially purified from the cell homogenates and conditioned media of these cells, and then aliquots derived from equivalent numbers of cells were subjected to immunoblot analysis. Specifically, conditioned medium from control and IL-1(-treated cells yielded 256.0 and 262.5 μg of concanavalin A eluate protein, of which 60.8 μg and 60.0 μg aliquots were loaded onto the SDS-PAGGE gel, respectively. Cell homogenates from control and IL-1β-treated cells yielded 168.1 and 160.6 μg of DEAE flow-through protein, of which 59.5 μg and 60.0 μg aliquots were loaded onto the SDS-PAGGE gel, respectively. No band at the molecular weight of L-SMase was visible in conditioned media (right-hand panels), even when overexposed.

To further test this conclusion, we took advantage of our previous observation that L-SMase has a lower apparent $M_r$ than S-SMase on SDS-PAGGE, presumably because of different post-translational modifications. Thus, we sought to determine if conditioned medium from IL-1-treated HUVECs had increased amounts of higher-$M_r$ SMase, indicating increased flux through the normal secretory pathway, or normal levels of the higher-$M_r$ form plus the appearance of the lower-$M_r$ form, indicating secretion or release of L-SMase from lysosomes (FIGS. 26A&B). It should be noted that the HUVEC enzyme, particularly HUVEC L-SMase, is not well recognized by our antibody, and so the immunoblot signal, particularly for the intracellular enzyme (L-SMase), is weak. Nonetheless, the data in FIGS. 26A–B confirm the differences in $M_r$ between L- and S-SMase in this cell type (compare lanes 1 and 3) and show that only the higher-$M_r$ S-SMase was detectably increased in the IL-15-treated cells (compare lanes 3 and 4). By densitometry, this increase was approximately two-fold. Even when the immunoblot was overexposed, the conditioned medium from the IL-1β-treated cells contained no evidence of a band at the $M_r$ of L-SMase. These data further support the conclusion that the increase in S-SMase from HUVECs induced by IL-1β is primarily due to an increase flux of the common SMase precursor through the Golgi-secretory pathway.

Discussion

The data in this report demonstrate that endothelial cells are a rich source of active S-SMase, particularly in the presence of inflammatory cytokines. The potential physiologic relevance of these findings is related t. the postulated role of the endothelium in extracellular SMase-induced lipoprotein aggregation and retention and to the demonstrated role of this tissue in cytokine-induced, acid SMase-mediated cell signalling (see Introduction and below). In addition, our results reveal several novel mechanisms for the regulation of S-SMase, particularly by alterations in intracellular protein trafficking.

We have previously shown that retained and aggregated lipoproteins in atherosclerotic lesions are hydrolyzed by an extracellular arterial-wall SMase (4), and we found that S-SMase was the only SMase secreted by arterial-wall cells (15). Mohan Das et al. (49) have reported that a magnesium-dependent SMase is externally oriented on neurons. We have not yet investigated whether this enzyme, which has not yet been cloned, is present on the surface of arterial-wall cells. Nonetheless, we imagine that a secreted enzyme would have more access to lipoproteins retained on subendothelial matrix than a cell surface-bound enzyme. These points, together with the findings reported herein, lead us to propose the following model: basal levels of endothelial-derived S-SMase help initiate the atherosclerotic lesion by promoting lipoprotein retention and aggregation (5). Then, as T-cells and macrophages enter lesions (23,26) and secrete cytokines and (at least in the case of macrophages) additional S-SMase, lipoprotein-SM hydrolysis and lipoprotein retention and aggregation would be amplified.

We have also speculated endothelial-derived S-SMase may play a role in ceramide-mediated apoptosis. This speculation is based upon several pieces of information. First a product of the acid SMase gene plays an important role in endothelial apoptosis in vivo (20,21). Specifically, the pulmonary endothelium of ASM knockout mice was the manor tissue demonstrating a defect in ceramide generation and apoptosis in response to total body irradiation; radiation-induced apoptosis in thymocytes and splenocytes was much less diminished in the ASM knockout vs. wild-type mice (20). Moreover, very recent studies in mice have shown that the endothelium is the target of TNF(-mediated apoptosis after injection of lipopolysaccharide. This response is associated with an increase in endothelial ceramide content and is greatly diminished in ASM knockout mice, indicating involvement of a SMase arising from the ASM gene (21). Second, the data in this report show that endothelial cells are rich and cytokine-regulatable source of S-SMase, a product of the ASM gene. Third, S-SMase may nave more access to the most abundant pools of cellular SM (22). In contrast, since lysosomal membranes have little SM (50), signalling by L-SMase would have to occur during trafficking of the nascent enzyme to lysosomes or would require delivery of SM into lysosomes. Thus, we propose that apoptotic stimuli, such as radiation and cytokines, increase the amount of endothelial-derived S-SMase from a sub-threshold basal level to a level capable of generating enough cellular ceramide to trigger or enhance cell-signalling events. It is important to note, however, that this hypothesis is based upon several controversial assumptions. For example, despite the compelling data obtained using ASM knockout mice (20,21), there are some cell-culture systems that have shown a role for the neutral, magnesium-dependent SMase in ceramide-mediated apoptosis (6). In addition, there are conflicting data regarding the role of cell-surface vs. intracellular cools of SM in ceramide-mediated signalling (cf. Ref. (51) and Discussion therein). Nonetheless, the data presented in this report give impetus for further in-vitro and in-vivo studies on the role of endothelial-derived S-SMase in atherogenesis and ceramide-mediated apoptosis.

Regarding regulation of S-SMase, the data in this example provide evidence to support at least three separate mechanisms for control of S-SMase. Two of these mechanisms, alterations On protein trafficking and accessibility to cellular zinc, are based upon the following model of now the ASM gene gives rise to both L- and S-SMase$^2$: when a common precursor protein derived from the ASM gene is mannose-phosphorylated and thus is targeted to lysosomes. it becomes L-SMase. During this targeting, the enzyme acquires cellular $Zn^{2+}$ and so does not require exogenous $^{2+}Zn$ for enzymatic activity. In contrast, when the common precursor is not mannose-phosphorylated, and thus is targeted to the Golgi-secretory pathway, it gives rise to S-SMase. In the secretory pathway, the enzyme does not acquire cellular $Zn^{2+}$, and so S-SMase secreted by macrophages requires exogenous $Zn^{2+}$ for enzymatic activity.

Based on this model, we predicted that one level of control of S-SMase secretion might be the proportion of the common ASM precursor trafficked into the lysosomal vs. secretory pathways. The current data indicate that this mechanism is indeed primarily responsible for the increase in S-SMase in response to IL-1β. How might a cytokine influence protein trafficking? The key regulatory step in the trafficking of the SMase precursor is mannose phosphorylation of the precursor by N-acetylglucosaminyl-1-phosphotransferase (52,53), and we speculate that cytokines may affect (e.g., by protein phosphorylation) either the activity of this phosphotransferase or the suitability of the SMase precursor as its substrate. Further work will be needed to test this and other possible mechanisms.

A second level of regulation of S-SMase is via $Zn^{2+}$-induced activation (15). The zinc requirement of S-SMase is similar to that of matrix metalloproteinases (15,43,54,55), and so under conditions in which these proteinases are active, such as in atherosclerotic lesions (56), one would expect S-SMase to be active as well. In addition, $Zn^{2+}$ levels have been reported to be elevated in atherosclerotic (57) and inflammatory (58) lesions. Nonetheless, accessibility of extracellular zinc, perhaps modulated by zinc-binding proteins such as metallothionein (59), may represent a regulatory mechanism. Our current results indicate that accessibility of cell-derived zinc is also relevant: S-SMase from endothelial cells was partially activated in the absence of exogenously added $Zn^{2+}$ (FIGS. 20A–B). In contrast, S-SMase from macrophages, fibroblasts and CHO cells is almost entirely inactive in the absence 0o added $Zn^{2+}$ (FIGS. 20A–B and Ref. (15)). Based upon our model (above), we propose that SMase in the secretory pathway of endothelial cells, unlike SMase in the secretory pathway of the other cells examined, has partial access to cellular pools of $Zn^{2+}$. The findings that endothelial cells secrete abundant amounts of S-SMase and that this S-SMase is partially active in the absence of added $Zn^{2+}$ suggest that endothelial-derived S-SMase has unique physiologic roles.

A third point of S-SMase regulation is extracellular pH. S-SMase, like L-SMase, has an acidic pH optimum when assayed in vitro using sphingomyelin in detergent micelles as substrate (15). Thus, S-SMase may be particularly active in environments in which the pH is relatively low, such as in advanced atherosclerotic lesions (60–63), in certain types of inflammatory processes (62,64), and possibly after re-uptake into acidic endosomes. Calahan noted, however, that pH affects only the $K_m$, not the $V_{max}$, of L-SMase (65). This finding suggests that access to SM is the issue, and we showed recently that S-SMase can extensively hydrolyze the SM of atherogenic lipoproteins (e.g., oxidized LDL) and lesional LDL at neutral pH (16). This point is of particular importance regarding our hypothesis that endothelial-derived S-SMase plays a role in early lesional events, where the arterial-wall pH would be expected to be neutral. These observations may also be relevant to the hydrolysis of cellular sphingomyelin by endothelial-derived S-SMase in neutral-pH environments.

In summary, endothelial cells, which we have postulated are important in subendothelial, extracellular lipoprotein-SM hydrolysis and which others have shown are important in cytokine-induced, ASM-mediated cell signalling, are a rich and regulatable source of the ASM gene product, S-SMase. These findings have formed the basis of ongoing work directed at further testing the physiologic and pathophysiologic roles of endothelial-derived S-SMase.

EXAMPLE 6

Secretory Sphingomyelinase (S-Mase), an Enzyme Impliated in Atherogenesis, is Present in Atherosclerotic Lesions and Binds to Extracellular Matrix In vitro, Smase causes lipoprotein aggregation, which is a key feature of atheromata and an inducer of foam cells. In vivo, aggregated LDL from human lesions, but not unaggregated lesional LDL or plasma LDL, shows evidence of SM hydrolysis (JCI 98:1455). We have identified S-Mase (JBC 271:18431) as a candidate for this arterial Smase, owing to its secretion by endothelial cells (ECs) and macrophages and for its ability to hydrolzye atherogenic lipoproteins (JBC 273:2738 & 4081). We addressed two questions critical to the role of S-SMase in atherogenesis: is S-SMase present in lesions and does S-SMase bind matrix after secretion? Using two different anti-SMase antibodies, Smase staining was prominent in the endothelium of normal rabbit and mouse aorta. In atherosclerotic aorta from cholesterol-fed rabbits and apoE knockout mice and in human coronary lesions, there was very heavy Smase staining throughout the entire intima (endothelium and foam cells). In both normal and lesional aorta, there was staining of the mdia but far less than in the intima. Some of the SMase pattern suggested association with matrix. To explore this point in vitro, $^{125}$I-S-SMase was incubated with matrix derived from cultured smooth muscle or Ecs. With both, the moles of bound $^{125}$I-S-SMase were≧bound $^{125}$I-LDL, which is known to associate with matrix in vitro and in vivo. Like LDL S-Smase binding was enhanced by lipoprotein lipase Chondroitinase and heparitinase treatment of EC matrix blocked S-Mase binding by 0% and 20%, respectively, suggesting Interaction with mostly non-glycosaminoglycans. In summary, Smase, an enzyme implicated in atherogenesis, is present in normal endothelium and especially lesional intima, and there is evidence that S-Mase binds matrix both in vivo and in vitro.

References for Example 5

1. Spence, M. W. (1993) *Adv. Lipid Res.* 26, 3–23
2. Xu, X. and Tabas, I. (1991) *J. Biol. Chem* 266; 24849–24858
3. Tabas, I., Li, Y., Brocia, R. W., Wu, S. W., Swenson, T L., and Williams, K. J. (1993) *J. Biol. Chem.* 268, 20419–20432
4. Schissel, S. L., Tweedie-Hardman, J., Rapp, J. H., Graham, G., Williams, K. J., and Tabas, I. (1996) *J. Clin. Invest.* 98, 1455–1464
5. Williams, K. J. and Tabas, I. (1995) *Arterioscler. Thromb. Vasc. Biol.* 15, 551–561
6. Hannun, Y. A. (1996) *Science* 274, 1855–1859
7. Spiegel, S., Foster, D. A., and Kolesnick, R. N. (1996) *Curr. Opin. Cell Biol.* 8, 159–167
8. Ballou, L. R., Laulederkind, S. J., Rosloniec, E. F., and Raghow, R. (1996) *Biochim,. Biophys. Acta* 1301, 273–287
9. Hoff, H. F. and Morton, R. E. (1985) *Ann. N.Y. Acad. Sci.* 454, 183–194
10. Nievelstein, P. F. E. M., Fogelman, A. M., Mottino, G., and Frank, J. S. (1991) *Arteriosclerosis and Thrombosis* 11, 1795–1805
11. Guyton, J. R. and Klemp, K. F. (1996) *Arterioscler. Thromb. Vasc. Biol.* 16, 4–11
12. Hoff, H. F., O'Neill, J., Pepin, J. M., and Cole, T. B. (1990) *Eur. Heart J.* 11, 105–115
13. Khoo, J. C., Miller, E., McLoughlin, P., and Steinberg, D. (1988) *Arteriosclerosis* 8, 348–358
14. Suits, A. G., Chait, A., Aviram, M., and Heinecke, J. W. (1989) *Proc. Natl. Acad. Sci. USA* 86, 2713–2717
15. Schissel, S. L., Schuchman, E. H., Williams, K. J., and Tabas, I. (1996) *J. Biol. Chem.* 271, 18431–18436
16. Schissel, S. L., Jiang, X. C., Tweedie-Hardman, J., Jeong, T. S., Camejo, E. H., Najib, J., Rapp, J. H., Williams, K. J., and Tabas, I. (1998) *J. Biol. Chem.*
17. Cifone, M. G., De Maria, R., Roncaioli, P., Rippo, M. R., Azuma, M., Lanier, L. L., Santoni, A., and Testi, R. (1994) *J. Exp. Med.* 180, 1547–1552
18. Cifone, M. G., Roncaioli, P., De Maria, R., Camarda, G., Santoni, A., Ruberti, G., and Testi, R. (1995) *EMBO J.* 14, 5859–5868
19. Wiegmann, K., Schutze, S., Machleidt, T., Witte, D., and Kronke, M. (1994) *Cell* 78, 1005–1015
20. Santana, P., Pena, L. A., Haimovitz-Friedman, A., Martin, S., Green, D., McLoughlin, M., Cordon-Cardo, C., Schuchman, E. H., Fuks, Z., and Kolesnick, R. (1996) *Cell* 86, 189–199
21. Haimovitz-Friedman, A., Cordon-Cardod, C., Bayoumyb, S., Garzotrob, M., McLoughlin, M., Gallily, R., Edwards, C. K., III, Schuchman, E. H., Fuks, Z., and Kolesnick, R. (1997) *J. Exp. Med.*
22. Merrill, A. H. and Jones, D. D. (1990) *Biochim. Biophys. Acta* 1044, 1–12
23. Ross, R. (1995) *Annual Review of Physiology* 57, 791–804
24. Pober. J. S. and Cotran, R. S. (1991) *Adv. Immunol.* 50. 261–302
25. Mantovani, A., Sozzani, S., Vecchi, A., Introna, M., and Allavena, P. (1997) *Thromb. Haem.* 78, 406–414
26. Libby, P. and Hansson, G. K. (1991) *Lab. Invest.* 64, 5–15
27. Ware, C. F., VanArsdale, S., and VanArsdale, T. L. (1996) *J. Cell. Biochem.* 60, 47–55
28. Sripada, P. K., Maulik, P. R., Hamilton, J. A., and Shipley, G. G. (1987) *J. Lipid Res.* 28, 710–718
29. Ahmad, T. Y., Sparrow, J. T., and Morrisett, J. D. (1985) *J. Lipid Res.* 26, 1160–1165
30. Varki, A. and Kornfeld, S. (1983) *J. Biol. Chem.* 258, 2808–2818
31. Yellin, M. J., Brett, J., Baum, D., Matsushima, A., Szabolcs, M., Stern, D., and Chess, L. (1995) *J. Exp. Med.* 182, 1857–1864
32. Cornicelli, J. A., Witte, L. D., and Goodman, D. S. (1983) *Arteriosclerosis* 3, 560–567
33. Khoo, J. C., Miller, E., McLoughlin, P., Tabas, I., and Rosoff, W. J. (1989) *Biochim. Biophys. Acta* 1012, 215–217
34. Okwu, A. K., Xu, X., Shiratori, Y., and Tabas, I. (1994) *J. Lipid Res.* 35. 644–655
35. Bottalico, L. A., Keesler, G. A., Fless. G. M., and Tabas, I. (1993) *J. Biol. Chem.* 268, 8569–8573
36. Fogelmar., A. M., Haberland, M. E., Seager, J., Hokom. M., and Edwards, P. A. (1981) *J. Lipid Res.* 22, 113–1141
37. Bligh, E. G. and Dyer, W. J. (1959) *Can. J. Biochem. Physiol.* 37, 911–917
38. Nakashima, Y., Plump, A. S., Raines, E. W., Breslow, J. L., and Ross, R. (1994) *Arterioscler.Thromb.* 14, 133–140
39. Levade, T., Salvayre, R., and Blazy-Douste, L. (1986) *J. Clin. Chem. Biochem.* 24, 205–220
40. Lowry, O. H., Rosenbrough, N. J., Farr, A. L., and Randall, R. J. (1951) *J. Biol. Chem.* 193, 265–275
41. Schuchman, E. H., Suchi, M., Takahashi, T., Sandhoff, K., and Desnick, R. J. (1991) *J. Biol. Chem.* 266, 8531–8539
42. Tabas, I., Marathe, S., Keesler, G. A., Beazini, N., and Shiratori, Y. (1996) *J. Biol. Chem.* 271, 22773–22781
43. Spence, M. W., Byers, D. M., St.C.Palmer, F. B., and Cook, H. W. (1989) *J. Biol. Chem.* 264, 5358–5363
44. Horinouchi, K., Erlich, S., Perl, D., Ferlinz, K., Bisgaier, C. L., Sandhoff, K., Desnick, R. J., Stewart, C. L., and Schuchman, E. H. (1995) *Nature Gen.* 10, 288–293
45. Perregaux, D. G., Laliberte, R. E., and Gabel, C. A. (1996) *J. Biol. Chem.* 271, 29830–29838
46. Ioannou, Y. A., Bishop, D. F., and Desnick. R. J. 1992) *J. Cell Biol.* 119, 1137–1150
47. Baron, R., Neff, L., Louvard, D., and Courtoy, F. J. (1985) *J. Cell Biol.* 101, 2210–2222
48. Faust, P. L., Wall, D. A., Perara, E., Lingappa, V. R., and Kornfeld, S. (1987) *J. Cell Biol.* 105, 1937–1945
49. Mohan Das, D. V., Cook, H. W., and Spence, M. W. (1984) *Biochim. Biophys. Acta* 777, 339–342
50. Urade, R., Hayashi, Y., and Kito, M. (1988) *Biochim. Biosphys. Acta* 946, 151–163
51. Zhang, F., Liu, B., Jenkins, G. M., Hannun, Y. A., and Obeid, L. M. (1997) *J. Biol. Chem.* 272, 9609–9612
52. Hurwitz, R., Ferlinz, K., Vielhaber, G., Moczall, H., and Sandhoff, K. (1994) *J. Biol. Chem.* 269, 5440–5445
53. Kornfeld, S. (1987) *FASEB J.* 1, 462–468

54. Donangelo, C. M. and Chang, G. W. (1981) *Clin. Chim. Acta* 113, 201–206
55. Sorbi, D., Fadly, M., Hicks, R., Alexander, S., and Arbeit, L. (1993) *Kidney Int.* 44, 1266–1272
56. Galis, Z. S., Sukhova, G. K., Lark, M. W., and Libby, P. (1994) *J. Clin. Invest.* 94, 2493–2503
57. Mondis, S. (1989) *Biol. Trace Element Res.* 22, 251–256
58. Milanino, R., Moretti, U., Concari, E., Marrella, M., and Velo, G. P. (1988) *Agents & Actions* 24. 365–376
59. Cousins, R. J. and Leinart, A. S. (1988) *FASEB J.* 2. 2884–2890
60. Smith. E. B. (1979) *Adv. Exp. Med. Biol.* 115, 245–297
61. Maroudas, A., Weinberg, P. D., Parker, K. H., and Winlove, C. P. (1988) *Biophys. Chem.* 32, 257–270
62. Tapper, H. and Sundler, R. (1992) *Biochem. J.* 281, 245–250
63. Silver, I. A., Murrills, R. J., and Etherington, D. J. (1988) *Exp. Cell Res.* 175, 266–276
64. Menkin, V. (1934) *Am. J. Pathol.* 10, 193–210
65. Callahan, J. W., Jones, C. S., Davidson, D. J., and Shankaran, P. (1983) *J. Neurosci. Res.* 10, 151–163

References for Examples 1–4

Ahmad, T. Y., J. T. Sparrow, and J. D. Morrisett. 1985. Fluorine-, pyrene- and nitroxide-labeled sphingomyelin: semisynthesis and thermotropic properties. *J. Lipid Res.* 26:1160–1165.

Ahmad, T. Y., A. L. Beaudet, J. T. Sparrow, and J. D. Morrisett. 1986. Human lysosomal sphingomyelinase substrate efficacy of apolipoprotein/sphingomyelin complexes. *Biochemistry* 25:4415–4420.

Aloia, R. C., Jensen, F. C., Curtain, C. C., Mobley, P. W., and Gordon, L. M. (1988) *Proc. Natl. Acad. Sci. USA* 85, 900–904.

Baranski, T. J., Cantor, A. B., and Kornfeld, S. (1992) *J. Biol. Chem.* 267, 23342–23348.

Bartlett, G. R. 1959. Phosphorus assay in column chromatography, *J. Biol. Chem.* 234:466–468.

Bauer, J., Sminia, T., Wouterlood, F. G., and Dijkstra, C. D. (1994) *J. Neurosci. Res.* 38, 365–375.

Bernardo, K., R. Hurwitz, T. Zenk, R. J. Desnick, K. Ferlinz, E. H. Schuchman, and K. Sandhoff. 1995. Purification, characterization, and biosynthesis of human acid ceramidase. *J. Biol. Chem.* 270:11098–11102.

Bettger, W. J. and O'Dell, B. L. (1981) *Life Sci.* 28, 1425–1438.

Bligh, E. G. and Dyer, W. J. (1959) *Can. J. Biochem. Physiol.* 37, 911–917.

Blondelle, S. E. et al., (1994) *Antimicrobial Agents and Chemotherapy* 38, 2280–2286.

Bowness, J. M., A. H. Tarr, and R. I. Wiebe. 1989. Transglutaminase-catalysed cross-linking: a potential mechanism for the interaction or fibrinogen, low density lipoprotein and arterial type III procollagen. *Thromb. Res.* 54:357–367.

Bowser, P. A. and Gray, G. M. (1978) *J. Invest. Dermatol* 70, 331–335.

Brady, R. O. (1983) in *The metabolic basis of inherited disease* (Stanbury, J. B., Wyngarden, J. B., Fredrickson, D. S., Goldstein, J. L., and Brown, M. S. eds) pp. 831–841, McGraw-Hill, New York Brand, I. A. and Kleineke, J. (1996) *J. Biol. Chem.* 271, 1941–1949.

Callahan, j. W., C. S. Jones, D. J. Davidson, and P. Shankaran. 1983. The active site of lysosomal sphingomyelinase: evidence for the involvement of hydrophobic and ionic groups. *J. Neurosci. Res.* 10:151–163.

Callahan, J. W., Shankaran, P., Khalil, M., and Gerrie, J. (1978) *Can. J. Biochem.* 56, 885–891.

Camejo, G., E. Hurt-Camejo, U. Olsson, and G. Bondjers. 1993. Proteoglycans and lipoproteins in atherosclerosis. *Curr. Opin. Lipidol.* 4:385–391.

Cantor, A. B., Baranski, T. J., and Kornfeld, S. (1992) *J. Biol. Chem.* 267, 23349–23356.

Chatterjee, S. 1993. Neutral sphingomyelinase. *Adv. Lipid Res.* 26:25–48.

Cifone, M. G., Roncaioli, P., De Maria, R. Camarda, G., Santoni, A., Ruberti, G., and Testi, R. (1995) *EMBO J.* 14. 5859–5868.

Clavey, V., S. Lestavel-Delattre, C. Copin, J. M. Bard, and J. C. Fruchart. 1995. Modulation of lipoprotein B binding to the LDL receptor by exogenous lipids and apolipoproteins CI, CII, CIII, and E. *Arterioscler. Thromb. Vasc. Biol.* 15:963–971.

Csermely, P., Fodor, P., and Somogyi, J. 11987) *Carcinogenesis* 8, 1663–1666.

Dallinga-Thie, G. M., M. van Linde-Sibenius Trip, J. I. Rotter, R. M. Cantor, X. Bu, A. J. Lusis, and T. W. de Bruin. 1997. Complex genetic contribution of the Apo AI-CIII-AIV gene cluster to familial combined hyperlipidemia. Identification of different susceptibility haplotypes. *J. Clin. Invest.* 99:953–961.

Dammerman, M., L. A. Sandkuijl, J. L. Halaas, W. Chung, and J. L. Breslow. 1993. An apolipoprotein CIII haplotype protective against hypertriglyceridemia is specified by promoter and 3' untranslated region polymorphisms. *Proc. Natl. Acad. Sci. USA* 90:4562–4566.

Danscher, G., Howell, G., Perez-Clausell, J., and Hertel, N. (1985) *Histochemistry* 83, 419–422.

Daugherty, A., B. S. Zweifel, B. E. Sobel, and G. Schonfeld. 1988. Isolation of low density lipoprotein from atherosclerotic vascular tissue of Watanabe heritable hyperlipidemic rabbits. *Arteriosclerosis* 8:768–777.

Dustin, M., L., Baranski, T. J., Sampath. D., and Kornfeld, S. 11995) *J. Biol. Chem.* 270, 170–179.

Dzeletovic, S., A. Babiker, E. Lund, and U. Diczfalusy. 1995. Time course of oxysterol formation during in vitro oxidation of low density lipoprotein. *Chem. Phys. Lipids* 78:119–128.

el-Saadani, M., H. Esterbauer, M. el-Sayed, M. Goher, A. Y. Nassar, and G. Jurgens. 1989. A spectrophotometric assay for lipid peroxides in serum lipoproteins using a commercially available reagent. *J. Lipid Res.* 30:627–630.

Esterbauer, H., G. Jurgens, 0. Quehenberger, and E. Koller. 1987. Autoxidation of human low density lipoprotein: loss of polyunsaturated fatty acids and vitamin E and generation of aldehydes. *J. Lipid Res.* 28:495–509.

Faust, P. L., Wall, D. A., Perara, E., Lingappa, V. R., and Kornfeld, S. (1987) *J. Cell Biol.* 105, 1937–1945.

Francis, S. H., Colbran, J. L., McAllister-Lucas, L. M., and Corbin, J. D. (1994) *J. Biol. Chem.* 269, 22477–22480.

Geng, Y. and P. Libby. 1995. Evidence for apoptosis in advanced human atheroma. Colocalization with interleukin-1b-converting enzyme. *Am. J. Pathol.* 147:251–266.

Goldberg, I. J. 1996. Lipoprotein lipase and lipolysis: central roles in lipoprotein metabolism and atherogenesis. *J. Lipid Res.* 37:693–707.

Goldstein, J. L., M. S. Brown, R. G. W. Anderson, D. W. Russell, and W. J. Schneider. 1985. Receptor-mediated endocytosis: concepts emerging from the LDL receptor system. *Annu. Rev. Cell Biol.* 1:1–39.

Goldstein, J. L., S. K. Basu, and M. S. Brown. 1983 Receptor-mediated endocytosis of low density lipoprotein in cultured cells. *Methods Enzymol.* 98:241–260.

Goldstein, J. L. and M. S. Brown. 1977. The low-density lipoprotein pathway and its relation to atherosclerosis. *Annu. Rev. Biochem.* 46:897–930.

Goldstein, J. L., Y. K. Ho, S. K. Basu, and M. S. Brown 1979. Binding site on macrophages that mediates uptake and degradation of acetylated low density lipoprotein producing massive cholesterol deposition. *Proc. Natl. Acad. Sci. USA* 76:333–337.

Guyton, J. R. and K. F. Klemp. 1996. Development of the lipid-rich core in human atherosclerosis. *J. Lipid Res.* 16:4–11.

Han, D. K. M., C. C. Haudenschild, M. K. Hong, B. T. Tinkle, M. B. Leon, and G. Liau. 1995. Evidence for apoptosis in human atherogenesis and in a rat vascular injury model. *Am. J. Pathol.* 147:267–277.

Hannun, Y. A. and R. M. Bell. 1989. Functions of sphingolipids and sphingolipid breakdown products in cellular regulation. *Science* 243:500–507.

Hartung, H. P., Jung, S., Stoll, G., Zielasek, J., Schmidt, B., Archelos, J. J., and Toyka, K. V. (1992) *J. Neuroimmunol.* 40, 197–210

Hasilik, A. (1992) *Experientia* 48, 130–151.

Havel, R. J., H. Eder, and J. Bragdon. 1955. The distribution and chemical composition of ultracentrifugally reported lipoproteins in human serum. *J. Clin. Invest.* 34:1345–1353.

Hoff, H. F., J. O'Neill, G. M. Chisolm,III, T. B. Cole, C. Quehenberger, H. Esterbauer, and G. Jürgens. 1989. Modification of low density lipoprotein with 4-hydroxynonenal induces uptake by macrophages *Arteriosclerosis* 9:538–549.

Hoff, H. F. 1983. LDL in the arterial wall: Localization. quantitation, and characterization. In Handbook of electrophoresis. Vol. III. Lipoprotein methodology and human studies. L. A. Lewis, editor. CRC Press, Boca Raton, Fla. 133–165.

Hoff, H. F. and R. E. Morton. 1985. Lipoproteins containing apo B extracted from human aortas: structure and function. *Ann. N.Y. Acad. Sci.* 454:183–194.

Hoff, H. F., J. O'Neill, J. M. Pepin, and T. B. Cole. 1990. Macrophage uptake of cholesterol-containing particles derived from LDL and isolated from atherosclerotic lesions. *Eur. Heart J.* 11:105–115.

Horinouchi, K., Erlich, S., Perl, D., Ferlinz, K., Bisgaier, C. L., Sandhoff, K., Desnick, R. J., Stewart, C. L., and Schuchman, E. H. (1995) *Nature Gen.* 10, 288–293.

Hortin, G. L. and Gibson, B. L. (1989) *Prep. Biochem.* 19, 49–59.

Hough, E., Hansen, L. K., Birknes, B., Jynge, K., Hansen, S., Hordvik, A., Little, C., Dodson, E., and Derewenda, Z. (1989) *Nature* 338, 357–360.

Hung, C.-H., Huang, H.-R., Huang, C.-J., Huang, F.-L., and Chang, G.-D. (1997) *J. Biol. Chem.* 272, 13772–13778.

Hurt-Camejo, E., S. Andersen, R. Standal, B. Rosengren, P Sartipy, E. Stadberg, and B. Johansen. 1997. Localization of nonpancreatic secretory phospholipase $A_2$ in normal and atherosclerotic arteries. *Arterioscler. Thromb. Vasc. Biol.* 17:300–309.

Hurwitz, R., Ferlinz, K., Vielhaber, G., Moczall, H. and Sandhoff, K. (1994) *J. Biol. Chem.* 269, 5440–5445.

Ikezawa, H., M. Matsushita, M. Tomita, and R. Taguchi. 1986. Effects of metal ions on sphingomyelinase activity of *Bacillus cereus*. *Arch. Biochem,. Biophys.* 249:588–595.

Ioannou, Y. A., Bishop, D. F., and Desnick, R. J. (1992) *J. Cell Biol.* 119, 1137–1150.

Ishibashi, S., M. S. Brown, J. L. Goldstein, R. D. Gerard, R. E. Hammer, and J. Herz. 1993. Hypercholesterolemia in low density lipoprotein receptor knockout mice and its reversal by adenovirus-mediated gene delivery. *J. Clin. Invest.* 92:883–893.

Ito, Y., N. Azrolan, A. O'Connell, A. Walsh, and J. L. Breslow. 1990. Hypertriglyceridemia as a result of human apo CIII gene expression in transgenic mice. *Science* 249:790–793.

Ivandic, B., F. C. deBeer, M. C. deBeer, L. Castellani, N. Leitinger, S. Y. Hama, J. Lee, X. Wang, M. Navab, A. M. Fogelman, and A. J. Lusis. 1996. Transgenic mice overexpressing secretory phospholipase A2 develop markedly increased aortic fatty streak lesions. *Circulation* 94:I-152 (Abstr.).

Jonasson, L., G. Bondjers, and G. K. Hansson. 1987. Lipoprotein lipase in atherosclerosis: its presence in smooth muscle cells and absence from macrophages. *J. Lipid Res.* 28:437–445.

Kaartinen, M., A. Penttila, and P. T. Kovanen 1994. Mast cells of two types differing in neutral protease composition in the human aortic intima. Demonstration of tryptase- and tryptase/chymase-containing mast cells in normal intimas, fatty streaks, and the shoulder region of atheromas. *Arterioscler. Thromb.* 14:966–972.

Kempf et al. (1991) *Intl. J. Peptide and Prot. Res.* 38, 237–241.

Khoo, J. C., E. Miller, P. McLoughlin, and D. Steinberg. 1986. Enhanced macrophage uptake of low density lipoprotein after self-aggregation. *Arteriosclerosis* 8:348–358.

Khoo, J. C., E. Miller, P. McLoughlin, and D. Steinberg. 1990. Prevention of low density lipoprotein aggregation by high density lipoprotein or apolipoprotein A–I. *J. Lipid Res.* 31:645–652.

Khoo, J. C., Miller, E., McLoughlin, P., Tabas, I., and Rosoff, W. J. (1989) *Biochim. Biophys. Acta* 1012, 215–217.

Kolesnick, R. N. 1991. Sphingomyelin and derivatives as cellular signals. *Prog. Lip d Res.* 30:1–38.

Kornfeld, S. (1987) *FASEB J.* 1, 462–468.

Kreuzer, J., M. B. Lloyd, D. Bok, G. M. Fless, A. M. Scanu, A. J. Lusis, and M. E. Haberland. 1994. Lipoprotein(a) displays increased accumulation compared with low-density lipoprotein in the murine arterial wall. *Chem. Phys. Lipids* 67/68:175–190.

Krieger, M. and J. Herz. 1994. Structures and functions of multiligand lipoprotein receptors: macrophage scavenger receptors and LDL receptor-related protein (LRP) *Annu. Rev. Biochem.* 63:601–637.

Leeuwenburgh, C., J. E. Rasmussen, F. F. Hsu, D. M. Mueller S. Pennathur, and J. W. Heinecke. 1997. Mass spectrometric quantification of markers for protein oxidation by tyrosyl radical, copper, and hydroxyl radical in low density lipoprotein isolated from human atherosclerotic plaques. *J. Biol. Chem.* 272:3520–3526.

Levade, T., Salvayre, R., and Blazy-Douste, L. (1986) *J. Clin. Chem. Biochem.* 24, 205–220.

Levran, O., Desnick, R. J., and Schuchman, E. H. (1991) *Proc. Natl. Acad. Sci. USA* 88, 3748–3752.

Libby, P. and G. K. Hansson. 1991. Involvement of the immune system in human atherogenesis: current knowledge and unanswered questions. *Lab. Invest.* 64:5–15.

Little, C. and Otnass, A. (1975) *Biochim. Biophys. Acta* 391, 329–333.

Lougheed, M. and U. P. Steinbrecher. 1996. Mechanism of uptake of copper-oxidized low denisty lipoprotein in macrophages is dependent on its extent of oxidation. *J. Biol. Chem.* 271:11798–11805.

Maroudas, A., P. D. Weinberg, K. H. Parker, and C. P. Winlove. 1988. The distributions and diffusivities of small ions in chondroitin sulphate, hyaluronate and some proteoglycan solutions. *Biophys. Chem.* 32:257–270.

Masucci-Magoulas, L., I. J. Goldberg, C. L. Bisgaier, H. Serajuddin, O. L. Francone, J. L. Breslow, and A. R. Tall. 1997. A mouse model with features of familial combined hyperlipidemia. *Science* 275:391–394.

Menkin, V. 1934. Studies on inflammation. X. The cytological picture of an inflammatory exudate in relation to its hydrogen ion concentration. *Am. J. Parthol.* 10.193–210.

Merrill, A. H. and D. D. Jones. 1990. An update of the enzymology and regulation of sphingomyelin metabolism. *Biochim. Biophys. Acta* 1044:1–12.

Mohan Das, D. V., H. W. Cook, and M. W. Spence. 1984. Evidence that neutral sphingomyelinase of cultured murine neuroblastoma cells is oriented externally on the plasma membrane. *Biochim. Biophys. Acta* 777:339–342.

Nagase, H., Suzuki, K., Itoh, Y., Kan, C. C., Gehring, M. R., Huang, W., and Brew, K. (1996) *Adv. Exp. Med. Biol.* 389, 23–31

Neufeld, E. F. (1980) *Birth Defects* 16, 77–84.

Newrzella, D. and Stoffel, W. (1996) *J. Biol. Chem.* 271, 32089–32095.

Nievelstein, P. F. E. M., A. M. Fogelman, G. Mottino, and J. S. Frank. 1991. Lipid accumulation in rabbit aortic intima 2 hours after bolus infusion of low density lipoprotein. *Arter. Thromb.* 11:1795–1805.

Nievelstein-Post, P., G. Mottino, A. Fogelman, and J. Frank. 1994. An ultrastructural study of lipoprotein accumulation in cardiac valves of the rabbit. *Arter. Thromb.* 14:1151–1161.

Niewoehner, D. E., K. Rice, P. Duane, A. A. Sinha. R. Gebhard, and D. Wangensteen. 1989- Induction of alveolar epithelial injury by phospholipase $A_2$. *J. Appl. Physiol.* 66:261–267.

Okazaki, T., A. Bielawska, N. Domae, R. M. Bell, and Y. A. Hannun. 1994. Characteristics and partial purification of a novel cytosolic, magnesium-independent, neutral sphingomyelinase activated in the early signal transduction of $1a,25$-dihydroxyvitamin $D_3$-induced HL-60 cell differentiation. *J. Biol. Chem.* 269:4070–4077.

Okwu, A. K., X. Xu, Y. Shiratori, and I. Tabas. 1994. Regulation of the threshold for lipoprotein-induced acyl-CoA:cholesterol O-acyltransferase stimulation in macrophages by cellular sphingomyelin content. *J. Lipid Res.* 35:644–655.

Otterbach, B. and Stoffel, W. (1995) *Cell* 81, 1053–1061

Panchenko, M. V., Stetler-Stevenson, W. G., Trubetskoy, O. V., Gacheru, S. N., and Kagan, H. M. (1996) *J. Biol. Chem.* 271, 7113–7119.

Parthasarathy, S., U. P. Steinbrecher, J. Barnett, J. L. Witztum, and D. Steinberg. 1985. Essential role of phospholipase A2 activity in endothelial cell-induced modification of low density lipoprotein. *Proc. Natl. Acad. Sci. USA* 82:3000–3004.

Pinilla, C., et al. (1995) *Peptide Science* 37, 221–240.

Plump, A. S., J. D. Smith, T. Hayek, K. Aalto-Setala, A. Walsh, J. C. Verstuyft, E. M. Rubin, and J. L. Breslow. 1992. Severe hypercholesterolemia and atherosclerosis in apolipoprotein E-deficient mice created by homologous recombination en ES cells. *Cell* 71:343–353.

Plump: A. S., C. J. Scott, and J. L. Breslow. 1994. Human apolipoprotein A-I gene expression raises HDL and suppresses atherosclerosis in the apo E-deficient mouse. *Proc. Natl. Acad. Sci. USA* 91:9607–9611.

Porn, M. I. and Slotte, J. P. (1995) *Biochem. J.* 308:269–274.

Portman, O. W. and M. Alexander. 1970. Metabolism of sphingolipids by normal and atherosclerotic aorta of squirrel monkeys. *J. Lipid Res.* 11:23–30.

Preiss, J., C. R. Loomis, W. R. Bishop, R. Stein, J. E. Niedel, and R. M. Bell. 1986. Quantitative measurement of sn-1, 2-diacylglycerols present in platelets, hepatocytes, and ras- and sis-transformed normal rat kidney cells. *J. Biol. Chem.* 261:8597–8600.

Puhl, H., G. Waeg, and H. Esterbauer. 1994. Methods to determine oxidation of low-density lipoproteins. *Methods Enzymol.* 233:425–441.

Quinn, M. T., S. Parthasarathy, and D. Steinberg. 1988. Lysophosphatidylcholine: a chemotactic factor for human monocytes and its potential role in atherogenesis. *Proc. Natl. Acad. Scd. USA* 85:2805–2809.

Rao, B. G. and Spence, M. W. (1976) *J. Lipid Res.* 17, 506–515.

Rapp, J. H., A. Lespine, R. L. Hamilton, N. Colyvas, A. H. Chaumeron, J. Tweedie-Hardman, L. Kotite, S. T. Kunitake, R. J. Havel, and J. P. Kane. 1994. Triglyceride-rich lipoproteins isolated by selected-affinity anti-apolipoprotein B immunosorption from human atherosclerotic plaque. *Arteriosclerosis and Thrombosis* 14:1767–1774.

Reynolds, J. J. (1996) *Oral Diseases* 2, 70–76.

Rigoli, L., G. Raimondo, A. Di Benedetto, G. Romano, A. Procellini, S. Campo, F. Corica, G. Riccardi, G. Sauadrito, and D. Cucinotta. 1995. Apolipoprotein AI-CII-AIV genetic polymorphisms and coronary heart disease in type 2 diabetes mellitus. *Acta Diabetologica* 32:251–256.

Ross, R. 1995. Cell biology of atherosclerosis. *Annual Review of Physiology* 57:791–804.

Rubin, E. M.; R. M. Krauss, E. A. Spangler, J. G. Verstuyft, and S. M. Clift. 1991. Inhibition off early atherogenesis in transgenic mice by human apolipoprotein AI. *Nature* 353:265–267.

Sartipy, P., P. Johansen, C. Camejo, B. Rosengren, G. Bondjers, and E. Hurt-Camejo. 1996. Binding of human phospholipase $A_2$ type II to proteoglycans. Differential effect of glycosaminoglycans on enzyme activity. *J. Biol. Chem.* 271:26307–26314.

Schissel, S. L., E. H. Schuchman, K. J. Williams, and I. Tabas. 1996. $Zn^{2+}$ stimulated sphingomyelinase is secreted by many cell types and is a product of the acid sphingomyelinase gene. *J. Biol. Chem.* (In Press)

Schissel, S. L., Schuchman, E. H., Williams, K. J., and Tabas, I. (1996) *J. Biol. Chem.* 271, 18431–18436

Schissel, S. L., J. Tweedie-Hardman, J. H. Rapp, G. Graham, K. J. Williams, and I. Tabas. 1996. Rabbit aorta and human atherosclerotic lesions hydolyze the sphingomyelin of retained low-density lipoprotein. Proposed role for arterial-wall sphingomyelinase in subendothelial retention and aggregation of atherogenic lipoproteins. *J. Clin. Invest.* 98:1455–1464.

Schneider, E. G. and E. P. Kennedy. 1976. Partial purification and properties of diglyceride kinase from *Escherichia coli. Biochim. Biophys. Acta* 441:201–212.

Schneider, P. B. and Kennedy, E. P. (1967) *J. Lipid Res.* 8, 202–209

Schuchman, E. H., M. Suchi, T. Takahashi, K. Sandhoff, and R. J. Desnick. 1991. Human acid sphingomyelinase. Isolation, nucleotide sequence, and expression of the full-length and alternatively spliced cDNAs. *J. Biol. Chem.* 266:8531–8539.

Schwenke, D. C. and T. E. Carew. 1989. Initiation of atherosclerotic lesions in cholesterol-fed rabbits. II. Selective retention of LDL vs. selective increases in LDL permeability in susceptible sites of arteries. *Arteriosclerosis* 9:908–918.

Schwenke, D. C. and T. E. Carew. 1989. Initiation of atherosclerotic lesions in cholesterol-fed rabbits: I. Focal increases in arterial LDL concentrations precede development of fatty streak lesions. *Arteriosclerosis* 9:895–907.

Silver, I. A., R. J. Murrills, and D. J. Etherington. 1988. Microelectrode studies on the acid microenvironment beneath adherent macrophages and osteoclasts. *Exp. Cell Res.* 175:266–276.

Skiba, P. J., X. Zha, S. L. Schissel, F. R. Maxfield, and I. Tabas. 1996. The distal pathway of lipoprotein-induced cholesterol esterification, but not sphingomyelinase-induced cholesterol esterification, is energy-dependent. *J. Biol. Chem.* 271:13392–13400.

Slotte, J. P. and Bierman, E. L. (1988) *Biochem. J.* 250, 653–658.

Smith, E. B. 1979. Metabolic activities in the arterial wall. *Adv,. Exp. Med. Biol.* 115:245–297.

Spence, M. W., J. K. Burgess, and E. P. Sperker. 1979. Neutral and acid sphingomyelinases: somatotopographical distribution in human brain and distribution in rat organs. A possible relationship with the dopamine system. *Brain Res.* 168:543–551.

Spence, M. W., D. M. Byers, F. B. St.C.Palmer, and H. W. Cook. 1989. A new $Zn^{2+}$ stimulated sphingomyelinase in fetal bovine serum. *J. Biol. Chem.* 264:5358–5363.

Spence, M. W. 1993. Sphingomyelinases. *Adv. Lipid Res.* 26:3–23.

Sripada, P. K., P. R. Maulik, J. A. Hamilton, and G. G. Shipley. 1987. Partial synthesis and properties of a series of N-acylsphingomyelins. *J. Lipid Res.* 28:710–718.

Steinberg, D., S. Parthasarathy, T. E. Carew, J. C. Khoo, and J. L. Witztum. 1989. Beyond cholesterol: modifications of low-density lipoprotein that increase its atherogenicity. *N. Engl. J. Med.* 320:915–924.

Steinbrecher, U. P., J. L. Witztum, S. Parthasarathy, and D. Steinberg. 1987. Decrease in reactive amino groups during oxidation or endothelial cell modification of LDL. Correlation with changes in receptor-mediated catabolism. *Arteriosclerosis* 7:135–143.

Suits, A. G., A. Chait, M. Aviram, and J. W. Heinecke. 1989. Phagocytosis of aggregated lipoprotein by macrophages: low density lipoprotein receptor-dependent foam-cell formation. *Proc. Natl. Acad. Sci. USA* 86:2713–2717.

Svensson, M., Eriksson, P., Persson, J. K., Molander, C., Arvidsson, J., and Aldskogius, H. (1993) *Brain, Res,. Bull.* 30, 499–506.

Tabas, I., Y. Li, R. W. Brocia, S. W. Wu, T. L. Swenson, and K. J. Williams. 1993. Lipoprotein lipase and sphingomyelinase synergistically enhance the association of atherogenic lipoproteins with smooth muscle cells and extracellular matrix. A possible mechanism for low density lipoprotein and lipoprotein(a) retention and macrophage foam cell formation. *J. Biol. Chem.* 268:20419–20432.

Tall, A. R. 1990. Plasma high density lipoproteins. Metabolism and relationship to atherogenesis. *J. Clin. Invest.* 86:379–384.

Tapper, H. and R. Sundler. 1992. Cytosolic pH regulation in mouse macrophages. Proton extrusion by plasma-membrane-localized H(+)-ATPase. *Biochem. J.* 281:245–250.

Tollefson, J. H., S. Ravnik, and J. J. Albers. 1988. Isolation and characterization of a phospholipid transfer protein (LTP-II) from human plasma. *J. Lipid Res.* 29:1593–1602.

Tsukamoto, Y., K. Kuwabara, S. Hirota, J. Ikeda, D. Stern, H. Yanagi, M. Matsumoto, S. Ogawa, and Y. Kitamura. 1996. 150-kD oxygen-regulated protein is expressed in human atherosclerotic plaques and allows mononuclear phagocytes to withstand cellular stress on exposure to hypoxia and modified low density lipoprotein. *J. Clin. Invest.* 98:1930–1941.

Vallee, B. L. and Auld, D. S. (1990) *Biochemistry* 29, 5647–5659.

van Genderen, I. L., Brandimarti, R., Torrisi, M. R., Campadelli, G., and van Meer, G. (1994) *Virology* 200, 831–836.

van Meer, G. 1993. Transport and sorting of membrane lipids. *Curr. Opin. Cell Biol.* 5:661–673.

Varki, A. and Kornfeld, S. (1983) *J. Biol. Chem,.* 258, 2808–2818.

Watanabe, K., Sakuragawa, N., Arima, M., and Satoyoshi, E. (1983) *J. Lipid Res.* 24, 596–603.

Watson, A. D., J. A. Berliner, S. Y. Hama, B. N. La Du, K. F. Faull, A. M. Fogelman, and M. Navab. 1995. Protective effect of high density lipoprotein associated paraoxonase. Inhibition of the biological activity of minimally oxidized low density lipoprotein. *J. Clin. Invest.* 96:2882–2891.

Weltzien, H. U. 1979. Cytolytic and membrane-perturbing properties of lysophosphatidylcholine. *Biochim. Biophys. Acta* 559:259–287.

Wiegmann, K., Schutze, S., Machleidt, T., Witte, D., and Kronke, M. (1994) *Cell* 78, 1005–1015.

Williams, K. J., G. M. Fless, K. A. Petrie, M. L. Snyder, R. W. Brocla, and T. L. Swenson. 1992. Mechanisms by which lipoprotein lipase alters cellular metabolism of lipoprotein(a), low density lipoprotein, and nascent lipoproteins. Roles for low density lipoprotein receptors and heparan sulfate proteoglycans. *J. Biol. Chem.* 267:13284–13292.

Williams, K. J. and I. Tabas. 1995. The response-to-retention hypothesis of early atherogenesis. *Arterioscler. Thromb. Vasc. Biol.* 15:551–561.

Xu, X. and I. Tabas. 1991. Sphingomyelinase enhances low density lipoprotein uptake and ability to induce cholesteryl ester accumulation in macrophages. *J. Biol. Chem.* 266:24849–24858.

Yamaguchi, S. and Suzuki, K. (1977) *J. Biol. Chem.* 252, 3805–3813.

Yamamoto, K. (1994) *J. Biochem.* 116, 229–235.

Ylä-Herttuala, S., W. Palinski, M. E. Rosenfeld, S. Parthasarathy, T. E. Carew, S. Butler, J. L. Witztum, and D. Steinberg. 1989. Evidence for the presence of oxidatively modified low density lipoprotein in atherosclerotic lesions of rabbit and man. *J. Clin. Invest.* 84:1086–1095.

Ylä-Herttuala, S., B. A. Lipoton, M. E. Rosenfeld, I. J. Goldberg, D. Steinberg, and J. L. Witztum. 1991. Macrophages and smooth muscle cells express lipoprotein lipase in human and rabbit atherosclerotic lesions. *Proc. Natl. Acad. Sci. USA* 88:10143–10147.

Zhang, S. H., R. L. Reddick, J. A. Piedrahita, and N. Maeda. 1992. Spontaneous hypercholesterolemia and arterial lesions in mice lacking apolipoprotein E. *Science* 258:468–471.

What is claimed is:

1. A method for treating a subject suffering from an atherosclerotic vascular disease which comprises administering to the subject an amount of a zinc sphingomyelinase inhibitor effective to decrease extracellular zinc sphingomyelinase activity in the subject and thereby treat the subject, wherein the inhibitor comprises a portion of a naturally occurring zinc sphingomyelinase, wherein the portion consists essentially of a sphingomyelin-binding site of the naturally occurring zinc sphingomyelinase.

2. The method of claim 1, wherein the extracellular zinc sphingomyelinase is present in the subject at a concentration which is higher than that present in the subject prior to the onset of the condition.

3. The method of claim 1, wherein the atherosclerotic vascular disease is coronary artery disease, cerebral vascular disease, peripheral vascular disease, transplantation atherosclerosis, vein graft atherosclerosis, or vaculitis-induced atherosclerosis.

4. The method of claim 1, wherein the administration comprises intralesional, intraperitoneal, intramuscular or intravenous injection;

infusion;

liposome-mediated delivery;

topical, nasal, oral, anal, subcutaneous, vaginal, sublingual, intrathecal, uretheral, transdermal, ocular or otic delivery.

5. The method of claim 1, wherein the portion of the naturally occurring zinc sphingomyelinase consists of the sphingomyelin-binding site.

* * * * *